US010973875B2

(12) United States Patent
Loskog

(10) Patent No.: US 10,973,875 B2
(45) Date of Patent: Apr. 13, 2021

(54) MEDICAL AGENTS AND USES THEREOF

(71) Applicant: LOKON PHARMA AB, Uppsala (SE)

(72) Inventor: Angelica Loskog, Uppsala (SE)

(73) Assignee: LOKON PHARMA AB, Uppsala (SE)

(*) Notice: Subject to any disclaimer, the term of this patent is extended or adjusted under 35 U.S.C. 154(b) by 375 days.

(21) Appl. No.: 15/127,877

(22) PCT Filed: Apr. 7, 2015

(86) PCT No.: PCT/EP2015/057489
§ 371 (c)(1),
(2) Date: Sep. 21, 2016

(87) PCT Pub. No.: WO2015/155174
PCT Pub. Date: Oct. 15, 2015

(65) Prior Publication Data
US 2017/0189480 A1 Jul. 6, 2017

(30) Foreign Application Priority Data

Apr. 7, 2014 (EP) ..................................... 14163704

(51) Int. Cl.
*C12N 15/62* (2006.01)
*A61K 31/713* (2006.01)
*C12N 15/86* (2006.01)
*A61P 37/02* (2006.01)
*A61K 38/17* (2006.01)
*C07K 14/705* (2006.01)

(52) U.S. Cl.
CPC .... *A61K 38/1709* (2013.01); *C07K 14/70575* (2013.01); *C07K 2319/03* (2013.01); *C07K 2319/735* (2013.01)

(58) Field of Classification Search
None
See application file for complete search history.

(56) References Cited

U.S. PATENT DOCUMENTS

2003/0119149 A1* 6/2003 Reddy .............. C07K 14/70575
435/69.5

FOREIGN PATENT DOCUMENTS

WO    WO 94/10308 A1    5/1994
WO    WO 02/36769 A2    5/2002
WO    WO 2007/120368 A2   10/2007

OTHER PUBLICATIONS

Jagodzinski et al, Using Rigidity Analysis To Probe Mutation-Induced Structural Changes in Proteins, 2012, World Scientific, pp. 1-6.*
GenBank: L07414.1, *Homo sapiens* CD40 surface protein mRNA, complete cds, downloaded Feb. 12, 2019, pp. 1-2.*
1GCM_A, Chain A, Gcn4 Leucine Zipper Core Mutant P—Li-Protein—NCBI, downloaded Feb. 12, 2019, pp. 1-2.*
Tcherepanova et al, Ectopic expression of a truncated CD40L protein from synthetic post-transcriptionally capped RNA in dendritic cells induces high levels of IL-12 secretion, BMC Molecular Biology 2008.*
Lilienfeldt et al, A Hexon and Fiber-modified Adenovirus Expressing CD40L Improves the Antigen Presentation Capacity of Dendritic Cells, J Immunother, Apr. 1, 2014, pp. 155-162.*
De Keersmaeckeretal, The combination of 4-1BBL and CD40L strongly enhances the capacity of dendritic cells to stimulate HIV-specific T cell responses J. Leukoc. Biol. 89: 989-999; 2011.*
Meziane et al, Use of Adenoviruses Encoding CD40L or IL-2 Against B Cell Lymphoma, Int. J. Cancer: 111, 910-920 (2004).*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Naito et al, CD40L-Tri, a novel formulation of recombinant human CD40L that effectively activates B cells, Cancer Immunol Immunother (2013) 62:347-357.*
Baccam and Bishop, Membrane-bound CD154, but not CD40-specific antibody, mediates NF-B B-independent IL-6 production in B cells, Eur. J. Immunol. 1999. 29: 3855-3866.*
Kidd, kozak leading sequence, 1998, p. 1.*
GenBank: BC104807.1, *Homo sapiens* tumor necrosis factor (ligand) superfamily, member 9, mRNA (cDNA clone MGC:132467 IMAGE:8143810), complete cds, downloaded Feb. 3, 2020.*
Yacoub et al, CD154 Is Released from T-cells by a Disintegrin and Metalloproteinase Domain-containing Protein 10 (ADAM10) and ADAM17 in a CD40 Protein-dependent Manner, The Journal of Biological Chemistry vol. 288, No. 50, p. 36083-36093, Dec. 13, 2013.*
Blaeser et al., "Critical function of the CD40 pathway in parvovirus B19 infection revealed by a hypomorphic CD40 ligand mutation," Clinical Immunology, vol. 117, No. 3, pp. 231-237, Dec. 2005.
Hsu et al., "Heteromultimeric complexes of CD40 ligand are present on the cell surface of human T lymphocytes," Journal of Biological Chemistry, vol. 272, No. 2, pp. 911-915, Jan. 1997.
Morris et al., "Incorporation of an Isoleucine ziper motif enhances the biological activity of soluble CD40L (CD154)," Journal of Biological Chemistry, vol. 274, No. 1, pp. 418-423, Jan. 1999.
Svensson et al., "Immunotherapy with a CD40L/4-1BBL double-armed oncolytic adenovirus drives Th1 immunity and control tumor progression in a pancreas cancer model," AACR Annual Meeting, Apr. 19, 2015.

(Continued)

*Primary Examiner* — Maria Marvich
(74) *Attorney, Agent, or Firm* — Foley & Lardner LLP

(57) ABSTRACT

The invention provides a novel compounds derived from CD154, but without the intracellular domain. Notably, the invention provides TMZ-CD154 and a method to treat diseases in which the novel molecule TMZ-CD154 is used. In particular, TMZ-CD154 is used to modify the immune responses in patients with immune related diseases such as cancer and infectious disease. The invention also relates to a method to activate cells with the TMZ-CD154 in vitro either prior to using the activated cells for therapy or for diagnostic purposes.

Figure 1:
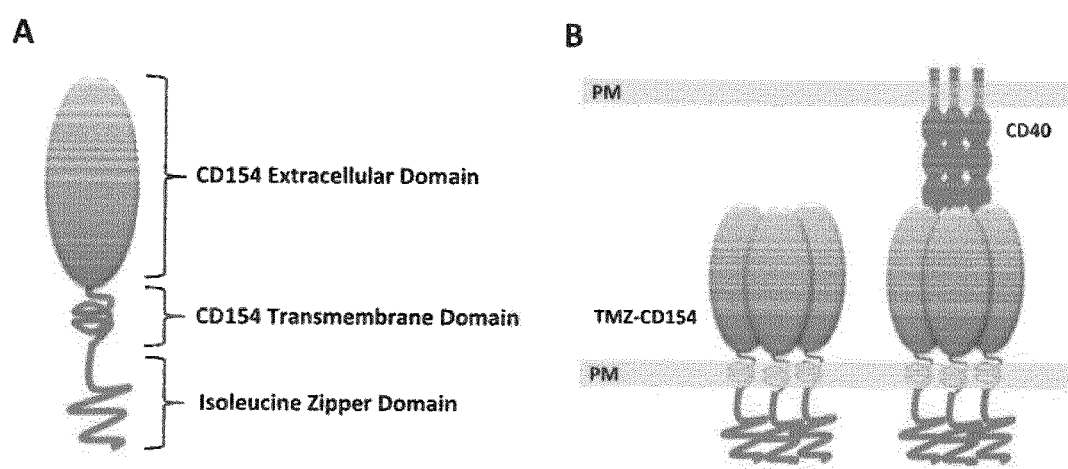

35 Claims, 25 Drawing Sheets
Specification includes a Sequence Listing.

(56) References Cited

OTHER PUBLICATIONS

Curran et al., "Enhancing anti-tumor efficacy of chimeric antigen receptor T cells through constitutive CD40L expression," Molecular Therapy, accepted article preview online, Jan. 13, 2015.

Berry et al., "Substitute of Cyseine for Selenocystein in Type I Iodothyronine Deiodinase Reduces the Catalytic Efficiency of the Protein but Enhances its Translation," Endocrinology, vol. 131, No. 4, pp. 1848-1582 (1992).

Brown et al., "Thymic lymphoproliferative disease after successful correction of DC40 ligand deficiency by gene transfer in mice," Nature Medicine, vol. 4, No. 11, pp. 1253-1260 (Nov. 1998).

Elmetwali et al., "CD40 ligand induced cytotoxicity in carcinoma cells is enhanced by inhibition of metalloproteinase cleavage and delivery via a conditionally-replicating adenovirus," Molecular Cancer, vol. 9, No. 52, pp. 1-12 (2010).

Eriksson et al., "IL-6 Signaling Blockade during CD40-Mediated Immune Activation Favors Antitumor Factors by Reducing TGF-β, Collagen Type I, and PD-L1/PD1," The Journal of Immunology, vol. 202, pp. 787-798 (2019).

Eriksson et al., "Shaping the Tumor Stroma and Sparking Immune Activation by CD40 and 4-1BB Signaling Induced by an Armed Oncoltic Virus," Clinical Cancer Research, vol. 23, No. 19 (Oct. 2017).

Galivo et al., "Interference of CD40L-Mediated Tumor Immunotherapy by Oncolytic Vesicular Stomatitis Virus," Human Gene Therapy, vol. 21, pp. 439-450 (Apr. 2010).

Huang et al., "Elevated serum soluble CD40 ligand in cancer patients may play an immunosuppressive role," Blood, vol. 120, No. 15, pp. 3030-3038 (2012).

Khokha et al., "Metalloproteinases and their natural inhibitors in inflammation and immunity," Nature Reviews, Immunology, vol. 13, pp. 649-665 (Sep. 2013).

Liljenfeldt et al., "CD40L gene therapy tilts the myeloid cell profile and promotes infiltration of activated T lymphocytes," Cancer Gene Therapy (2014) vol. 21, pp. 95-102.

Niewiesk et al., "Measles Virus-Induced Immune Suppression in the Cotton Rat (*Sigmodon hispidus*) Model Depends on Virual Glycoproteins," Journal of Virology, vol. 71, No. 10, pp. 7217-7219 (Oct. 1997).

Pakula et al., "Genetic Analysis of Protein Stability and Function," Ann. Rev. Genet. vol. 23, pp. 289-310 (1989).

Sakurai et al., "Transduction Properties of Adenovirus Serotype 35 Vectors After Intravenous Administration Into Nonhuman Primates," Molecular Therapy, vol. 16, No. 4, pp. 726-733 (Apr. 2008).

Tsujimura et al., "Molecular cloning of a murine homologue of membrane cofactor protein (CD46): preferential expression in testicular germ cells," Biochem. J., vol. 330, pp. 163-168 (1998).

Chen et al., "Fusion Protein Linkers: Property, Design and Functionality," Adv Drug Deliv Rev. (Oct. 2013) 65(10): 1357-1369.

Eriksson et al., "Gemcitabine reduces MDSCs, tregs and TGFβ-1 while restoring the teff/treg ratio in patients with pancreatic cancer," Journal of Translational Medicine (2016) 14:282.

Khairallah et al., "Impact of neoadjuvant chemotherapy on the immune microenvironment in advanced epithelial ovarian cancer: Prognostic and therapeutic implications," Int. J. Cancer: 143, 8-15 (2018) (avail online Dec. 8, 2017).

Soliman, "nab-Paclitaxel as a potential partner with checkpoint inhibitors in solid tumors," OncoTargets and Therapy 2017:10 101-112.

Othman et al., "Cancer-Derived Exosomes as Effectors of Key Inflammation-Related Players," Frontiers in Immunology, vol. 10, Article 2103 (Sep. 2019).

Harbury et al., "Crystal structure of an isoleucine-zipper trimer," Nature, vol. 371, pp. 80-83 (Sep. 1994).

Maeda et al., "Engineering of Functional Chimeric Protein G-Vargula Luciferase," Analytical Biochemistry 249, 147-152 (1997).

Stark et al., "The use of trimeric isoleucine-zipper fusion proteins to study surface-receptor-ligand interactions in natural killer cells," J. Imm. Methods, 296 (2005) 149-158 (Available online Dec. 2004).

Kornbluth et al., "Design of CD40 Agonists and their use in growing B cells for cancer immunotherapy," Int Rev Immunol., vol. 31, No. 4, pp. 279-288 (Aug. 2012).

Stone et al., "Multimeric Soluble CD40 Ligand and GITR Ligand as Adjuvants for Human Immunodeficiency Virus DNA Vaccines," Journal of Virology, vol. 80, No. 4, pp. 1762-1772 (Feb. 2006).

\* cited by examiner

A

B

A

B

C

A

B

A

B

SEQUENCE LISTING

```
<160> NUMBER OF SEQ ID NOS: 29

<210> SEQ ID NO 1
<211> LENGTH: 846
<212> TYPE: DNA
<213> ORGANISM: Artificial sequence
<220> FEATURE:
<223> OTHER INFORMATION: TMZ-CD154 comprising sequences from Homo
      sapiens and Saccharomyces cerevisae, and modified and synthezised
      sequences

<400> SEQUENCE: 1
gccaccatga gaatgaagca gatcgaggac aagatcgagg agatcctgag caagatctac        60
cacatcgaga acgagatcgc cagaatcaag aagctgatcg gcgagagagg cggccggggc       120
ggcggcattt ttatgtattt acttactgtt tttcttatca cccagatgat tgggtcagca       180 cttttttgctg tgtatcttca tagaaggttg gacaagatag aagatgaaag gaatcttcat      240
gaagattttg tattcatgaa aacgatacag agatgcaaca caggagaaag atccttatcc      300
ttactgaact gtgaggagat taaaagccag tttgaaggct tgtgaagga tataatgtta        360 aacaaagagg agacgaagaa agaaaacagc tttgaaatgc aaaaaggtga tcagaatcct      420
caaattgcgg cacatgtcat aagtgaggcc agcagtaaaa caacatctgt gttacagtgg       480
gctgaaaaag gatactacac catgagcaac aacttggtaa ccctggaaaa tgggaaacag      540
ctgaccgtta aaagacaagg actctattat atctatgccc aagtcacctt ctgttccaat      600
cgggaagctt cgagtcaagc tccatttata gccagcctct gcctaaagtc ccccggtaga       660
ttcgagagaa tcttactcag agctgcaaat acccacagtt ccgccaaacc ttgcgggcaa      720
caatccattc acttgggagg agtatttgaa ttgcaaccag gtgcttcggt gtttgtcaat       780
gtgactgatc caagccaagt gagccatggc actggcttca cgtcctttgg cttactcaaa      840
ctctga                                                                  846

<210> SEQ ID NO 2
<211> LENGTH: 279
<212> TYPE: PRT
<213> ORGANISM: Artificial sequence
<220> FEATURE:
<223> OTHER INFORMATION: TMZ-CD154 comprising sequences from Homo
      sapiens and Saccharomyces cerevisae, and modified and synthezised
      sequences

<400> SEQUENCE: 2
```

Met Arg Met Lys Gln Ile Glu Asp Lys Ile Glu Glu Ile Leu Ser Lys
1               5                   10                  15

Ile Tyr His Ile Glu Asn Glu Ile Ala Arg Ile Lys Lys Leu Ile Gly
            20                  25                  30

Glu Arg Gly Arg Gly Gly Gly Ile Phe Met Tyr Leu Leu Thr Val
        35                  40                  45

Phe Leu Ile Thr Gln Met Ile Gly Ser Ala Leu Phe Ala Val Tyr Leu
    50                  55                  60

His Arg Arg Leu Asp Lys Ile Glu Asp Glu Arg Asn Leu His Glu Asp
65                  70                  75                  80

Phe Val Phe Met Lys Thr Ile Gln Arg Cys Asn Thr Gly Glu Arg Ser
                85                  90                  95

Leu Ser Leu Leu Asn Cys Glu Glu Ile Lys Ser Gln Phe Glu Gly Phe
            100                 105                 110

Val Lys Asp Ile Met Leu Asn Lys Glu Glu Thr Lys Lys Glu Asn Ser
        115                 120                 125

Phe Glu Met Gln Lys Gly Asp Gln Asn Pro Gln Ile Ala Ala His Val
    130                 135                 140

Ile Ser Glu Ala Ser Ser Lys Thr Thr Ser Val Leu Gln Trp Ala Glu
145                 150                 155                 160

Lys Gly Tyr Tyr Thr Met Ser Asn Asn Leu Val Thr Leu Glu Asn Gly
                165                 170                 175

Lys Gln Leu Thr Val Lys Arg Gln Gly Leu Tyr Tyr Ile Tyr Ala Gln
            180                 185                 190

Val Thr Phe Cys Ser Asn Arg Glu Ala Ser Ser Gln Ala Pro Phe Ile
        195                 200                 205

Ala Ser Leu Cys Leu Lys Ser Pro Gly Arg Phe Glu Arg Ile Leu Leu
210                 215                 220

Arg Ala Ala Asn Thr His Ser Ser Ala Lys Pro Cys Gly Gln Gln Ser
225                 230                 235                 240

Ile His Leu Gly Gly Val Phe Glu Leu Gln Pro Gly Ala Ser Val Phe
                245                 250                 255

Val Asn Val Thr Asp Pro Ser Gln Val Ser His Gly Thr Gly Phe Thr
            260                 265                 270

Ser Phe Gly Leu Leu Lys Leu
        275

<210> SEQ ID NO 3
<211> LENGTH: 846
<212> TYPE: DNA
<213> ORGANISM: Artificial sequence
<220> FEATURE:
<223> OTHER INFORMATION: TMZ-CD154 comprising sequences from Equus
      caballus and Saccharomyces cerevisae, and modified and synthezised
      sequences

<400> SEQUENCE: 3
gccaccatga gaatgaagca gatcgaggac aagatcgagg agatcctgag caagatctac    60
cacatcgaga acgagatcgc cagaatcaag aagctgatcg gcgagagagg cggccggggc    120
ggcggcattt ttatgtattt gcttactgtt tttcttatca cccagatgat tgtgtcagca    180 cttttttgctg tgtatcttca cagaagattg acaagataga agatgaaag gaatcttcat    240 gaagattttg tgttcatgaa aacgatacag agatgcaaca aggagaggg gcctttatca    300 ttactgaact gtgaggaaat tagaagccag ttcgaaggct cgtcaagga tataatgcta    360

```
aatgaagaag tgaagaagaa aggagaaaac tttgaaatgc aaaaaggcga tcaggagcct    420
caaattgcgg cacatgtcat aagtgaggcc agcagtaaaa cagcatctgt tctacagtgg    480
gcccaaaaag gatactacac cataagcaac aacttggtaa ccctcgaaaa tgggaaacag    540
ctggccgtta aaagacaagg actctattat atctatgccc aagtcacctt ctgttccaat    600
cgggaagctt cgggtcaagc tccatttata gccagcctct gcctgaggtc cgtgagtgga    660
tctgagagaa tcttacttag agcggcaaat acccacagtt cctccaaacc ttgcgggcag    720
caatccattc acttgggagg agtatttgaa ttgcaaccag gtgcttcggt gtttgtcaac    780
gtgactgatc caagccaagt gagccatggg accggcttca catctttttgg tttactcaaa    840 ctctga                                                               846

<210> SEQ ID NO 4
<211> LENGTH: 844
<212> TYPE: DNA
<213> ORGANISM: Artificial sequence
<220> FEATURE:
<223> OTHER INFORMATION: TMZ-CD154 comprising sequences from Canis lupus
      familiaris and Saccharomyces cerevisae, and modified and
      synthezised sequences

<400> SEQUENCE: 4
gccaccatga gaatgaagca gatcgaggac aagatcgagg agatcctgag caagatctac     60
cacatcgaga acgagatcgc cagaatcaag aagctgatcg gcgagagagg cggccggggc    120
ggcggcattt ttatgtattt gcttactgtt tttctcatca cccagatgat tggatcggca    180
ctctttgctg tatatcttca cagaagattg gacaagatag aagatgaaag gaatctttat    240
gaagattttg tgttcatgaa aacgttacag aaatgcaaca aggggagggg gtccttgtcc    300
ttactgaact gtgaggaaat taaaagccaa tttgaagcct ttctcaagga gataatgcta    360
aacaacgaaa tgaagaaaga gaaaacatt gcaatgcaaa aaggtgatca ggatcctcga    420
attgcagccc atgtcataag tgaggctagt agtaacccag cgtccgttct gcggtgggcg    480
ccaaaagggt actacaccat aagcagcaac ctggtgagcc tcgagaatgg gaaacagttg    540
gccgtgaaaa gacaaggact ctattacgtc tatgcccaag tcaccttctg ctccaatcgg    600
gcagcttcga gtcaagctcc gttcgtcgcc agcctatgcc tccattcccc gagtggaacg    660
gagagagtct tactccgcgc cgcgagctcc cgcggctcgt ccaaaccttg cggccaacag    720
tccatccact ggggaggagt atttgaattg catccaggtg cttcggtgtt cgtcaacgtg    780
actgatccaa gccaagtgag ccacgggacc ggcttcacgt cttttggctt actcaaactc    840
tgaa                                                                 844

<210> SEQ ID NO 5
<211> LENGTH: 844
<212> TYPE: DNA
<213> ORGANISM: Artificial sequence
<220> FEATURE:
<223> OTHER INFORMATION: TMZ-CD154 comprising sequences from Felis catus
      and Saccharomyces cerevisae, and modified and synthezised
      sequences

<400> SEQUENCE: 5
gccaccatga gaatgaagca gatcgaggac aagatcgagg agatcctgag caagatctac     60
cacatcgaga acgagatcgc cagaatcaag aagctgatcg gcgagagagg cggccggggc    120
ggcggcattt ttatgtattt acttactgtg tttctcatca cccagatgat tgggtcagca    180
ctctttgctg tgtatcttca cagaagactg gacaagatag aagatgaaag gaatctttat    240
```

```
gaagattttg tgttcatgaa acattacag aaatgcaaca aaggagaggg ggccttatcc    300
ttactgaact gtgaggaaat taaaagccgg tttgaagcct ttctcaagga gataatgcta    360
aacaaagaaa cgaagaaaga aaaaaatgtt gcaatgcaaa aaggcgacca ggatcctcga    420
gttgcagcac atgtcataag tgaggccagc agtagcacag cgtctgttct ccagtgggcc    480
cccaaaggct actacaccat aagcagcaac ttggtgaccc tcgagaacgg aagcagctg    540 gccgttaaaa gacaaggact ctattatatc tacgcccaag tcaccttctg ttccaatcgg    600
gaagcttcga gtcaagctcc gttcatagcc agcctctgcc tgcattcccc gagtggatcc    660
gagagagtct tactcagagc tgcaaatgcc cgcagttcct ccaaaccctg tgggcagcaa    720
tccattcact tgggaggagt cttcgaactg catccaggtg cttcggtgtt cgtgaacgtg    780
actgatccga ccaagtgag ccacgggacg ggcttcacgt cttttggctt actcaaactc    840
tgaa                                                                844
```

`<210>` SEQ ID NO 6
`<211>` LENGTH: 1668
`<212>` TYPE: DNA
`<213>` ORGANISM: Artificial Sequence
`<220>` FEATURE:
`<223>` OTHER INFORMATION: TMZ-CD154/4-1BBL comprising sequences from Homo
       sapiens, Thosea asigna, Saccharomyces cerevisae, and modified and
       synthezised sequences

`<400>` SEQUENCE: 6

```
gccaccatgg aatacgcctc tgacgcttca ctggaccccg aagccccgtg gcctcccgcg    60
ccccgcgctc gcgcctgccg cgtactgcct tgggccctgg tcgcggggct gctgctgctg    120
ctgctgctcg ctgccgcctg cgccgtcttc ctcgcctgcc cctgggccgt gtccggggct    180
cgcgcctcgc ccggctccgc ggccagcccg agactccgcg agggtcccga gctttcgccc    240
gacgatcccg ccggcctctt ggacctgcgg cagggcatgt ttgcgcagct ggtggcccaa    300
aatgttctgc tgatcgatgg gccctgagc tggtacagtg acccaggcct ggcaggcgtg    360
tccctgacgg ggggcctgag ctacaaagag gacacgaagg agctggtggt ggccaaggct    420
ggagtctact atgtcttctt tcaactagag ctgcggcgcg tggtggccgg cgagggctca    480
ggctccgttt cacttgcgct gcacctgcag ccactgcgct ctgctgctgg ggccgccgcc    540
ctggctttga ccgtggacct gccacccgcc tcctccgagg ctcggaactc ggccttcggt    600
ttccagggcc gcttgctgca cctgagtgcc ggccagcgcc tgggcgtcca tcttcacact    660
gaggccaggg cacgccatgc ctggcagctt acccagggcg ccacagtctt gggactcttc    720
cgggtgaccc ccgaaatccc agccggactc ccttcaccga ggtcggaagg ctccggggag    780
ggcagaggaa gtctgctaac atgcggtgac gtcgaggaga tcctgggcc agaatgaag    840 cagatcgagg acaagatcga ggagatcctg agcaagatct accacatcga gaacgagatc    900
gccagaatca gaagctgat cggcgagaga ggcggcgggg cgcggcggat tttatgtat    960 ttacttactg ttttttcttat cacccagatg attgggtcag cactttttgc tgtgtatctt    1020
catagaaggt tggacaagat agaagatgaa aggaatcttc atgaagattt tgtattcatg    1080
aaaacgatac agagatgcaa cacaggagaa agatccttat ccttactgaa ctgtgaggag    1140
attaaaagcc agtttgaagg ctttgtgaag gatataatgt taaacaaaga ggagacgaag    1200
aaagaaaaca gctttgaaat gcaaaaaggt gatcagaatc ctcaaattgc ggcacatgtc    1260
ataagtgagg ccagcagtaa aacaacatct gtgttacagt gggctgaaaa aggatactac    1320
```

-continued

```
accatgagca caaacttggt aaccctggaa aatgggaaac agctgaccgt taaaagacaa    1380
ggactctatt atatctatgc ccaagtcacc ttctgttcca atcgggaagc ttcgagtcaa    1440
gctccattta tagccagcct ctgcctaaag tcccccggta gattcgagag aatcttactc    1500
agagctgcaa atacccacag ttccgccaaa ccttgcgggc aacaatccat tcacttggga    1560
ggagtatttg aattgcaacc aggtgcttcg gtgtttgtca atgtgactga tccaagccaa    1620
gtgagccatg gcactggctt cacgtccttt ggcttactca aactctga                 1668
```

<210> SEQ ID NO 7
<211> LENGTH: 551
<212> TYPE: PRT
<213> ORGANISM: Artificial Sequence
<220> FEATURE:
<223> OTHER INFORMATION: TMZ-CD154/4-1BBL comprising sequences from Homo
      sapiens, Thosea asigna, Saccharomyces cerevisae, and modified and
      synthezised sequences

<400> SEQUENCE: 7

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Ala Gly Val Ser Leu Thr Gly Gly Leu Ser Tyr Lys Glu Asp
        115                 120                 125

Thr Lys Leu Val Val Ala Lys Ala Gly Val Tyr Tyr Val Phe Phe Gln
    130                 135                 140

Leu Glu Leu Arg Arg Val Val Ala Gly Glu Gly Ser Gly Ser Val Ser
145                 150                 155                 160

Leu Ala Leu His Leu Gln Pro Leu Arg Ser Ala Ala Gly Ala Ala Ala
                165                 170                 175

Leu Ala Leu Thr Val Asp Leu Pro Pro Ala Ser Ser Glu Ala Arg Asn
            180                 185                 190

Ser Ala Phe Gly Phe Gln Gly Arg Leu Leu His Leu Ser Ala Gly Gln
        195                 200                 205

Arg Leu Gly Val His Leu His Thr Glu Ala Arg Ala Arg His Ala Trp
    210                 215                 220

Gln Leu Thr Gln Gly Ala Thr Val Leu Gly Leu Phe Arg Val Thr Pro
225                 230                 235                 240

Glu Ile Pro Ala Gly Leu Pro Ser Pro Arg Ser Glu Gly Ser Gly Glu
                245                 250                 255

Gly Arg Gly Ser Leu Leu Thr Cys Gly Asp Val Glu Glu Asn Pro Gly
            260                 265                 270

Pro Arg Met Lys Gln Ile Glu Asp Lys Ile Glu Glu Ile Leu Ser Lys
        275                 280                 285

Ile Tyr His Ile Glu Asn Glu Ile Ala Arg Ile Lys Lys Leu Ile Gly
```

```
                290             295             300
Glu Arg Gly Gly Arg Gly Gly Ile Phe Met Tyr Leu Leu Thr Val
305             310             315             320

Phe Leu Ile Thr Gln Met Ile Gly Ser Ala Leu Phe Ala Val Tyr Leu
                325             330             335

His Arg Arg Leu Asp Lys Ile Glu Asp Glu Arg Asn Leu His Glu Asp
                340             345             350

Phe Val Phe Met Lys Thr Ile Gln Arg Cys Asn Thr Gly Glu Arg Ser
            355             360             365

Leu Ser Leu Leu Asn Cys Glu Glu Ile Lys Ser Gln Phe Glu Gly Phe
        370             375             380

Val Lys Asp Ile Met Leu Asn Lys Glu Glu Thr Lys Lys Glu Asn Ser
385             390             395             400

Phe Glu Met Gln Lys Gly Asp Gln Asn Pro Gln Ile Ala Ala His Val
                405             410             415

Ile Ser Glu Ala Ser Ser Lys Thr Thr Ser Val Leu Gln Trp Ala Glu
                420             425             430

Lys Gly Tyr Tyr Thr Met Ser Asn Asn Leu Val Thr Leu Glu Asn Gly
            435             440             445

Lys Gln Leu Thr Val Lys Arg Gln Gly Leu Tyr Tyr Ile Tyr Ala Gln
        450             455             460

Val Thr Phe Cys Ser Asn Arg Glu Ala Ser Ser Gln Ala Pro Phe Ile
465             470             475             480

Ala Ser Leu Cys Leu Lys Ser Pro Gly Arg Phe Glu Arg Ile Leu Leu
                485             490             495

Arg Ala Ala Asn Thr His Ser Ser Ala Lys Pro Cys Gly Gln Gln Ser
                500             505             510

Ile His Leu Gly Gly Val Phe Glu Leu Gln Pro Gly Ala Ser Val Phe
            515             520             525

Val Asn Val Thr Asp Pro Ser Gln Val Ser His Gly Thr Gly Phe Thr
        530             535             540

Ser Phe Gly Leu Leu Lys Leu
545             550
```

<210> SEQ ID NO 8
<211> LENGTH: 1698
<212> TYPE: DNA
<213> ORGANISM: Artificial Sequence
<220> FEATURE:
<223> OTHER INFORMATION: TMZ-CD154/T2A/aIL6R scFv comprising sequences
      from Homo sapiens, Thosea asigna, Saccharomyces cerevisae, Mus
      musculus, and modified and synthezised sequences

<400> SEQUENCE: 8

```
gccaccatgc acagctcagc actgctctgt tgcctggtcc tcctgactgg ggtgagggcc      60
caggtccaac tgcaggagag cggtccaggt cttgtgagac ctagccagac cctgagcctg     120
acctgcaccg tgtctggcta ctcaattacc agcgatcatg cctggagctg gttcgccag     180 ccacctggac gaggtcttga gtggattgga tacattagtt atagtggaat cacaacctat     240
aatccatctc tcaaatccag agtgacaatg ctgagagaca ccagcaagaa ccagttcagc     300
ctgagactca gcagcgtgac agccgccgac accgcggttt attattgtgc aagatcccta     360
gctcggacta cggctatgga ctactggggt caaggcagcc tcgtcacagt ctcctcaggt     420
ggcggtggct cgggtggcgg tggctcgggc ggtggtgggt cgggtggcgg cggatcagac     480
atccagatga cccagagccc aagcagcctg agcgccagcg tgggtgacag ggtgaccatc     540
```

```
acctgtcgag ccagccagga catcagcagt tacctgaatt ggtaccagca gaagccagga      600
aaggctccaa agctgctgat ctactacacc tcccgcctgc actctggtgt gccaagcaga      660
ttcagcggta gcggtagcgg taccgacttc accttcacca tcagcagcct ccagccagag      720
gacatcgcta cctactactg ccagcagggt aacacgcttc catacacgtt cggccaaggg      780
accaaggtgg aaatcaaagg ctccggggag ggcagaggaa gtctgctaac atgcggtgac      840
gtcgaggaga tcctgggcc cagaatgaag cagatcgagg acaagatcga ggagatcctg      900
agcaagatct accacatcga aacgagatc gccagaatca agaagctgat cggcgagaga      960
ggcggccggg gcggcggcat ttttatgtat ttacttactg tttttcttat cacccagatg     1020
attgggtcag cacttttgc tgtgtatctt catagaaggt tggacaagat agaagatgaa     1080
aggaatcttc atgaagattt tgtattcatg aaaacgatac agagatgcaa cacaggagaa     1140
agatccttat ccttactgaa ctgtgaggag attaaaagcc agtttgaagg ctttgtgaag     1200
gatataatgt taaacaaaga ggagacgaag aagaaaaca gctttgaaat gcaaaaaggt      1260
gatcagaatc ctcaaattgc ggcacatgtc ataagtgagg ccagcagtaa acaacatct      1320 gtgttacagt gggctgaaaa aggatactac accatgagca caacttggt aaccctggaa     1380 aatgggaaac agctgaccgt taaaagacaa ggactctatt atatctatgc ccaagtcacc     1440
ttctgttcca atcgggaagc ttcgagtcaa gctccattta tagccagcct ctgcctaaag     1500
tcccccggta gattcgagag aatcttactc agagctgcaa atacccacag ttccgccaaa     1560
ccttgcgggc aacaatccat tcacttggga ggagtatttg aattgcaacc aggtgcttcg     1620
gtgtttgtca atgtgactga tccaagccaa gtgagccatg gcactggctt cacgtccttt     1680
ggcttactca aactctga                                                   1698

<210> SEQ ID NO 9
<211> LENGTH: 563
<212> TYPE: PRT
<213> ORGANISM: Artificial Sequence
<220> FEATURE:
<223> OTHER INFORMATION: TMZ-CD154/T2A/aIL6R scFv comprising sequences
      from Homo sapiens, Thosea asigna, Saccharomyces cerevisae, Mus
      musculus, and modified and synthezised sequences

<400> SEQUENCE: 9

Met His Ser Ser Ala Leu Leu Cys Cys Leu Val Leu Leu Thr Gly Val
1               5                   10                  15

Arg Ala Gln Val Gln Leu Gln Glu Ser Gly Pro Gly Leu Val Arg Pro
            20                  25                  30

Ser Gln Thr Leu Ser Leu Thr Cys Thr Val Ser Gly Tyr Ser Ile Thr
        35                  40                  45

Ser Asp His Ala Trp Ser Trp Val Arg Gln Pro Pro Gly Arg Gly Leu
    50                  55                  60

Glu Trp Ile Gly Tyr Ile Ser Tyr Ser Gly Ile Thr Thr Tyr Asn Pro
65                  70                  75                  80

Ser Leu Lys Ser Arg Val Thr Met Leu Arg Asp Thr Ser Lys Asn Gln
                85                  90                  95

Phe Ser Leu Arg Leu Ser Ser Val Thr Ala Ala Asp Thr Ala Val Tyr
            100                 105                 110

Tyr Cys Ala Arg Ser Leu Ala Arg Thr Thr Ala Met Asp Tyr Trp Gly
        115                 120                 125

Gln Gly Ser Leu Val Thr Val Ser Gly Gly Gly Gly Ser Gly Gly
    130                 135                 140
```

```
Gly Gly Ser Gly Gly Gly Ser Gly Gly Gly Ser Asp Ile Gln
145                 150                 155             160

Met Thr Gln Ser Pro Ser Ser Leu Ser Ala Ser Val Gly Asp Arg Val
                165             170             175

Thr Ile Thr Cys Arg Ala Ser Gln Asp Ile Ser Ser Tyr Leu Asn Trp
            180             185             190

Tyr Gln Gln Lys Pro Gly Lys Ala Pro Lys Leu Leu Ile Tyr Tyr Thr
        195             200             205

Ser Arg Leu His Ser Gly Val Pro Ser Arg Phe Ser Gly Ser Gly Ser
    210             215             220

Gly Thr Asp Phe Thr Phe Thr Ile Ser Ser Leu Gln Pro Glu Asp Ile
225             230             235             240

Ala Thr Tyr Tyr Cys Gln Gln Gly Asn Thr Leu Pro Tyr Thr Phe Gly
                245             250             255

Gln Gly Thr Lys Val Glu Ile Lys Gly Ser Gly Glu Gly Arg Gly Ser
            260             265             270

Leu Leu Thr Cys Gly Asp Val Glu Glu Asn Pro Gly Pro Arg Met Lys
        275             280             285

Gln Ile Glu Asp Lys Ile Glu Glu Ile Leu Ser Lys Ile Tyr His Ile
    290             295             300

Glu Asn Glu Ile Ala Arg Ile Lys Lys Leu Ile Gly Glu Arg Gly Gly
305             310             315             320

Arg Gly Gly Gly Ile Phe Met Tyr Leu Leu Thr Val Phe Leu Ile Thr
                325             330             335

Gln Met Ile Gly Ser Ala Leu Phe Ala Val Tyr Leu His Arg Arg Leu
            340             345             350

Asp Lys Ile Glu Asp Glu Arg Asn Leu His Glu Asp Phe Val Phe Met
        355             360             365

Lys Thr Ile Gln Arg Cys Asn Thr Gly Glu Arg Ser Leu Ser Leu Leu
    370             375             380

Asn Cys Glu Glu Ile Lys Ser Gln Phe Glu Gly Phe Val Lys Asp Ile
385             390             395             400

Met Leu Asn Lys Glu Glu Thr Lys Lys Glu Asn Ser Phe Glu Met Gln
                405             410             415

Lys Gly Asp Gln Asn Pro Gln Ile Ala Ala His Val Ile Ser Glu Ala
            420             425             430

Ser Ser Lys Thr Thr Ser Val Leu Gln Trp Ala Glu Lys Gly Tyr Tyr
        435             440             445

Thr Met Ser Asn Asn Leu Val Thr Leu Glu Asn Gly Lys Gln Leu Thr
    450             455             460

Val Lys Arg Gln Gly Leu Tyr Tyr Ile Tyr Ala Gln Val Thr Phe Cys
465             470             475             480

Ser Asn Arg Glu Ala Ser Ser Gln Ala Pro Phe Ile Ala Ser Leu Cys
                485             490             495

Leu Lys Ser Pro Gly Arg Phe Glu Arg Ile Leu Leu Arg Ala Ala Asn
            500             505             510

Thr His Ser Ser Ala Lys Pro Cys Gly Gln Gln Ser Ile His Leu Gly
        515             520             525

Gly Val Phe Glu Leu Gln Pro Gly Ala Ser Val Phe Val Asn Val Thr
    530             535             540

Asp Pro Ser Gln Val Ser His Gly Thr Gly Phe Thr Ser Phe Gly Leu
545             550             555             560
```

Leu Lys Leu

<210> SEQ ID NO 10
<211> LENGTH: 261
<212> TYPE: PRT
<213> ORGANISM: Homo sapiens
<220> FEATURE:
<223> OTHER INFORMATION: full length CD154

<400> SEQUENCE: 10

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 11
<211> LENGTH: 648
<212> TYPE: DNA
<213> ORGANISM: Homo sapiens
<220> FEATURE:
<223> OTHER INFORMATION: Extracellular domain of human CD154

<400> SEQUENCE: 11
catagaaggt tggacaagat agaagatgaa aggaatcttc atgaagattt tgtattcatg     60
aaaacgatac agagatgcaa cacaggagaa agatccttat ccttactgaa ctgtgaggag    120
attaaaagcc agtttgaagg ctttgtgaag gatataagt taaacaaaga ggagacgaag    180

```
aaagaaaaca gctttgaaat gcaaaaggt gatcagaatc ctcaaattgc ggcacatgtc    240
ataagtgagg ccagcagtaa aacaacatct gtgttacagt gggctgaaaa aggatactac    300
accatgagca acaacttggt aaccctggaa atgggaaac agctgaccgt taaaagacaa    360
ggactctatt atatctatgc ccaagtcacc ttctgttcca atcgggaagc ttcgagtcaa    420
gctccattta tagccagcct ctgcctaaag tcccccggta gattcgagag aatcttactc    480
agagctgcaa atacccacag ttccgccaaa ccttgcgggc aacaatccat tcacttggga    540
ggagtatttg aattgcaacc aggtgcttcg gtgtttgtca atgtgactga tccaagccaa    600
gtgagccatg gcactggctt cacgtccttt ggcttactca aactctga                 648

<210> SEQ ID NO 12
<211> LENGTH: 720
<212> TYPE: DNA
<213> ORGANISM: Equus caballus
<220> FEATURE:
<223> OTHER INFORMATION: Extracellular domain of equine CD154

<400> SEQUENCE: 12
atttttatgt atttgcttac tgttttctt atcacccaga tgattgtgtc agcacttttt      60
gctgtgtatc ttcacagaag attggacaag atagaagatg aaaggaatct tcatgaagat    120
tttgtgttca tgaaaacgat acagagatgc aacaaggag aggggccttt atcattactg    180
aactgtgagg aaattagaag ccagttcgaa ggcttcgtca aggatataat gctaaatgaa    240
gaagtgaaga agaaaggaga aaactttgaa atgcaaaaag gcgatcagga gcctcaaatt    300
gcggcacatg tcataagtga ggccagcagt aaaacagcat ctgttctaca gtgggcccaa    360
aaaggatact acaccataag caacaacttg gtaaccctcg aaaatgggaa acagctggcc    420
gttaaaagac aaggactcta ttatatctat gcccaagtca ccttctgttc caatcgggaa    480
gcttcgggtc aagctccatt tatagccagc ctctgcctga ggtccgtgag tggatctgag    540
agaatcttac ttagagcggc aaatacccac agttcctcca aaccttgcgg gcagcaatcc    600
attcacttgg gaggagtatt tgaattgcaa ccaggtgctt cggtgtttgt caacgtgact    660
gatccaagcc aagtgagcca tgggaccggc ttcacatctt ttggtttact caaactctga    720

<210> SEQ ID NO 13
<211> LENGTH: 718
<212> TYPE: DNA
<213> ORGANISM: Canis lupus familiaris
<220> FEATURE:
<223> OTHER INFORMATION: Extracellular domain of canine CD154

<400> SEQUENCE: 13
atttttatgt atttgcttac tgttttctc atcacccaga tgattggatc ggcactcttt     60
gctgtatatc ttcacagaag attggacaag atagaagatg aaaggaatct ttatgaagat    120
tttgtgttca tgaaaacgtt acagaaatgc aacaagggg aggggtcctt gtccttactg    180
aactgtgagg aaattaaaag ccaatttgaa gcctttctca aggagataat gctaaacaac    240
gaaatgaaga agaagaaaa cattgcaatg caaaaaggtg atcaggatcc tcgaattgca    300
gcccatgtca taagtgaggc tagtagtaac ccagcgtccg ttctgcggtg ggcgccaaaa    360
gggtactaca ccataagcag caacctggtg agcctcgaga atgggaaaca gttggccgtg    420
aaaagacaag gactctatta cgtctatgcc caagtcacct tctgctccaa tcgggcagct    480
tcgagtcaag ctccgttcgt cgccagccta tgcctccatt ccccgagtgg aacgagagag    540
gtcttactcc gcgccgcgag ctcccgcggc tcgtccaaac cttgcggcca acagtccatc    600
```

```
cacttgggag gagtatttga attgcatcca ggtgcttcgg tgttcgtcaa cgtgactgat    660
ccaagccaag tgagccacgg gaccggcttc acgtcttttg gcttactcaa actctgaa     718
```

<210> SEQ ID NO 14
<211> LENGTH: 718
<212> TYPE: DNA
<213> ORGANISM: Felis catus
<220> FEATURE:
<223> OTHER INFORMATION: Extracellular domain of feline CD154

<400> SEQUENCE: 14

```
attttatgt atttacttac tgtgtttctc atcacccaga tgattgggtc agcactcttt    60
gctgtgtatc ttcacagaag actggacaag atagaagatg aaaggaatct ttatgaagat   120
tttgtgttca tgaaaacatt acagaaatgc aacaaggag aggggggcctt atccttactg   180 aactgtgagg aaattaaaag ccggtttgaa gcctttctca aggagataat gctaaacaaa    240
gaaacgaaga agaaaaaaa tgttgcaatg caaaaaggcg accaggatcc tcgagttgca   300
gcacatgtca taagtgaggc cagcagtagc acagcgtctg ttctccagtg gccccccaaa   360
ggctactaca ccataagcag caacttggtg accctcgaga cgggaagca gctggccgtt   420 aaaagacaag gactctatta tatctacgcc caagtcacct tctgttccaa tcgggaagct   480
tcgagtcaag ctccgttcat agccagcctc tgcctgcatt ccccgagtgg atccgagaga   540
gtcttactca gagctgcaaa tgcccgcagt tcctccaaac cctgtgggca gcaatccatt   600
cacttgggag gagtcttcga actgcatcca ggtgcttcgg tgttcgtgaa cgtgactgat   660
ccgagccaag tgagccacgg gacgggcttc acgtcttttg gcttactcaa actctgaa     718
```

<210> SEQ ID NO 15
<211> LENGTH: 22
<212> TYPE: PRT
<213> ORGANISM: Homo sapiens
<220> FEATURE:
<223> OTHER INFORMATION: Residues 1-22 of intracellular domain of human
      CD154

<400> SEQUENCE: 15

```
Met Ile Glu Thr Tyr Asn Gln Thr Ser Pro Arg Ser Ala Ala Thr Gly
1               5                   10                  15

Leu Pro Ile Ser Met Lys
            20
```

<210> SEQ ID NO 16
<211> LENGTH: 66
<212> TYPE: DNA
<213> ORGANISM: Homo sapiens
<220> FEATURE:
<223> OTHER INFORMATION: DNA sequence corresponding to residues 1-22 of
      intracellular domain of human CD154

<400> SEQUENCE: 16

```
atgatcgaaa catacaacca aacttctccc cgatctgcgg ccactggact gcccatcagc    60
atgaaa                                                                66
```

<210> SEQ ID NO 17
<211> LENGTH: 78
<212> TYPE: DNA
<213> ORGANISM: Homo sapiens
<220> FEATURE:
<223> OTHER INFORMATION: DNA sequence corresponding to residues 127-198
      of transmembrane domain of human CD154

```
<400> SEQUENCE: 17
ggcggcattt ttatgtattt acttactgtt tttcttatca cccagatgat tgggtcagca    60 cttttttgctg tgtatctt                                                 78

<210> SEQ ID NO 18
<211> LENGTH: 24
<212> TYPE: PRT
<213> ORGANISM: Homo sapiens
<220> FEATURE:
<223> OTHER INFORMATION: Residues 127-198 of transmembrane domain of
      human CD154

<400> SEQUENCE: 18

Ile Phe Met Tyr Leu Leu Thr Val Phe Leu Ile Thr Gln Met Ile Gly
1               5                   10                  15

Ser Ala Leu Phe Ala Val Tyr Leu
            20

<210> SEQ ID NO 19
<211> LENGTH: 27
<212> TYPE: PRT
<213> ORGANISM: Homo sapiens
<220> FEATURE:
<223> OTHER INFORMATION: Transmembrane domain from human OX40 Ligand

<400> SEQUENCE: 19

Leu Leu Leu Val Ala Ser Val Ile Gln Gly Leu Gly Leu Leu Leu Cys
1               5                   10                  15

Phe Thr Tyr Ile Cys Leu His Phe Ser Ala Leu
            20                  25

<210> SEQ ID NO 20
<211> LENGTH: 81
<212> TYPE: DNA
<213> ORGANISM: Homo sapiens
<220> FEATURE:
<223> OTHER INFORMATION: Transmembrane domain from human OX40 Ligand

<400> SEQUENCE: 20
ctattgctgg tggcctctgt aattcaggga ctggggctgc tcctgtgctt cacctacatc    60
tgcctgcact ctctgctct t                                               81

<210> SEQ ID NO 21
<211> LENGTH: 20
<212> TYPE: PRT
<213> ORGANISM: Homo sapiens
<220> FEATURE:
<223> OTHER INFORMATION: Transmembrane domain from human CD70

<400> SEQUENCE: 21

Leu Arg Ala Ala Leu Val Pro Leu Val Ala Gly Leu Val Ile Cys Leu
1               5                   10                  15

Val Val Cys Ile
            20

<210> SEQ ID NO 22
<211> LENGTH: 60
<212> TYPE: DNA
<213> ORGANISM: Homo sapiens
<220> FEATURE:
<223> OTHER INFORMATION: Transmembrane domain from human CD70
      (corresponding to aa 18-38)
```

<400> SEQUENCE: 22
ctgcgggctg ctttggtccc attggtcgcg ggcttggtga tctgcctcgt ggtgtgcatc    60

<210> SEQ ID NO 23
<211> LENGTH: 99
<212> TYPE: DNA
<213> ORGANISM: Artificial Sequence
<220> FEATURE:
<223> OTHER INFORMATION: isoleucine-zipper modified from Saccharomyces
      cerevisiae

<400> SEQUENCE: 23
agaatgaagc agatcgagga caagatcgag gagatcctga gcaagatcta ccacatcgag    60
aacgagatcg ccagaatcaa gaagctgatc ggcgagaga                          99

<210> SEQ ID NO 24
<211> LENGTH: 214
<212> TYPE: PRT
<213> ORGANISM: Homo sapiens
<220> FEATURE:
<223> OTHER INFORMATION: Extracellular domain of human CD154

<400> SEQUENCE: 24

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
        35                  40                  45

Val Lys Asp Ile Met Leu Asn Lys Glu Glu Thr Lys Lys Glu Asn Ser
    50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
        115                 120                 125

Val Thr Phe Cys Ser Asn Arg Glu Ala Ser Ser Gln Ala Pro Phe Ile
    130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Leu Gln Pro Gly Ala Ser Val Phe Val
            180                 185                 190

Asn Val Thr Asp Pro Ser Gln Val Ser His Gly Thr Gly Phe Thr Ser
        195                 200                 205

Phe Gly Leu Leu Lys Leu
    210

<210> SEQ ID NO 25
<211> LENGTH: 23
<212> TYPE: PRT
<213> ORGANISM: Homo sapiens
<220> FEATURE:
<223> OTHER INFORMATION: Transmembrane domain of human CD154

<400> SEQUENCE: 25

Ile Phe Met Tyr Leu Leu Thr Phe Leu Ile Thr Gln Met Ile Gly Ser
1               5                   10                  15

Ala Leu Phe Ala Val Tyr Leu
            20

<210> SEQ ID NO 26
<211> LENGTH: 261
<212> TYPE: PRT
<213> ORGANISM: Artificial sequence
<220> FEATURE:
<223> OTHER INFORMATION: CD40L from Homo sapiens with changes at aa 114,
      115, 117-120

<400> SEQUENCE: 26

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Pro Arg Gly Glu Glu Asp Ser Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 27
<211> LENGTH: 281
<212> TYPE: PRT
<213> ORGANISM: Artificial sequence
<220> FEATURE:
<223> OTHER INFORMATION: TMZ-CD154 comprising sequences from Equus
      caballus and Saccharomyces cerevisae, and modified and synthezised
      sequences

```
<400> SEQUENCE: 27

Ala Thr Met Arg Met Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly Gly Arg Gly Gly Ile Phe Met Tyr Leu Leu
        35                  40                  45

Thr Val Phe Leu Ile Thr Gln Met Ile Val Ser Ala Leu Phe Ala Val
    50                  55                  60

Tyr Leu His Arg Arg Leu Asp Lys Ile Glu Asp Glu Arg Asn Leu His
65                  70                  75                  80

Glu Asp Phe Val Phe Met Lys Thr Ile Gln Arg Cys Asn Lys Gly Glu
                85                  90                  95

Gly Pro Leu Ser Leu Leu Asn Cys Glu Glu Ile Arg Ser Gln Phe Glu
            100                 105                 110

Gly Phe Val Lys Asp Ile Met Leu Asn Glu Glu Val Lys Lys Lys Gly
        115                 120                 125

Glu Asn Phe Glu Met Gln Lys Gly Asp Gln Glu Pro Gln Ile Ala Ala
130                 135                 140

His Val Ile Ser Glu Ala Ser Ser Lys Thr Ala Ser Val Leu Gln Trp
145                 150                 155                 160

Ala Gln Lys Gly Tyr Tyr Thr Ile Ser Asn Asn Leu Val Thr Leu Glu
                165                 170                 175

Asn Gly Lys Gln Leu Ala Val Lys Arg Gln Gly Leu Tyr Tyr Ile Tyr
            180                 185                 190

Ala Gln Val Thr Phe Cys Ser Asn Arg Glu Ala Ser Gly Gln Ala Pro
        195                 200                 205

Phe Ile Ala Ser Leu Cys Leu Arg Ser Val Ser Gly Ser Glu Arg Ile
210                 215                 220

Leu Leu Arg Ala Ala Asn Thr His Ser Ser Lys Pro Cys Gly Gln
225                 230                 235                 240

Gln Ser Ile His Leu Gly Gly Val Phe Glu Leu Gln Pro Gly Ala Ser
                245                 250                 255

Val Phe Val Asn Val Thr Asp Pro Ser Gln Val Ser His Gly Thr Gly
            260                 265                 270

Phe Thr Ser Phe Gly Leu Leu Lys Leu
        275                 280

<210> SEQ ID NO 28
<211> LENGTH: 280
<212> TYPE: PRT
<213> ORGANISM: Artificial sequence
<220> FEATURE:
<223> OTHER INFORMATION: TMZ-CD154 comprising sequences from Canis lupus
      familiaris and Saccharomyces cerevisae, and modified and
      synthezised sequences

<400> SEQUENCE: 28

Ala Thr Met Arg Met Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly Gly Arg Gly Gly Ile Phe Met Tyr Leu Leu
        35                  40                  45

Thr Val Phe Leu Ile Thr Gln Met Ile Gly Ser Ala Leu Phe Ala Val
```

```
                 50                  55                  60
Tyr Leu His Arg Arg Leu Asp Lys Ile Glu Asp Glu Arg Asn Leu Tyr
 65                  70                  75                  80

Glu Asp Phe Val Phe Met Lys Thr Leu Gln Lys Cys Asn Lys Gly Glu
                     85                  90                  95

Gly Ser Leu Ser Leu Leu Asn Cys Glu Glu Ile Lys Ser Gln Phe Glu
                100                 105                 110

Ala Phe Leu Lys Glu Ile Met Leu Asn Asn Glu Met Lys Lys Glu Glu
            115                 120                 125

Asn Ile Ala Met Gln Lys Gly Asp Gln Asp Pro Arg Ile Ala Ala His
130                 135                 140

Val Ile Ser Glu Ala Ser Ser Asn Pro Ala Ser Val Leu Arg Trp Ala
145                 150                 155                 160

Pro Lys Gly Tyr Tyr Thr Ile Ser Ser Asn Leu Val Ser Leu Glu Asn
                165                 170                 175

Gly Lys Gln Leu Ala Val Lys Arg Gln Gly Leu Tyr Tyr Val Tyr Ala
                180                 185                 190

Gln Val Thr Phe Cys Ser Asn Arg Ala Ala Ser Ser Gln Ala Pro Phe
            195                 200                 205

Val Ala Ser Leu Cys Leu His Ser Pro Ser Gly Thr Glu Arg Val Leu
210                 215                 220

Leu Arg Ala Ala Ser Ser Arg Gly Ser Ser Lys Pro Cys Gly Gln Gln
225                 230                 235                 240

Ser Ile His Leu Gly Gly Val Phe Glu Leu His Pro Gly Ala Ser Val
                245                 250                 255

Phe Val Asn Val Thr Asp Pro Ser Gln Val Ser His Gly Thr Gly Phe
                260                 265                 270

Thr Ser Phe Gly Leu Leu Lys Leu
                275                 280

<210> SEQ ID NO 29
<211> LENGTH: 280
<212> TYPE: PRT
<213> ORGANISM: Artificial sequence
<220> FEATURE:
<223> OTHER INFORMATION: TMZ-CD154 comprising sequences from Felis catus
      and Saccharomyces cerevisae, and modified and synthezised
      sequences

<400> SEQUENCE: 29

Ala Thr Met Arg Met Lys Gln Ile Glu Asp Lys Ile Glu Glu Ile Leu
 1               5                  10                  15

Ser Lys Ile Tyr His Ile Glu Asn Glu Ile Ala Arg Ile Lys Lys Leu
                20                  25                  30

Ile Gly Glu Arg Gly Gly Arg Gly Gly Gly Ile Phe Met Tyr Leu Leu
            35                  40                  45

Thr Val Phe Leu Ile Thr Gln Met Ile Gly Ser Ala Leu Phe Ala Val
 50                  55                  60

Tyr Leu His Arg Arg Leu Asp Lys Ile Glu Asp Glu Arg Asn Leu Tyr
 65                  70                  75                  80

Glu Asp Phe Val Phe Met Lys Thr Leu Gln Lys Cys Asn Lys Gly Glu
                     85                  90                  95

Gly Ala Leu Ser Leu Leu Asn Cys Glu Glu Ile Lys Ser Arg Phe Glu
                100                 105                 110

Ala Phe Leu Lys Glu Ile Met Leu Asn Lys Glu Thr Lys Lys Glu Lys
            115                 120                 125
```

```
Asn Val Ala Met Gln Lys Gly Asp Gln Asp Pro Arg Val Ala Ala His
    130                 135                 140

Val Ile Ser Glu Ala Ser Ser Thr Ala Ser Val Leu Gln Trp Ala
145                 150                 155                 160

Pro Lys Gly Tyr Tyr Thr Ile Ser Ser Asn Leu Val Thr Leu Glu Asn
                165                 170                 175

Gly Lys Gln Leu Ala Val Lys Arg Gln Gly Leu Tyr Tyr Ile Tyr Ala
                180                 185                 190

Gln Val Thr Phe Cys Ser Asn Arg Glu Ala Ser Ser Gln Ala Pro Phe
        195                 200                 205

Ile Ala Ser Leu Cys Leu His Ser Pro Ser Gly Ser Glu Arg Val Leu
    210                 215                 220

Leu Arg Ala Ala Asn Ala Arg Ser Ser Ser Lys Pro Cys Gly Gln Gln
225                 230                 235                 240

Ser Ile His Leu Gly Gly Val Phe Glu Leu His Pro Gly Ala Ser Val
                245                 250                 255

Phe Val Asn Val Thr Asp Pro Ser Gln Val Ser His Gly Thr Gly Phe
                260                 265                 270

Thr Ser Phe Gly Leu Leu Lys Leu
        275                 280
```

MEDICAL AGENTS AND USES THEREOF

FIELD OF INVENTION

The present invention relates to a novel compound TMZ-CD154 and a method to treat diseases in which the novel molecule TMZ-CD154 is used. In particular, TMZ-CD154 is used to modify the immune responses in patients with immune related diseases such as cancer and infectious disease. The present invention also relates to a method to activate cells with the TMZ-CD154 in vitro either prior to using the activated cells for therapy or for diagnostic purposes.

BACKGROUND OF THE INVENTION

During the last decades gene transfer technology has been under extensive investigation in treatment of e.g. cancer. In 2012, Glybera became the first gene therapy treatment approved for clinical use. Glybera compensates for lipoprotein lipase deficiency by delivering an intact copy of the human lipoprotein lipase (LPL) gene incorporated into the adeno-associated virus serotype 1 (AAV1) viral vector.

The aim of gene therapy is to introduce a functional/therapeutic gene into a target cell such as a tumor cell.

WO 2012/038607 describes a method of producing CD40L in a cell and increasing tumor specific immune response and apoptosis in a subject. CD40L (also denoted CD40 ligand, CD154 or gp39) is a type II transmembrane protein belonging to the tumor necrosis factor family.

WO 02/36769 describes a CD40L-CD40 chimera. In contrast to the nucleotide sequence of the present invention the chimera contains an intracellular signaling region of another protein while the present invention lacks intracellular signaling capacity.

Blaser et al (Clin. Immunology 2005, 117, 231-237) and Hsu et al. (Journal of Biological Chemistry, 1997, 272, 911-915) describe naturally occurring CD40L that in the case of Blaser et al. demonstrates that a mutation leads to a dysfunctional protein. Hsu et al. describes that naturally CD40L can be cleaved to release the extracellular domain. However, released CD40L is not stable as a trimer.

WO 94/10308 and WO 2007/120368 refer to soluble multimeric CD40L molecules that are not retained in the plasma membrane, but released from the cell or used as recombinant produced molecules for systemic use in patient. A comparison of these soluble molecules with TMZ-CD154 of the present invention shows that TMZ-CD154 gives a stronger activation signal, likely because it is retained in the plasma membrane.

CD154 is a transmembrane molecule that may trimerize upon binding to the CD40 receptor. Binding leads to reciprocal stimulation of the CD154 positive and the CD40 positive cells. CD154 may also be cleaved and secreted but is then acting as a soluble CD154 (sCD154) monomer. Membrane-bound or sCD154 activates dendritic cells (DCs) to become efficient antigen-presenting cells and activate so called Th1 type of immune responses with effector cells such as T cells and natural killer (NK) cells. The Th1 type immune response plays a crucial role in tumor immunity and is, hence, the essence of active tumor immunotherapy. CD154 can induce apoptosis in CD40 positive tumor cells by means not fully established. However, some reports claim that it is due to the TRAF3-JNK pathway dependent caspase-9 activation while others studies implicate an auto- or paracrine production of death ligands that may induce caspase-8 activation (Loskog and Eliopoulos, Semin Immunol 2009). CD40 has no death domains in its tail leaving room for multiple explanations. The apoptosis induction has shown more potent if CD154 is membrane-bound which may be because of the trimerization of this receptor/ligand system upon binding. CD154 has been used as a soluble molecule in clinical trials enrolling patients with cancer, but systemic exposure may result in increased liver enzymes which has not been noted when CD154 has been delivered locally in a tumor metastases for example via using adenoviral serotype 5 gene transfer (Vonderheide JCO, 2001; Malmström et al CCR 2010). The full length CD154 has been used in oncolytic viruses as well (Fernandes et al CCR 2009; Gomes et al CCR 2009; Terada et al GT 2006; Diaconu et al CR 2012) and tested for safety in patients (Pesonen et al CR 2012). The CD154 molecule expressed in T cells by genetic engineering can result in lymphoproliferative disease (Brown et al Nat Med 1998). Hence, vectors transferring the full-length CD154 gene and that have the capacity to infect cells that may react in such manner may cause unexpected adverse toxicity.

Hence, there is a need for developing a CD154 derivative, which maintains the beneficial properties with respect to apoptosis and tumor suppression, but which is without undesired adverse toxicity.

BRIEF DESCRIPTION OF THE INVENTION

The present inventor has developed a membrane-bound, trimerized CD154 derivative lacking the intracellular signaling domains. The derivative is a stronger immunomodulator than the corresponding monomer CD154, it will not give rise to internal CD154 signaling, and it will not give rise to systemic CD154-mediated toxicity.

Description of TMZ-CD154

This invention relates to an engineered form of CD154 in which the extracellular and transmembrane domain of CD154 is fused to an oligomerization domain (FIG. 1). The engineered CD154 will retain a membrane-bound form with a functional extracellular domain but will not contain intracellular signaling domains. Instead, the oligomerization domain will oligomerize the translated engineered CD154 and the protein complex will remain membrane-bound.

As an example, we have produced a trimerized membrane-bound isoleucine zipper-containing CD154 molecule named TMZ-CD154. TMZ-CD154 form oligomerized, preferably trimerized, molecules of CD154 lacking the intracellular domain and it is localized on the cell membrane. TMZ-CD154 expressed in cells results in robust detection of the molecule on the cell surface and minimum secretion of the molecule comparable to wild type CD154. TMZ-CD154-expressing cells activate dendritic cells (DCs) as shown by a uniform CD83 expression and high IL12 production. IL12 production is as high as wild type CD154 and higher than if the DCs are stimulated with soluble multimeric CD154 molecules demonstrating the benefit of a transmembrane region that retains TMZ-CD154 in the membrane. Further, CD154 signaling in CD154-expressing cells upon CD40 ligation is poorly defined but may induce a proliferative condition in CD154-expressing T cells. Hence, TMZ-CD154 will have the beneficial properties of CD154 stimulation of CD40 positive cells without activation of downstream signaling pathways within the TMZ-CD154-expressing cells that may cause uncontrolled growth in for example engineered T cells or other unknown events dependent on the engineered cell type. This is important especially if the molecule is delivered to cells that may be affected by an internal CD154 signaling such as T cells.

As described herein, the present invention is not limited to TMZ-CD154, but other nucleotides/proteins having the essential building blocks are also within the scope of the invention. For illustrative purposes TMZ-CD154 is used as an example of the various aspects of the invention:
i) TMZ-CD154 in nucleotide or protein form,
ii) TMZ-CD154 for use in medicine,
iii) TMZ-CD154 inserted into genetic vehicles, cells, artificial cells or natural or artificial vehicles,
iv) TMZ-CD154 inserted into genetic vehicles, cells, artificial cells or natural or artificial vehicles for use in medicine,
v) TMZ-CD154 or TMZ-CD154 inserted into genetic vehicles, cells, artificial cells or natural or artificial vehicles for use in treating diseases including, but not limited to, cancer, infectious disease, lymphoproliferative disease, inflammation, chronic inflammation, autoimmunity or allergy within human and/or veterinarian medicine,
vi) a pharmaceutical composition comprising TMZ-CD154,
vii) a pharmaceutical composition comprising TMZ-CD154 inserted into genetic vehicles, cells, artificial cells or natural or artificial vehicles,
viii) a method for producing TMZ-CD154 in a cell.

DESCRIPTION OF THE INVENTION

Based on the observations reported herein, especially in view of the results concerning TMZ-CD154, the present invention relates to a nucleotide sequence comprising the structure OD-(L)-TD-ED(5' to 3')

wherein OD is an oligomerization domain,
L is a linker, which optionally is present,
TD is a transmembrane domain, and
ED is an extracellular domain of CD154,
with the proviso that the nucleotide sequence does not comprise the intracellular CD154 region corresponding to equivalent nucleotide sequence of SEQ ID NO: 16.

The transmembrane domain may be derived from CD154 or from any type II transmembrane protein.

The extracellular domain may be selected from
i) SEQ ID NO: 11, i.e. residues 199-846 of SEQ ID NO: 1,
ii) SEQ ID NO: 11, i.e. residues 199-846 of SEQ ID NO: 1, but wherein one or more of the nucleic acid residues 397-420 of SEQ ID NO: 1 have been deleted or exchanged with another nucleic acid to avoid cleavage of the molecule,
iii) SEQ ID NO 12, i.e. residues 127-846 of SEQ ID NO: 3,
iv) SEQ ID NO: 13, i.e. residues 127-844 of SEQ ID NO: 4,
v) SEQ ID NO: 14, i.e. residues 127-844 of SEQ ID NO: 5,
vi) a nucleotide sequence having at least 95%, 98% or 99% sequence identity with a sequence defined in any of i)-v), or
vi) a corresponding extracellular CD154 domain from a mammal.

The nucleotide sequence of the present invention contains three mandatory elements, which from the 5' end to the 3' gives the structure OD-TD-ED, and at the same time it lacks intracellular signaling. The extracellular domain of CD40L shall be fused to a transmembrane region to retain it on the cell surface for enhancing signaling and a trimerization domain for maximal signaling. A linker may be inserted between OD and TD.

The intent of TMZ-CD154 is to trimerize CD40L and retain it in the plasma membrane without conferring intracellular signaling in the TMZ-CD154 carrying cell upon interaction with CD40+ cells. The purpose is to transmit signals, but not to achieve reciprocal signals.

Naturally occurring CD40L does not keep a trimerized structure in vivo in a solid manner, which weakens signaling.

A nucleotide sequence according to the present invention can be used in in vivo gene therapy for example—and as described in the examples herein—by intratumoral injection of a virus carrying the nucleotide sequence (eg TMZ-CD154 gene) it is important to remove the intracellular region (eg of CD40L). In vivo injection will lead to expression of the nucleotide sequence in all infected cells including tumor-infiltrating T cells, cell that can naturally express CD40L, under a short time during activation. Overexpression of wild type CD40L in T cell leads to uncontrolled T cell proliferation and, hence, lymphoproliferative diseases in mice. Removing the intracellular region is important for safety aspects. TMZ-CD154 does not induce uncontrolled T cell proliferation in human T cells nor such adverse reactions that have been noted in CD40L-treated mice.

In particular, the invention relates to a CD40L or CD154 derivative that has the following structure:

OD-(L)-TD-ED, wherein OD is an oligomerization domain, L is a linker, which optionally is present, TD the transmembrane domain and ED is the extracellular domain. Thus, compared with CD40L (CD154), the nucleotide sequence of the invention does not have an intracellular domain, but has a oligomerization domain, which precedes the transmembrane and the extracellular domains. Thus, the intracellular domain of CD40L (CD154) is not present.

In the table below is given an overview of the sequences mentioned herein.

SEQUENCE LISTING

| SEQ ID NO: | | |
|---|---|---|
| 1 | TMZ-CD154 | Nucleotide |
| 2 | TMZ-CD154 | Protein |
| 3 | TMZ-CD154 (horse) | Nucleotide |
| 4 | TMZ-CD154 (dog) | Nucleotide |
| 5 | TMZ-CD154 (cat) | Nucleotide |
| 6 | TMZ-CD154/4-1BBL gene | Nucleotide |
| 7 | TMZ-CD154/4-1BBL gene | Protein |
| 8 | TMZ-CD154/aIL6R scFv gene | Nucleotide |
| 9 | TMZ-CD154/aIL6R scFv gene | Protein |
| 10 | CD154 wild type full length | Protein |
| 11 | ED -Residues 199-846 of SEQ ID NO: 1 | Nucleotide |
| 12 | ED -Residues 127-846 of SEQ ID NO: 3 | Nucleotide |
| 13 | ED - Residues 127-844 of SEQ ID NO: 4 | Nucleotide |
| 14 | ED -Residues 127-844 of SEQ ID NO: 5 | Nucleotide |
| 15 | ID Residues 1-22 of SEQ ID 10 | Protein |
| 16 | ID Corresponding to amino acid residues 1-22 of SEQ ID 10 | Nucleotide |
| 17 | TD Residues 127-198 of SEQ ID NO: 1 | Nucleotide |
| 18 | TD Corresponding to nucleic acid residues 127-198 of SEQ ID NO: 1 | Protein |
| 19 | TD derived from human O x 40 ligand | Protein |
| 20 | TD derived from human O x 40 ligand | Nucleotide |
| 21 | TD derived from human CD70 | Protein |
| 22 | TD derived from human CD70 | Nucleotide |
| 23 | OD - isoleucine zipper-residues 10-108 SEQ ID NO: 1 | Nucleotide |

| SEQ ID NO: | | |
|---|---|---|
| 24 | ED - protein corresponding to SEQ ID NO: 11, i.e. residues 199-846 of SEQ ID NO: 1 | Protein |
| 25 | Linker - protein corresponding to SEQ ID NO: 17, i.e. residues 109-126 of SEQ ID NO: 1 | Protein |
| 26 | Human CD40L full length aa with shift in aa to prevent cleavage of the molecule Q K (nr 114, 115) and D Q N P (nr 117-120) are changed to P R and E E D S | Protein |
| 27 | TMZ-CD154 (horse) | Protein |
| 28 | TMZ-CD154 (dog) | Protein |
| 29 | TMZ-CD154 (cat) | Protein |

In general, the nucleotide sequence is a CD154 lacking the intracellular region and as it appears from the above, the CD154 may be derived from mammals including human, horse, dog, cat etc. Human CD154 is preferred. It is envisaged that one or more of residues of CD154 may be deleted or substituted. In the following table and illustrated with human CD154 (given as protein) is given an indication of which residues may be substituted with another residue. Any combination of substitution/deletion pattern is within the scope of the present application. Thus, one or more of the amino acids of CD154 (lacking the intracellular region) indicated in the table below may be substituted/deleted according to the specific change stated.

Some of the amino acids of CD154 (protein) may also be substituted in order to prevent cleavage of the molecule. SEQ ID NO: 26 gives an example of such a sequence, wherein the changes are as follows (based on the full length human CD150): Q114P, K115R, D117E, Q118E, N119D and P120S. A nucleotide sequence corresponding to the protein of SEQ ID NO: 26, but lacking the intracellular region is also within the scope of the present invention.

Natural Variations in the Human CD154 Amino Acid Sequence
Reference: UniProtKB/Swiss-Prot/P29965 (CD40L_HUMAN)

| Position (aa) | Change | Domain |
|---|---|---|
| 36 | M to R | TD |
| 38 | G to R | TD |
| 116 | G to R | ED |
| 116 | G to S | ED |
| 123 | A to E | ED |
| 125 | H to R | ED |
| 126 | V to A | ED |
| 126 | V to D | ED |
| 128-129 | SE to RG | ED |
| 140 | W to C | ED |
| 140 | W to G | ED |
| 140 | W to R | ED |
| 143 | K to T | ED |
| 144 | G to E | ED |
| 147 | T to N | ED |
| 155 | L to P | ED |
| 170 | Y to C | ED |
| 173 | A to D | ED |
| 174 | Q to R | ED |
| 176 | T to I | ED |
| 195 | L to P | ED |
| 208 | A to D | ED |
| 211 | T to N | ED |
| 219 | G to R | ED |
| 224 | H to Y | ED |
| 226 | G to A | ED |
| 227 | G to V | ED |
| 227 | Missing | ED |
| 231 | L to S | ED |
| 235 | A to P | ED |
| 237 | V to E | ED |
| 254 | T to M | ED |
| 257 | G to D | ED |
| 257 | G to S | ED |
| 258 | L to S | ED |

As mentioned above, the transmembrane domain may be any transmembrane protein, notably derived from CD154, human OX40 ligand or human CD70.

Thus, the transmembrane domain may have at least 90% sequence identity with
i) SEQ ID NO: 17, i.e. residues 127-198 of SEQ ID NO 1,
ii) SEQ ID NO: 20, i.e. transmembrane domain of human OX40, or
iii) SEQ ID NO: 22, i.e. transmembrane domain of human CD70,
or it may have at least 95%, 96%, 97%, 98%, 99% or 100% sequence identity with SEQ ID NO: 17, SEQ ID NO: 20 or SEQ ID NO: 22.

As an example, the transmembrane domain has SEQ ID NO: 17, i.e. the residues 127-198 of SEQ ID NO: 1 (TMZ-CD154).

The oligomerization domain is typically an isoleucine zipper or a trimerization domain of T4 fibritin. As an example, the oligomerization domain is the isoleucine zipper having SEQ ID NO: 23, i.e. residues 10-108 of SEQ ID NO: 1.

The nucleotide sequence may further comprise a Kozak sequence eg corresponding to residues 1-9 of SEQ ID NO: 1.

The Kozak sequence is a short nucleotide sequence that occurs on eukaryotic mRNA to enhance the initiation of the translation process. To enhance the translation of TMZ-CD154 when used in gene therapy settings, the TMZ-CD154 gene sequence is proceeded by a Kozak sequence. Kozak sequence will be present if TMZ-CD154 is expressed alone or as the first gene in a transcript containing additional genes for immunomodulators or other molecules. Thus, in the present context a nucleotide according to the present invention may or may not have a Kozak sequence. Both forms are within the scope of the present invention.

By way of example, a nucleotide sequence according to the invention may have at least 90% or at least 95% sequence identity with SEQ ID NO: 1, SEQ ID NO. 3, SEQ ID NO: 4 or SEQ ID NO: 5. Specifically, a nucleotide sequence according to the invention may have at least 98% sequence identity with SEQ ID NO: 1, SEQ ID NO. 3, SEQ ID NO: 4 or SEQ ID NO: 5, or being identical to the nucleotides of SEQ ID NO: 1, SEQ ID NO. 3, SEQ ID NO: 4 or SEQ ID NO: 5.

A nucleotide sequence according to the invention may also be combined with an immunomodulator. Examples of suitable immunomodulators are 4-1BB ligand gene, or a gene for an anti IL6R scFv.

Analogously, a nucleotide sequence according to the invention may be combined with a signaling pathway modulator such as an anti-IL6R scFv; or it may be combined w with a signaling pathway blocker. Thus, a nucleotide sequence according to the invention may have at least 95%, 98% or 100% sequence identity with SEQ ID NO: 6 or SEQ ID NO: 8 (TMZ-CD154/4-1BBL gene and TMZ-CD154/aIL6R scFv gene, respectively).

The use of a nucleotide sequence according to the invention is described in details herein. Overall the nucleotide sequence may be used in medicine and/or as a diagnostic tool.

The invention also relates to a protein encoded by a nucleotide sequence as defined herein.

In analogy with the definition of a nucleotide sequence according to the invention, a protein of the invention can be defined as a protein comprising the structure

OD-(L)-TD-ED, wherein OD is an amino acid sequence corresponding to an oligomerization domain,
L is a linker, which optionally is present,
TD is an amino acid sequence corresponding to a transmembrane domain, and
ED is an amino acid sequence corresponding to an extracellular domain of CD154,
with the proviso that the protein does not comprise an amino acid sequence corresponding to the intracellular CD154 region corresponding to the amino acid sequence SEQ ID NO: 15.

The extracellular domain of CD154 may be selected from
i) SEQ ID NO: 24,
ii) SEQ ID NO: 24, but wherein one or more of the amino acids of the amino acid sequence MQKGDQNP corresponding to the nucleotide residues 397-420 of SEQ ID NO: have been deleted or exchanged with another amino acid to avoid cleavage of the molecule,
iii) amino acid residues corresponding to nucleotide residues of SEQ ID NO 12, i.e. residues 127-846 of SEQ ID NO: 3,
iv) amino acid residues corresponding to the nucleotide residues of SEQ ID NO: 13, i.e. residues 127-844 of SEQ ID NO: 4,
v) amino acid residues corresponding to the nucleotide residues of SEQ ID NO: 14, i.e. residues 127-844 of SEQ ID NO: 5,
vi) an amino acid sequence having at least 95%, 98% or 99% sequence identity with a sequence defined in any of i)-v), or
vi) a corresponding extracellular CD154 domain from a mammal.

The transmembrane domain may be derived from CD154 or any type II transmembrane protein. It may have a sequence identity of at least 90%, 95%, 98% or 100% with SEQ ID NO: 18, SEQ ID NO: 19 or SEQ ID NO: 21, preferably SEQ ID NO: 18.

The protein according to the invention lacks an intracellular region such as the intracellular region of CD154 or CD40.

The details and particulars described under the aspect of nucleotides apply also for the protein aspects, however, regarding the protein aspect, the relevant parts of the molecules are the amino acid sequences corresponding to the nucleotides describes or amino acid sequences encoded by the nucleotides described herein.

By way of example, a protein according to the invention may comprise an ED having at least 90% or at least 95% sequence identity to SEQ ID NO: 24. Moreover, in the table above is given a review of possible changes in ED. As described above, any such change and combination of changes are intended to be within the scope of the present invention.

More specifically, the oligomerization domain may be an isoleucine zipper domain or a trimerization domain of T4 fibritin.

As mentioned above, the transmembrane domain may be derived from transmembrane domain of CD154 or any type II transmembrane protein. Specifically, the amino acid sequence corresponding to the transmembrane domain has at least 90%, 95%, 98% or 100% sequence identity to SEQ ID NO: 18, SEQ ID NO: 19 (TD derived from OX40 ligand) or SEQ ID NO: 21 (TD derived from CD70). As an example, the transmembrane domain of a protein according to the invention may be SEQ ID NO: 18 or a protein, wherein one or more of the residues of SEQ ID NO: 18 may be deleted or substituted with another amino acid. Examples of such residues are aa14 and/or aa16, where eg M14R and/or G15R (corresponding to M36R and G38R in the full length CD154).

In particular, a protein according to the invention may have at least 90%, 95% or 98% sequence identity with SEQ ID NO: 2, such as 100% sequence identity with SEQ ID NO: 2.

The use of a protein according to the invention is described in details herein. Overall a protein may be used in medicine and/or as a diagnostic tool.

TMZ-CD154 is especially of interest both in nucleotide and protein form.

Details Regarding TMZ-CD154 Reference to Structure and Sequences

The TMZ-CD154 gene contains the extracellular and transmembrane domain of CD154 fused to an oligomerization domain but lacking the intracellular CD154 region. More specifically, the TMZ-CD154 gene has at least 90% sequence identity with one of SEQ ID NO: 1, SEQ ID NO: 3, SEQ ID NO: 4, or SEQ ID NO: 5. In particular the TMZCD154 gene has at least 95% sequence identity with one of SEQ ID NO: 1, SEQ ID NO: 3, SEQ ID NO: 4 or SEQ ID NO: 5. Notably, the TMZ-CD154 gene is one of SEQ ID NO: 1, SEQ ID NO: 3, SEQ ID NO: 4 or SEQ ID NO: 5.

SEQ ID NO. 2 corresponds to the amino acid sequence of SEQ ID NO: 1. Encompassed by the present invention is also the TMZ-CD154 protein having at least 90% sequence identity with the corresponding protein sequence of one of the nucleotide sequences of SEQ ID NO: 1, SEQ ID NO: 3, SEQ ID NO: 4, or SEQ ID NO: 5. In particular the TMZ-CD154 protein has at least 95% sequence identity with the corresponding protein sequence of one of the nucleotide sequences of SEQ ID NO: 1, SEQ ID NO: 3, SEQ ID NO: 4 or SEQ ID NO: 5. Notably, the TMZ-CD154 protein corresponds to the corresponding protein sequence of the nucleotide sequences SEQ ID NO: 1, SEQ ID NO: 3, SEQ ID NO: 4 or SEQ ID NO: 5. Notably, the protein has at least 90% or at least 95% sequence identity with the SEQ ID NO: 2. Notably, the TMZ-CD154 protein has the protein sequence of SEQ ID NO: 2.

The TMZ-CD154 domains may be of human origin, but can also be originating from other species including, but not limited to, dog, cat, and horse. The transgene can be used in autologous, allogeneic or xenogeneic form. For example, human TMZ-CD154 can be used to treat diseases in humans, cat, dog and/or horse.

The oligomerization domain may be an isoleucine zipper domain but may also be other domains that oligomerize the TMZ-CD154 molecule without disturbing the membrane localization. Many proteins oligomerize or specifically trimerize and contain sequences that can be used. For example, the trimerization domain of T4 fibritin or other molecules that naturally trimerize may be used.

The transmembrane domain can be derived from the CD154 molecule or from other molecules that exhibit one or more transmembrane region/s, or a designed region to potentiate the retention of CD154 in the membrane. Transmembrane regions can be single or multiple transmembrane alpha helices, beta barrel/s, a beta-helix of gramicidin A but also be other structures.

Vehicles

The invention also relates to a vehicle comprising a nucleotide sequence as defined herein. The vehicle may be any suitable vehicle including plasmids, viral vectors, transposons, cells, artificial cells, and artificial vehicles.

When TMZ-CD154 is used in the following it encompasses TMZ-CD154 as such as well as the other nucleotides (and proteins, if relevant) according to the present invention.

The vehicle for TMZ-CD154 transfer can be, but is not limited to, a plasmid, a replication deficient viral vector, a replication competent virus, a transposon, a cell, an artificial cell or an artificial vehicle.

TMZ-CD154 as defined herein may be delivered into vehicles described herein as a DNA, cDNA, RNA, mRNA, nucleotide oligo, or a protein.

Plasmids

The vehicle for the nucleotide sequences according to the present invention, notably TMZ-CD154, transfer can be a plasmid, a minicircle plasmid derivative or a self-replicating plasmid or minicircle.

The plasmid vector may be, but is not limited to, a basic plasmid consisting of a circular DNA sequence with sites of ORI, restriction enzyme/s, promoter/s and nucleotide sequence according to the invention, notably the TMZ-CD154 sequence, with start and stop codons.

The plasmid may also be a so called minicircle plasmid derivative with limited or no prokaryotic vector parts but containing the nucleotide sequence according to the present invention, notably the TMZ-CD154 sequence.

The plasmid containing the nucleotide according to the invention, notably the TMZ-CD154 sequence, may be a so called self-replicating plasmid or minicircle containing a S/MAR-Element or other part that enables self-replication of the plasmid or minicircle in cells.

Viral Vectors

The vector may be a replication-deficient viral vector or a replication-competent virus containing the nucleotide sequence according to the invention, for example TMZ-CD154.

With replication-deficient viral vector we mean a virus that is not capable to replicate by its own means because of deletion of genes involved in viral replication. For example, the early gene 1 (E1) can be deleted from the Adenoviridae family of viruses to generate a replication-deficient viral vector. To support the growth of a replication virus, the missing genes/related proteins need to be provided by, but not limited to, an E1 gene insert in the producer cell line (such as the 293, 293T, 911, C6 (Crucell) producer cell lines). The missing genes/related proteins can also be provided separately to a virus producing cell line. For example, the plasmid of a replication-deficient vector originating from the Retroviridae can be transfected together with genes/proteins containing the missing genes into producer cells.

With replication-competent virus we mean a virus that is capable of replicating by its own means in any cell that it infects or in cells of a specific origin. The latter can be a conditionally replicative virus in which the replication is driven by a promoter that is only active in certain cells or under certain circumstances. Such a cell can be a tumor cell or an organ-specific cell and such a circumstance can be upregulated promoter activity due to proliferation such as the Telomerase promoter (TERT) or a disrupted retinoblastoma Rb pathway.

The replication-deficient viral vector or the replication-competent virus, as stated in above, may have other deletions in the virus genome to render more space for transgenes such as TMZ-CD154 or to remove gene segments that otherwise compromise the treatment effect or the expression of the transgene. For example, the Early gene 3 (E3) can be partially or completely deleted from the Adenoviridae family of viruses for the above mentioned reasons.

The replication-deficient viral vector or the replication-competent virus, as stated in above, may have additions of promoters to drive replication or transgene expression, and insulators or similar to shield the promoter or transgene from inhibiting actions, to enhance transgene translation, or to increase or enhance the specificity the oncolytic function of an oncolytic virus. For example, the viral vectors can contain promoters derived from, but not limited to, Cytomegalovirus (CMV), Rous sarcoma virus (RSV), Murine stem cell virus (MSCV), and/or the human elongation factor-1a (EF-1a) promoter.

The replication-deficient viral vector or replication-competent viruses as described above, may be, but is not limited to, a member of the viral families Adenoviridae, Papovaviridae, Parvoviridae, Herpesviridae, Poxviridae, Hepadnaviridae, Anelloviridae, Retroviridae, Reoviridae, Picornaviridae, Caliciviridae, Togaviridae, Arenaviridae, Flaviviridae, Orthomycoviridae, Paramyxoviridae, Bunyaviridae, Rhabdoviridae, Filoviridae, Coronaviridae, Astroviridae, Bornaviridae, Arteriviridae, Hepeviridae.

The replication-deficient viral vector or replication-competent viruses as described above, may be, but is not limited to, a member of the DNA viruses such as Adenoviridae, Papovaviridae, Parvoviridae, Herpesviridae, Poxviridae, Hepadnaviridae, Anelloviridae.

The replication-deficient viral vector or replication-competent viruses as described above may also be, but is not limited to, a member of the RNA viruses such as Retroviridae, Reoviridae, Picornaviridae, Caliciviridae, Togaviridae, Arenaviridae, Flaviviridae, Orthomycoviridae, Paramyxoviridae, Bunyaviridae, Rhabdoviridae, Filoviridae, Coronaviridae, Astroviridae, Bornaviridae, Arteriviridae, Hepeviridae.

The replication-deficient viral vector or replication-competent viruses as described above may be a member of the Adenoviridae, Parvoviridae, Poxviridae, Retroviridae, Togaviridae.

As exemplified in the Examples herein, a replication-deficient viral vector or replication-competent viruses as described herein is a member of the Adenoviridae family.

The replication-deficient viral vector or replication-competent viruses as described herein may be a chimeric virus. With chimeric virus we mean a virus as described in above composed of a) two or more different viral parts within a viral family described herein, b) two or more different viral parts from different viruses, or c) a mixture of "a" and "b" or d) a viral vector may have genes from other species. For example, a promoter derived from CMV virus can be inserted into a viral vector from another virus family, or a viral vector can exhibit human genes or promoters.

The replication-deficient viral vector or replication-competent viruses as described herein may be a chimeric virus as described above, especially a chimeric virus consisting of the Adenovirus serotype 5 backbone in which the fiber shaft and knob are derived from Adenovirus serotype 35.

Thus, a vehicle according to the invention may be a virus, which is an adenoviral serotype 5/35 virus. The adenoviral 5/35 virus may have an E2F promoter region/binding sites upstreams of the E1A gene, it may contain a Sp-1 site upstreams of the E1A gene, a E1A Δ24 deletion, E3 Δ6.7K/ gp19K, and the transgene cassette including the pCMV and transgene/s is inserted after the L5 gene region.

Transposons

The genetic vehicle may also be a transposon. With transposon we mean a vector derived from a transposable element (TE, transposon or retrotransposon). For example, but not limited to, the Sleeping Beauty transposon system or the PiggyBac transposon system.

Cells, Artificial Cells or Artificial Vehicles

The nucleotide sequence including TMZ-CD154 as defined herein can be inserted and displayed on cells, artificial cells or artificial vehicles. These cells/vehicles can be used as simple delivery vehicles of the nucleotide sequence or the translated protein, egTMZ-CD154, to a site of disease such as a tumor. If the cells are directly affected by the nucleotide sequences/translated protein, egTMZ-CD154, the cell vehicle may be used as both delivery of the nucleotide sequence/translated protein, egTMZ-CD154, and as a cell therapy due to the novel properties the cell exhibit because of the nucleotide sequence/translated protein, egTMZ-CD154.

The TMZ-CD154 engineered cells may be, but are not limited to be, tumor cells (e.g. tumor cell vaccines), cells of the immune system such as T cells, dendritic cells, monocytes and macrophages, and other cell types such as fibroblasts, mesenchymal stroma cells, endothelial cells, epithelial cells.

The TMZ-CD154 engineered cells may be tumor cells that are autologous or allogeneic to the patient. Such engineered cells may be used as a cellular vaccine in cancer patients.

The TMZ-CD154 engineered cells are autologous or allogeneic cells originating from the immune system as described herein to be used to treat patients. For example, the cells can be of lymphoid origin such as natural killer (NK cells) or antigen-targeting T cells generated by either selecting and expanding natural-occurring antigen-recognizing T cells or gene engineered T cells (e.g. T cells expressing chimeric antigen receptors, antigen-targeting T cell receptors or equivalent).

With "antigen" we mean a target to be recognized by the T cells via the T cell receptor, the chimeric antigen receptor or equivalent such as, but not limited to, a tumor-specific or associated antigen to treat cancer or a microbial antigen to treat infectious disease or cancer cells that also present microbial antigen. For example, Ebstein-Barr virus (EBV) may be expressed in cancers of B cell origin and therefore, EBV antigens can be used as a cancer cell target. Likewise, papilloma virus and CMV have been associated with cancer.

The nucleotide sequence, egTMZ-CD154, engineered cells can also be of myeloid origin such as, but not limited to, monocytes, dendritic cells and macrophages. These cells may be selected natural occurring cells, cells generated from progenitors ex vivo and/or gene engineered cells to achieve enhanced or novel properties. For example, the cells can be cultured with cytokines or other stimulators such as other cells, antigens, proteins, antibodies, peptides, nucleotides, RNA, DNA etc or engineered with gene vehicles to achieve novel properties.

The nucleotide sequence, eg TMZ-CD154, engineered cells may also be autologous or allogeneic cells other than tumor cells and immune cells such as, but not limited to, stem cells, fibroblasts, mesenchymal stromal cells, endothelial cells and epithelial cells. The cells may be natural occurring cells or generated by culturing of progenitors. The cells may have been ex vivo cultured and/or stimulated with cytokines or other stimulators such as other cells, antigens, proteins, antibodies, peptides, nucleotides, RNA, DNA etc. or engineered with gene vehicles to achieve novel properties.

The nucleotide sequence according to the invention, eg TMZ-CD154, can be displayed or delivered by artificial cells. With artificial cells we mean an entity that can have some important biological features of a certain cell function. It can be a vesicle enclosed in a lipid membrane, a plasma membrane or artificial membrane that 1) contain TMZ-CD154 as described herein to be transported and released at a disease site such as a tumor, 2) carries the nucleotide sequence of the invention, eg TMZ-CD154, on the membrane to activate CD40 positive cells at a site of disease or in vitro.

The nucleotide sequence according to the invention, eg TMZ-CD154, can also be displayed or delivered by natural or artificial vehicles. With natural or artificial vehicles we mean different compositions of liposomes, beads, nanoparticles or vesicles eg loaded with TMZ-CD154 on the surface or at an inner core for rapid or slow release of eg TMZ-CD154. Vesicles can be for example purified exosomes from the nucleotide sequence, eg TMZ-CD154, expressing cells.

Use of Genetic Vehicles Comprising a Nucleotide Sequence According to the Invention, Eg TMZ-CD154

Genetic vehicles, cells, artificial cells, natural or artificial vehicles engineered with a nucleotide sequence according to the invention, eg TMZ-CD154, as defined herein may be used for in vitro stimulation of cells that are then used as cell therapy or as stimulators for cells that will later be used for cell therapy. For example, TMZ-CD154 engineered dendritic cells pulsed with tumor or viral peptides may be used as a cell therapy for cancer or infectious disease.

Genetic vehicles, cells, artificial cells, artificial vehicles engineered with a nucleotide sequence, egTMZ-CD154, as defined herein may be used for in vitro stimulation of cells that are then used for cell therapy. For example, TMZ-CD154 engineered dendritic cells may be used for in vitro stimulation and expansion of tumor-, or virus-, targeting T cells prior to T cell therapy of cancer or infectious disease.

Moreover, the genetic vehicles, cells, artificial cells, artificial vehicles engineered with a nucleotide sequence, eg TMZ-CD154, as defined herein are used for in vitro stimulation of cells that are used for in vitro analyses of patients of healthy individuals. For example, TMZ-CD154 engineered dendritic cells may be used for in vitro expansion of tumor- or virus-specific T cells in order to evaluate the presence and function of such cell populations in blood or biopsies.

TMZ-CD154 and the other sequences as defined herein can be used as a therapeutic agent in the form of DNA, cDNA, RNA, mRNA, nucleotide oligo or a protein. In the following the uses are exemplified with TMZ-CD154 as an example, but the other nucleotides and proteins according to the present invention can also be employed to the described uses.

TMZ-CD154 for Use in Medicine

TMZ-CD154 can be used in medicine. Especially TMZ-CD154 can be used in the treatment of cancers.

TMZ-CD154 as defined herein can be used to treat cancer such as those originating from epithelial cells (carcinoma), connective tissue (sarcoma), germ cells (seminoma and dysgerminoma), precursor or embryonic cells (blastoma) or hematopoietic cells (lymphoma and leukemia).

TMZ-CD154 as defined herein may also be used to treat
i) non-hematopoetic cancers such as those originating from epithelial cells (carcinoma), connective tissue (sarcoma), germ cells (seminoma and dysgerminoma), precursor or embryonic cells (blastoma),
ii) cancers originating from epithelial cells (carcinoma) such as adenocarcinoma, squamous cell carcinoma, adenosquamous carcinoma, anaplastic carcinoma, large cell carcinoma or small cell carcinoma,
iii) carcinoma derived from cells in the pancreas such as, but not limited to, ductal adenocarcinoma,
iv) carcinoma derived from the ovaries such as ovarian carcinoma,
v) carcinoma derived from the urinary bladder,
vi) carcinoma derived from the lung,
vii) carcinoma derived from the liver,
viii) carcinoma derived from the kidney such as renal cell carcinoma,
ix) carcinoma derived from the colon,
x) carcinoma derived from the breast,
xi) carcinoma derived from the skin.
xii) neuroendocrine tumors, independently of their location,
xiii) cancer derived from the prostate,
xiv) cancer derived from the brain such as glioblastoma,
xv) cancers that originates from cells of mesenchymal origin such as those from bone, cartilage, fat, muscle and vascular or hematopoietic tissues (sarcoma),
xvi) sarcoma derived from bone such as osteosarcoma or cartilage such as chondrosarcoma,
xvii) sarcoma derived from fat such as liposarcoma or smooth muscle such as leiomyosarcoma,
xviii) soft tissue sarcoma including alveolar soft part sarcoma, angiosarcoma, cystosarcoma phyllodes, dermatofibrosarcoma protuberans, desmoid tumor, desmoplastic small round cell tumor, desmoplastic small round cell tumor, epitheloid sarcoma, extraskeletal chondrosarcoma, extraskeletal osteosarcoma, fibrosarcoma, hemangiopericytoma, hemangiosarcoma, Kaposi's sarcoma, leiomyosarcoma, lymphosarcoma, undifferentiated pleomorphic sarcoma, malignant peripheral nerve sheat tumor, neurofibrosarcoma, rhabdomyosarcoma, and synovial sarcoma,
xix) Ewing's sarcoma,
xx) hematopoetic cancers such as those originating from hematopoietic cells (lymphoma and leukemia),
xxi) hematopoetic cancers such as those originating from hematopoietic cells of the lymphoid linage such as, but not limited to, Hodgkin's or non-Hodgkin's lymphoma, or T cell lymphoma,
xxii) hematopoetic cancers such as those originating from hematopoietic cells of the lymphoid linage such as, but not limited to, non-Hodgkin's lymphoma,
xxiii) hematopoetic cancers such as those originating from hematopoietic cells of the lymphoid linage such as, but not limited to, B cell leukemia such as chronic myeloid leukemia and precursor B cell acute lymphoblastic leukemia,
xxiv) hematopoetic cancers such as those originating from hematopoietic cells of the myeloid linage such as, but not limited to, acute myeloid leukemia or chronic myeloid leukemia,
xxv) cancer with unknown primary location,
xxvi) local primary cancer,
xxvii) locally advanced cancer,
xxviii) single metastases,
xxix) spread disseminated cancer disease.
xxx) infectious disease,
xxxi) viral infections such as, but not limited to, cytomegalovirus (CMV) infection, Epstein-Barr virus (EBV) infection or adenoviral infection,
xxxii) viral infections such as, but not limited to, human immunodeficiency virus (HIV) infection,
xxxiii) viral infections such as, but not limited to, influenza virus, or RS virus,
xxxiv) lymphoproliferative disorders such as, but not limited to, Waldenström's macroglobulinemia.
xxxv) immune dysfunctions such as Hyper IgM syndrome,
xxxvi) immune dysfunctions where the ongoing immune reactions need to be tilted to Th1 type of immunity,
xxxvii) the diseases as defined herein in human medicine,
xxxviii) the diseases as defined herein in human adult patients,
xxxix) the diseases as defined herein in human pediatric patients,
xxxx) treat the diseases as defined herein in veterinarian medicine,
xxxxi) the diseases as defined herein in dogs,
xxxxii) the diseases as defined herein in cats.
xxxxiii) the diseases as defined herein in horses.

Use of TMZ-CD154 in Combination with Immunomodulators

TMZ-CD154 as defined herein can be combined with one or more other active molecules. The molecules can be used without or with the same or different vector systems.

Suitable active molecules are mentioned in the following.

The active molecules may be other immunomodulatory genes in the form of DNA, cDNA, RNA, mRNA, nucleotides, or protein. The other active agent may be one or more wild type immunomodulators such as, e.g., wild type immunomodulators belonging to the tumor necrosis factor (TNF)/tumor necrosis factor receptor (TNFR) super family.

TMZ-CD154 as defined herein may also be used combined with wild type 4-1BB ligand, and/or combined with wild type cytokine or cytokine receptors.

Additionally or alternatively, TMZ-CD154 as defined herein may be combined with one or more interleukines. The interleukines may be interleukin-2, 7, 15 and/or 21. Thus, the active agent to be combined with TMZ-CD154 as defined herein may be interleukin-2, interleukin-7, interleukin-15 or interleukin-21.

TMZ-CD154 as defined herein may also be combined with one or more wild type growth factors or one or more growth factor receptors. Such receptors may be wild type transforming growth factor-beta (TGFb) receptor, TGFb receptor decoy, or dominant negative TGFb receptor.

TMZ-CD154 as defined herein may also be combined with molecules as defined above, but which are modified from the wild type format. For example, the nucleotides or amino acids may have been altered but they still exhibit the same or improved immunostimulatory function, or the molecule may have been altered and/or fused with other domains creating chimeric proteins. For example, 4-1BB ligand extracellular domain and transmembrane domain may be fused to a TMZ domain to create a membrane-bound trimerized 4-1BB ligand.

TMZ-CD154 as defined herein may be combined with a 4-1BB ligand extracellular domain and transmembrane domain may be fused to a TMZ domain to create a membrane-bound trimerized 4-1BB ligand.

TMZ-CD154 as defined herein may also be combined with decoy molecules to block, alter or activate signaling pathways. The decoy molecule may be an antibody, a single chain fragment derived from an antibody, a receptor, a ligand, or part of such.

The decoy molecule as defined above can be a decoy molecule, which will block or alter the interleukin-6 (IL6) receptor/IL6 ligation.

Thus, the decoy molecule may be a scFv targeting the IL6 receptor, or a scFv targeting the IL6 molecule.

Alternatively or additionally, the decoy molecule defined above can be a decoy molecule, which will block the STAT3 pathway, gremlin-1, the IL10/IL10 receptor ligation, or Arginase-I.

TMZ-CD154 as defined herein may be combined with any of the modulators defined above in the same vehicle system (genetic, cells or artificial vehicles) as defined herein. For example, the TMZ-CD154 nucleotide sequence can be in trans with the 4-1BB ligand nucleotide sequence in a genetic vector.

The combination of TMZ-CD154 and another modulator may be placed in trans in a vector system and separated by an IRES sequence or similar to allow expression of both genes, or the combination of TMZ-CD154 and another modulator may be placed in trans in a vector system separated by a sequence for a 2A peptide or similar that allows for a single gene transcript for the two modulators that are separated to two entities post translation.

Combination of TMZ-CD154 with One or More Immunomodulators for Use in Medicine

The nucleotides or proteins according to the invention, notably TMZ-CD154 as defined herein may be combined with any of the modulators as defined herein in the different vehicle systems (genetic, cells or artificial vehicles) as defined herein, but used together to treat diseases. For example, two vehicles carrying TMZ-CD154 and 4-1BB ligand, respectively, can be used simultaneously or at different time points during treatment of, but not limited to, cancer or infectious disease.

The vehicles may be an adenoviral vector armed with TMZ-CD154 and the other vehicle may be an adenoviral vector armed with 4-1BB ligand.

One of the vehicles can also be an adenoviral vector armed with TMZ-CD154 and the other vehicle may be an adenoviral vector armed with an anti-IL6 receptor scFv.

Alternatively, one of the vehicles may be an adenoviral vector armed with TMZ-CD154 and the other vehicle may be another vector system armed with 4-1BB ligand, or one of the vehicles may be an adenoviral vector armed with TMZ-CD154 and the other vehicle may be another vector system armed with an anti-IL6 receptor scFv.

The vehicle may also be an adenoviral vector armed with TMZ-CD154 combined with protein 4-1BB ligand or the vehicle may be an adenoviral vector armed with TMZ-CD154 combined with an antibody or scFv blocking the IL6 receptor, or the vehicle may be an adenoviral vector armed with TMZ-CD154 combined with an antibody or scFv blocking the IL6.

TMZ-CD154 for Use in Combination with Approved Treatments

The nucleotides and proteins according to the invention, eg TMZ-CD154 as defined herein, can also be combined with approved treatments for diseases such as different drugs, radiotherapy or surgery.

Thus, the nucleotides and proteins according to the invention, eg TMZ-CD154 as defined herein, may be combined with e.g.

i) approved immunomodulatory therapies, ii) approved antibody-body based therapeutics such as, but not limited to, trastuzumab (anti-Her2), rituximab (anti-CD20), tocilizumab (anti-IL6R), ipilimumab (anti-CTLA-4), nivolumab (anti-PD1), and pembrolizumab (anti-PD1).

iii) approved immune derived cell therapies such as, but not limited to, T cell therapy (natural tumor-targeting such as expanded tumor-infiltrating lymphocytes, or genetically engineered such as CAR T cells or TcR engineered T cells), NK cell therapies or dendritic cell vaccines, iv) approved T cell therapy (natural tumor-targeting T cells such as expanded tumor-infiltrating lymphocytes, or genetically engineered such as CAR T cells or TcR engineered T cells), v) approved NK cell therapy, vi) approved dendritic cell vaccine, vii) approved vaccines such as, but not limited to, tumor cell vaccines, tumor or viral antigen peptides or other viral or bacterial antigens, viii) approved tumor cell vaccines, ix) approved tumor or viral antigen peptides, x) approved viral or bacterial antigens such as, but not limited to, pp65 CMV peptide or full length protein, *bacillus* Calmette-Guérin (BCG) or unmethylated CpG nucleotides, xi) approved immune modulators including, but not limited to, imiquimod, interferons (such as IFN gamma, IFN alpha), interleukines/cytokines (such as IL2) and growth factors (such as GM-CSF), xii) approved cancer therapeutics including alkylating agents, anti-metabolites, anti-microtubule agents, topoisomerase inhibitors and cytotoxic antibiotics, xiii) approved chemotherapy for cancer such as but not limited to alkylating agents including mechlorethamine, bendamustine, cyclophosphamide, melphalan, chlorambucil, ifosfamide, busulfan, N-nitroso-N-methylurea, carmustine, lomustine, semustine, fotemustine, streptozotocin, dacarbaxine, mitozolomide, temoxolomide, thiotepa, mytomycin, diaziquone, cisplatin, carboplatin, oxaliplatin, procarbaxine and hexamethylmelamine, xiv) cyclophosphamide, xv) bendamustine, xvi) temoxolomide.

xvii) cisplatin, carboplatin or oxaliplatin, xviii) approved chemotherapy for cancer such as but not limited to anti-metabolites such as anti-folates, fluoropyrimidines, deoxynucleoside analogues and thiopurines, xix) an anti-folate such as methotrexate or pemetrexed, xx) a fluoropyrimidine such as fluorouracil or capecitabine, xxi) a deoxynucleoside analogue such as cytarabine, gemcitabine, decitabine, vidaza, fludarabine, nelarabine, cladribine, clofarabine or pentostatin, xxii) a gemcitabine, xxiii) a thiopurine such as thioguanine or mercatopurine, xxiv) approved chemotherapy for cancer such as but not limited to anti-microtubule agents such as vinca alkaloids, taxanes or other drugs that blocks microtubule formation or that stabilizes microtubule, xxv) vincristine, vinblastine, vinorelbine, vindesine or vinflunine, xxvi) paclitaxel or docetaxel, xxv) etoposide, teniposide or other agent that block microtubule formation or that stabilizes microtubule, xxvi) approved chemotherapy for cancer such as but not limited to topoisomerase inhibitors, xxvii) irinotecan, topotecan, or camptothecin, xxviii) approved chemotherapy for cancer such as but not limited to cytotoxic antibiotics, xxix) doxorubicin, daunorubicin, pirarubicin, aclarubicin, mitoxantrone,
xxx) approved cancer therapeutics including radiotherapy such as external beam radiation therapy, brachytherapy and radioisotope therapy,
xxxi) external beam radiation therapy such as conventional external beam radiation therapy, stereotactic radiation, virtual simulation, 3-dimensional conformal radiation therapy/intensity-modulated radiation therapy, particle therapy and auger therapy,
xxxii) brachytherapy,
xxxiii) radioisotope therapy,
xxxiv) approved cancer therapeutics including angiogenesis inhibitors,
xxxv) bevacizumab or afibercept,
xxxvi) approved cancer therapeutics including pathway inhibitors,
xxxvii) inhibitors of EGFR, RET, mutated BRAF, tyrosine kinases, mTOR, Hedgehog, Smo, PI3K, MEK, AKT, RAF, Rac1, PARP, PIM, cMET, STAT3, JAK2, p38MAPK, NOTCH, BCL-2, IAP, p53, GSK2, Chk1, CDK4/6, PDGFR, IGF-1R, DKK1, CF-1R, or TWEAK:Fn14,
xxxviii) inhibitors of mutated BRAF including V600E such as Vemurafenib,
xxxix) inhibitors of tyrosine kinases such as, but not limited to, imatinib, dasatinib, nilotinib, and sunitinib,
xxxx) inhibitors of STAT3,
xxxxi) inhibitors of Rac-1,
xxxxii) inhibitors of BCL-2,
xxxxiii) inhibitors of apoptosis inhibitors such as, but not limited to, ABT-737 or navitoclax,
xxxxv) approved anti-viral therapeutics,
xxxxvi) approved anti-viral therapeutics including, but not limited to, abacavir, aciclovir, acyclovir, adefovir, atazanavir, boceprevirertet, cidofovir, darunavir, delavirdine, efavirenz, entecavir, foscarnet, ganciclovir, lamivudine, oseltamivir, valaciclovir, valganciclovir,
xxxxvii) aciclovir, acyclovir, foscarnet, ganciclovir or valganciclovir,
xxxxviii) foscarnet, ganciclovir and valganciclovir.

Administration Routes

In principle any administration route can be used provided the expected effect is obtained. In general, parenteral administration is envisaged.

Thus, the nucleotide sequence according to the invention may be administered by the parenteral administration route such as by intraveneous injection, by percutaneous injection, by injection directly into a diseased organ or tissue, or by intratumoral injection. In the latter case, the administration may take place by image-guided injection into a tumor Pharmaceutical Compositions The present invention also relates to pharmaceutical compositions for use in treating immune related diseases such as cancer and infectious diseases. Examples of such diseases are given herein. A pharmaceutical composition of the invention comprises TMZ-CD154 as defined herein in a genetic vehicle as defined herein.

The compositions may be designed to oral, parenteral or mucosal administration. Thus the administration may be oral, sublingual, application to the oral mucosa, or it may be intraveneous, subcutaneous, intramuscular, intraperitoneal, intrahecal, intratumoral etc. or it may be applied to the skin or a mucosa surface including ocular, buccal, nasal, vaginal and rectal mucosa. However, it is contemplated that the parenteral administration route is the most efficient, notably injection directly into the diseased area such as injection directly into a tumor or a metastasis.

The composition may be in solid, semi-solid or liquid form.

Suitable solid compositions include powders, granules, pellets, capsules, tablets (included coated tablets), sachets, implants, drug delivery devices, films etc.

Suitable semi-solid compositions include gels, pastes, cremes, ointments, vagitories, suppositories etc.

Suitable liquid or fluid compositions include solutions, dispersions, emulsions, suspensions, lotions, sprays, aerosols.

The pharmaceutical compositions suitable for injection include sterile aqueous solutions or dispersions. It may also be in the form of liquid, which solidify once it is injected locally e.g. into a tumor. It may also be in the form of an implant, insert or delivery device.

For parenteral use, the composition may be e.g. in liquid form containing TMZ-CD154 in a genetic vehicle in a solvent or dispersion medium such as water, ethanol, propylene glycol, isopropanol, glycerol, vegetable oil like e.g. sesame oil, peanut oil or the like. Additives like e.g. buffering agents, pH-adjusting agents, solubilizing agents, stabilizing agents, preservatives etc. may be added. Moreover, it may contain excipients, which are pharmaceutically acceptable for a composition to be injected. These may be in particular isotonic, sterile saline solutions (phosphate, sodium chloride) or dry, especially freeze-dried compositions, which upon addition, depending on the case, of sterilized water or physiological saline or another solvent or dispersion medium, are reconstituted to a ready-to-use composition.

Advantageously, such additives may be dissolved in the solvent. To enhance the stability, the composition can be frozen after filling into the vial and the water removed under vacuum. The dry lyophilized powder is then sealed in the vial and an accompanying vial of water for injection may be supplied to reconstitute the liquid prior to use.

The composition may also be presented as a frozen composition, which is thawed prior to therapy. It could eg be a composition containing a viral vector. Such a composition may be used as it is or additives may be added such as aqueous medium comprising eg buffer substances, pH regulating agents, tonicity adjusting agents etc.

The compositions may conveniently be presented in unit dosage form and may be prepared by any of the methods well known in the art of pharmacy. Such methods include the step of bringing into association the active molecule (TMZ-CD154 carried by a vehicle) with the carrier that constitutes one or more accessory ingredients. In general the compositions are prepared by uniformly and intimately bringing into association the active ingredient with liquid carriers or finely divided solid carriers or both, and then, if necessary, shaping the product.

As mentioned above the nucleotide sequence or protein according to the invention, eg TMZ-CD154, contained in a genetic vehicle may be administered orally in the form of a pharmaceutical composition. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Compositions for use in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above the formulations of this invention may include other agents conventional in the art having regard to the type of formulation in question, for example those suitable for oral administration may include flavouring agents.

As shown in the examples herein, a nucleotide sequence according to the invention maybe used in a composition, which is in the form of an aqueous composition, wherein the aqueous medium is a physiologically acceptable medium normally used for injection. Such an aqueous medium may be 0.9% sodium chloride, Ringer's solution or a Tris/glycerol buffer solution.

When the TMZ-CD154 is delivered via a virus (such as seen from the examples herein), the virus containing the nucleotide according to the invention can be purified by ultracentrifugation (using for example cesium chloride) and the concentrated virus is dialysed into a Tris/glycerol buffer solution (containing 20 mM Tris, 25 mM sodium chloride, 2.5% w/v glycerol, pH adjusted to pH 8.0). Thus, the nucleotide is administered in the buffer and if necessary, the buffer may be diluted with the same Tris/glyceol buffer solution or a suitable solution for in vivo administration for example one or the other solutions mentioned above.

A person skilled in the art will be able to prepare a composition that is suitable for use in accordance with the present invention based on the disclosure herein and/or with guidance from Remington's Pharmaceutical Sciences, 18$^{th}$ Ed., Mack Publishing Company, 1990 or newer editions.

A pharmaceutical composition of the invention may also contain TMZ-CD154 in combination with one or more of the immunomodulators mentioned herein or in combination with one or more of the other therapeutically active agents mentioned herein. Such composition may either contain all active elements in the same formulation (e.g. in the form of a unit dose the unit dose contains all the active molecules) or it may be in the form of a package containing a set of formulations each containing one or more of the active molecules (e.g. in the form of a package containing two different formulations, one containing TMZ-CD154 in a vehicle and the other containing the other active molecule; or in the form of a package containing e.g. two different formulations, one containing TMZ-CD154 in a vehicle and an immunomodulator, and the other containing another active molecule).

The dosage to be administered of a TMZ-CD154 molecule will vary according to the particular molecule, the vehicle comprising the molecule, the disease involved, the subject, and the nature and severity of the disease and the physical condition of the subject, and the selected route of administration.

The appropriate dosage can be readily determined by a person skilled in the art.

The compositions may contain from 0.1% by weight, preferably from 5-95%, more preferably from 10-60% by weight, of a compound of invention, depending on the method of administration and the form of TMZ-CD154 (e.g. used as a protein or gene therapy). Adenoviral vectors may be in concentrations ranging from $1 \times 10e6$ to $1 \times 10e14$ viral particles per mL. A suggested dose per treatment may preferably range from $1 \times 10e9$ to $1 \times 10e13$ viral particles per mL if administered by intratumoral injection or intravenous infusion.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In the following is illustrated the use of TMZ-CD40L in medicine, notably in cancer immunotherapy.

Cancer Immunotherapy

Tumor Immunology and Cancer Immunotherapy

The immune system can recognize and kill tumor cells by the same mechanisms as it recognizes and kills virally infected cells to save the host against lethal infections. Like virally infected cells, tumor cells are self-cells, and viral- or tumor-associated epitopes are presented on major histocompatibility complex I (MHC-I) on the cells to CD8+ cytotoxic T lymphocytes (CTLs). Both virally infected cells and tumor cells may prevent CTL recognition by down-regulating MHC molecules making the cells targets for natural killer (NK) cells. However, viruses initially activate an innate immune defense response, alerting antigen-presenting cells such as dendritic cells (DCs) to activate anti-viral immunity, while tumor cells do not induce the same degree of stimulation. Indeed, during cancer progression the tumor and its stroma produce substances that inhibit immune cells. Tumor immunity is restrained by blocking DC maturation and promoting differentiation and attraction of immunosuppressive cells to the tumor milieu. These suppressive cells are usually M2 macrophages, a variety of immature myeloid cells collectively called myeloid-derived suppressor cells (MDSCs) and T regulatory cells (Tregs). Such cells produce suppressive cytokines and growth factors such as IL10, TGFβ, Prostaglandin E2, Arginase I and myeloid peroxidase. In the tumor milieu, activated CTLs are rapidly suppressed by these factors and become anergic, a state of reversible unresponsiveness, or die.

The essence of cancer immunotherapy is to break tumor tolerance (e.g. break anergy) and revert the ongoing type 2 immune responses to type 1. Type 1 is characterized by activation of T helper 1 (Th1) lymphocytes, CTLs, NK cells and M1 macrophages as well as by a cytokine pool such as IFNγ, IL12, IL21 and TNF.

The recent success of checkpoint blockade antibodies targeting CTLA4 and PD1/PDL1 for melanoma and other solid malignancies as well as chimeric antigen receptor (CAR) T cells for B cell malignancies has greatly strengthened the field of cancer immunotherapy. Novel concepts to treat cancer by stimulating the immune system are currently being investigated. One of these concepts is immunostimulatory gene therapy utilizing oncolytic viruses as gene delivery vehicles.

Immunostimulatory Gene Therapy

Immunostimulatory gene therapy aims to transfer genes coding for immunostimulatory proteins into the tumor area. The first studies using immunostimulatory gene therapy in experimental models were published in the late nineties with promising results. Different approaches were used in clinical trials as well but many failed to show efficacy. However, these studies were performed before the increased knowledge of suppressive immune cells infiltrating the tumor and the possibility to aid the immune responses using preconditioning or supportive chemotherapy that reduce the levels of these immunosuppressive cells. Further, the responses to immunotherapy follow a different course compared to traditional chemotherapy or irradiation. Initial swelling of the tumor due to inflammation may have been misinterpreted as progression leading to premature interruption of treatment. The combination of preconditioning/supportive chemotherapy together with awareness on how to interpret data will likely pave the way for immunostimulatory gene therapy as it has for other immunotherapies. Compared to the systemic delivery of soluble immunostimulatory cytokines, growth factors and antibodies, gene therapy can be delivered to a distinct site with days to weeks of expressing the immunostimulatory transgenes depending on the vector used. This leads to a high concentration of the immunostimulatory proteins in the tumor reducing toxicity due to unnecessary withdrawal of tolerance to self-cells that can be seen upon systemic immune activation.

Therapeutic immunostimulatory genes are delivered to the tumor by the use of a great variety of vehicles. Replication deficient adenoviruses have been commonly used since they can carry large transgene cassettes. Unfortunately, transgene expression is of limited duration because adenoviruses do not integrate into the host cell genome. The lack of integration increases safety since the risk for mutagenesis of the host cell is unlikely. Moreover, humans are fully equipped to handle adenoviral infections. For example, most individuals have had upper respiratory tract infections due to adenoviruses and have performed antibodies against several serotypes, and T-cells cross-reactive to all. For immunostimulatory gene therapy, the immunostimulatory effect of the virus may aid formation of anti-tumor responses by activating TLRs on tumor antigen-loaded DCs. Nevertheless, upon intratumoral delivery, the virus infects cells in the needle tract and there is a need to increase virus infection to prolong transgene expression. This may be achieved by using oncolytic viruses as gene delivery vehicles.

Oncolytic Virus (OV) Therapy

The ability of certain viruses to infect cells, propagate and kill them by lysis during the release of new virions means that they can be utilized as cancer therapeutics. To limit oncolysis to tumor cells, the expression of virus replication genes are restricted by adding promoters that are preferentially active in the tumor. For full benefit, the OVs should infect all tumor cells, which can be a challenge if the tumor has metastasized. Since systemic viral spreading to distal tumor may be limited by the immune system, attempts are being made to develop less immunogenic OVs.

Instead of decreasing the immunogenicity of OVs, another approach is to utilize and boost their intrinsic immunostimulating capacity of the virus by adding immunostimulatory genes into the OV genome. Oncolytic adenoviruses armed with immunostimulatory transgenes successfully deliver them to the tumor and arm a systemic anti-tumor immune response active against metastatic disease. The full efficacy of the combined oncolysis and immune stimulation is difficult to determine in murine models since the oncolysis is limited in murine cells and the immunostimulatory effect cannot be evaluated in xenograft models in immunodeficient mice. There has been at least one published study using an oncolytic adenovirus carrying the full-length human CD40L gene to patients with end-stage cancer demonstrating feasibility and safety. There are other studies ongoing using GM-CSF armed oncolytic viruses and a herpes simplex virus armed with GM-CSF (talimogene laherparepvec) has already completed Phase III registration trials in patients with melanoma.

Preconditioning or Supportive Chemotherapy

Preconditioning or supportive chemotherapy is often given to patients receiving immunotherapy to decrease inhibitory tumor stromal cells such as Tregs and MDSCs that may otherwise hinder the intended immune activation. Further, chemotherapy-induced lymphocyte or myeloid cell depletion may induce bone marrow cytokine production that restores the immune cell populations (i.e. by homeostatic replication), and favors the activation of anti-tumor responses. Dependent on diagnosis and type of chemotherapy, tumor growth may also be affected. Metronomic cyclophosphamide has been given to patients undergoing immunotherapy in an attempt to control of suppressive immune cells. Such supportive chemotherapy protocols may be of great value if they do not hamper the desired anti-tumor responses. One such supportive chemotherapy of interest may be gemcitabine.

Gemcitabine is a nucleoside analog that replaces cytidine during DNA replication, and leads to growth arrest and apoptosis. Gemcitabine also targets ribonucleotide reductase thereby blocking the function of this enzyme. It is currently standard of care for pancreatic cancer both as adjuvant treatment to surgery and as single treatment for advanced tumors. Although gemcitabine treatment of advanced metastasized tumors is only palliative, several studies, including our own, have shown that patients treated with gemcitabine had significantly lower levels of the immunosuppressive molecule TGF☐, Tregs and MDSCs but an increased number of DCs, monocytes and activated T cells. Recently it was shown that gemcitabine reduced MDSC recruitment to the tumor and accelerated the development of anti-tumor T cell responses, which aided combination therapy with an oncolytic Reovirus. In mice, gemcitabine reduced MDSCs and enhanced the efficacy of immunotherapy.

Hence, a combination of gemcitabine standard-of-care with immunotherapy may be beneficial for these patients.

The Investigational Product LOAd703 Comprising TMZ-CD40L

LOAd703 is a novel immunotherapy for cancer. It is an oncolytic adenovirus serotype 5 with a fiber (shaft and knob) from serotype 35 (Ad5/35) to increase binding to cells and thereby its infectivity. Virus replication and oncolysis is restricted to cells with a dysfunctional retinoblastoma (Rb) pathway due to an E1AΔ24 and multiple E2F binding domains upstream of E1A. Rb in normal cells binds to the transcription factor E2F thereby blocking its intrinsic capacity to induce transcription of genes that promote transition from G1 into S phase of the cell cycle. Upon phosphorylation of Rb, E2F is released to stimulate cell proliferation. Human tumors have a wide spectrum of mutations that alters the Rb protein and/or factors that leads to hyperphosphorylation of Rb. Hence, in cancer cells E2F is free to drive transcription of the virus. The virus infects and kills tumor cells via oncolysis due to excessive virus replication while healthy nonmalignant cells can be infected but no new virus particles are produced. Therefore, LOAd703 does not kill healthy cells. LOAd703 has a transgene cassette with two immunostimulatory genes (TMZ-CD40L and 4-1BBL) driven by a CMV promoter. The CMV promoter is not tissue restricted and the immunostimulatory genes can be expressed in all cells that are infected by LOAd703. Hence, LOAd703 targets both the tumor and its stroma. Since the virus is administered by intratumoral injection, the expression of the transgenes is localized to the tumor area.

Schematic Gene Construct

LOAd703 replication is controlled via an E1AΔ24 that restricts replication of the virus in cells with a disrupted (hyper phosphorylated) retinoblastoma protein commonly seen in malignant cells. Further, a region of E2F promoters and an Sp-1 site have been inserted prior to E1A. These replication restrictions will promote virus replication in tumor cells eventually driving the tumor into oncolysis and death. The LOAd703 viruses can infect normal cells but do not replicate nor kill normal cells. Further modifications include 6.7K and gp19K deletions in the E3 region. 6.7K inhibits TRAIL receptor 1 and 2 in the cell while gp19K traps MHC in the endoplasmatic reticulum (ER). Together, these two reduce the ability of T cells to recognize and kill virus-infected cells. Since the purpose of LOAd703 is to enhance immunogenicity, these regions were removed from the adenovirus genome. The serotype 5 fiber shaft and knob region situated in the L5 region was changed to the shaft and knob region from a serotype 35 virus which increases the virus transduction since the 35 fiber binds to the receptor CD46 abundantly expressed on both normal and malignant human cells while the Ad5 fiber is restricted to cells positive for the coxsackie-, adenovirus receptor. After the L5 region, a transgene cassette with TMZ-CD40L and 4-1BBL genes driven by a cytomegalovirus promoter (pCMV) was inserted. Upon infection of cells, the LOAd703 virus will, hence, induce expression of TMZ-CD40L and 4-1BBL. The expression is driven by the CMV promoter and is not dependent on virus replication. Any cell infected within the tumor upon intratumoral injection can express the transgenes.

The TMZ-CD40L transgene is a modified human CD40 ligand (CD40L; CD154) that lacks the intracellular signaling domain and instead fuses the extracellular and transmembrane domains to an isoleucine zipper domain. This creates a membrane-bound trimerized CD40L molecule that lacks intracellular signaling in the TMZ-CD40L-expressing cell but still binds and transmits signals to other cells that express its receptor CD40. CD40L is normally expressed on many cell types under pathological conditions, i.e. when the cells are stressed or activated. CD40L stimulation of CD40+ cells leads to different actions depending on the identity of the CD40+ cell. Immature DCs express CD40 and upon CD40L stimuli the DCs differentiate into a mature phenotype that expresses enhanced levels of major histocompatibility complex (MHC) molecules, costimulatory molecules and cytokines. Such mature DCs are excellent stimulators of T cells (Th1 and CTLs), NK cells and M1 macrophages. CD40+ endothelial cells increase expression of molecules important for T cell attachment and diapedesis promoting recruitment of T cells. However, CD40+ tumor cells have a skewed CD40 intracellular signaling pathway and upon CD40L stimulation most tumor cells are growth inhibited or enter apoptosis. Further, CD40L-mediated signaling in the tumor microenvironment can indirectly reduce the level of Tregs in bladder cancer patients treated with CD40L gene therapy (AdCD40L). In a murine model, the myeloid cell population was tilted from suppressive CD11b+Gr1$^{int/low}$ and M2 cells into CD11b+Gr1$^{high}$, and M1 myeloid cells.

The 4-1BB ligand (4-1BBL; CD137L) transgene is the full-length human 4-1BBL gene. It binds to its receptor 4-1BB (CD137) expressed on activated T cells and NK cells. 4-1BBL stimulation of T cells and NK cells protects the cells from activation-induced cell death (AICD) via upregulation of apoptosis inhibitors such as BCL-xL. 4-1BBL stimulation also promotes efficient lymphocyte proliferation. 41BBL is a good in vitro stimulator of both CTLs and NK cells but for in vivo efficacy in tumor models the combination of 41BBL with other immune enhancers seems crucial. The combination of CD40L and 4-1BBL stimulation, as well as the adenoviral backbone stimulation of Toll-like receptors (TLRs) potently stimulates DCs, T cells and NK cells in our preclinical experimental settings described below.

Thus, LOAd703 expresses CD40L and 4-1BBL, and hence, has two major effector mechanisms: 1) induction of cell death via either oncolysis or CD40-mediated apoptosis, and 2) activation of the immune system via CD40L, 41BBL and the adenoviral backbone. The major effector arm is likely immune activation but the induction of cell death by oncolysis further strengthens anti-tumor responses due to the release of tumor antigens resulting in tumor antigen-specific immune stimulation.

Abbreviations aCTLA4 Anti-cytotoxic T lymphocyte antigen 4
Ad Adenovirus
AICD Activation-induced cell death
CD Cluster of differentiation
CD40L CD40 ligand, CD154
CMV Cytomegalovirus
CTL Cytotoxic T lymphocyte
DC Dendritic cell
GM-CSF Granulocyte macrophage-colony stimulating factor
IFNg Interferon gamma
IL Interleukin
LOAd Lokon oncolytic adenovirus
MDSC Myeloid-derived suppressor cell
NK Natural killer
PCR Polymerase chain reaction PDAC Pancreatic ductal adenocarcinoma
PD1 Programed death receptor 1
PDL1 Programed death receptor ligand 1
Rb Retinoblastoma
TCR T Cell Receptor
TGFb Transforming growth factor beta
Th T helper
TLR Toll-like receptor
TMZ-CD40L Trimerized membrane-bound CD40L
TNFa Tumor necrosis factor alpha
Treg T regulatory cell
VP Virus particles
4-1BBL 4-1BB ligand, CD137 ligand Definitions Ad5/35: The term "Ad5/35" means an oncolytic serotype 5 adenovirus vector, wherein the fiber and knob of the shaft are from Ad serotype 35

Antigen: The term "antigen" is a target that is recognized by T cells via the T cell receptor, a chimeric antigen receptor or an equivalent thereof.

cDNA: The term "cDNA" means a DNA molecule that can be prepared by reverse transcription from a mature, spliced mRNA molecule obtained from a cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of TMZ-CD154 or variant thereof. The boundaries of the coding sequence are generally determined by an open reading frame, which begins with a start codon such as ATG, GTG or TTG and ends with a stop codon such as TAA, TAG or TGA. The coding sequence may be genomic DNA, cDNA, synthetic DNA, or a combination thereof.

Expression: The term "expression" includes any step involved in the production of TMZ-CD154 including, but not limited to, transcription, post-transcriptional modification, translation, post-translational modification, and secretion.

Host cell: The term "host cell" means any cell type that is susceptible to transformation, transfection, transduction, or the like with a nucleic acid construct or expression vector comprising a polynucleotide as described herein.

Operably linked: The term "operably linked" means a configuration in which a control sequence is placed at an appropriate position relative to the coding sequence of a polynucleotide, such that the control sequence directs expression of the coding sequence Origin of replication: The term "origin of replication" means the particular sequence in the genome at which replication is initiated. This can involve the replication of DNA in living organisms such as prokaryotes and eukaryotes, or that of DNA or RNA in viruses such as double-stranded RNA viruses.

Replication-competent viral vector: The term "replication-competent viral vector" is a virus that is capable of replicating by its own means in any cell that it infects or in cells of specific origin.

Replication-deficient viral vector: The term "replication-deficient viral vector" is a virus, which is not capable of replicate by its own means because of deletion of genes involved in viral replication.

Sequence identity: The term "sequence identity" means the relatedness between two amino acid sequences or between two nucleotide sequences. Algorithms for nucleotide queries: blastn, megablst, discontiguous megablast. Algorithms for protein queries: blastp, psi-blast, phi-blast, delta-blast.

Viral vector: The term "viral vector" means a tool to deliver genetic material into cells.

The term "comprising" is to be understood in a broad sense, but encompasses the terms "containing", "consisting of" and in connection with a molecular structure the structure may be as shown, i.e. without any further elements.

LEGENDS TO FIGURES

FIG. 1: A) A schematic figure demonstrating the TMZ-CD154 molecule. B) A schematic figure demonstrating the trimerized TMZ-CD154 molecule on the cell plasma membrane (PM) with or without interacting with the CD40 receptor on a neighbor target cell.

Figure 2:
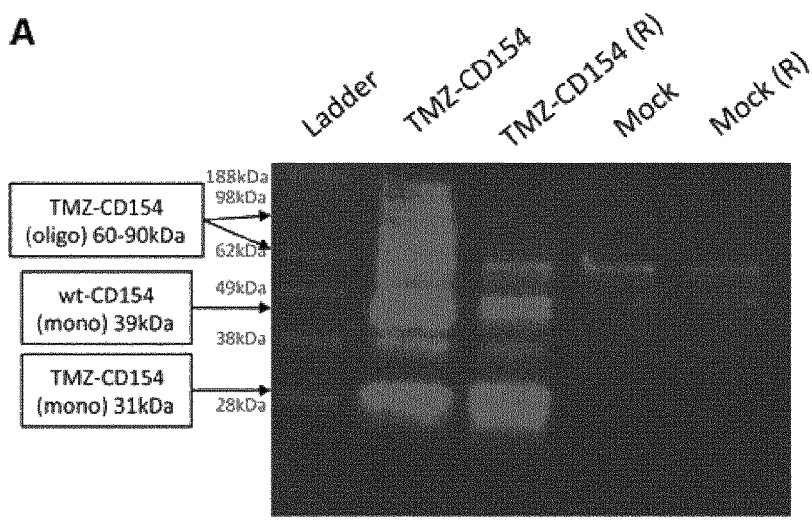
Figure 2:
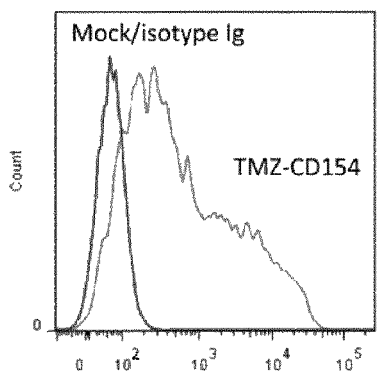
Figure 2:
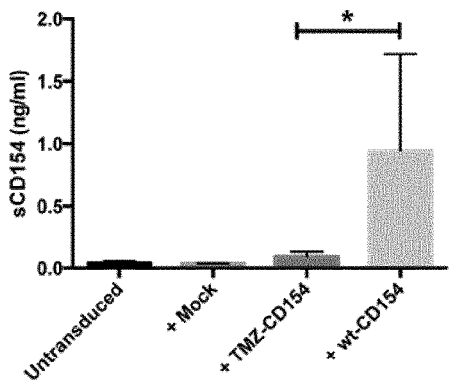
Figure 2:
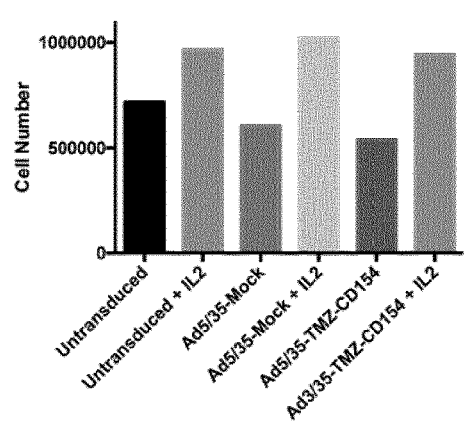

FIG. 2: 293 cells were transfected with a plasmid containing TMZ-CD154 or an empty Mock plasmid. A) After two days of culture the cells were lysed and the protein suspension analyzed by gel electrophoresis and Western blot to detect TMZ-CD154. The samples were divided in two groups in which the first group was boiled in reducing sample buffer (R), and the other group was not boiled and mixed with a non-reducing sample buffer prior to gel electrophoresis. B) After two days of culture a portion of the cells were analyzed by flow cytometry to demonstrate TMZ-CD154 expression. C) The supernatants from Panc01, BxPc3, MiaPaca2 and PaCa3 cells transduced with Ad5/35 virus expressing TMZ-CD154, wild type CD154 or no transgenes (Mock) were analyzed for release of soluble CD154 into supernatants using ELISA. D) An adenovirus serotype 5/35 was used to transduce T cells with the TMZ-CD154 molecule. Controls were not transduced or transduced with an empty (Mock) virus. Cells were cultured for 48 hrs with or without IL2.

Figure 3:
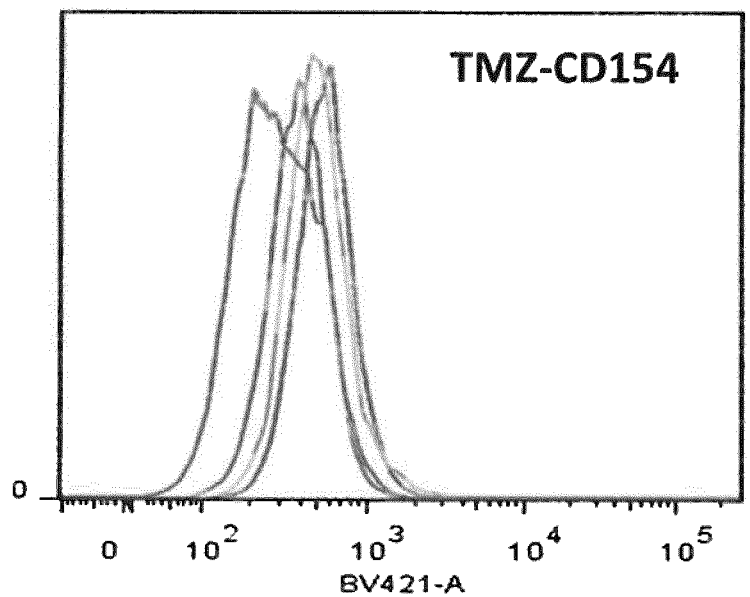
Figure 3:
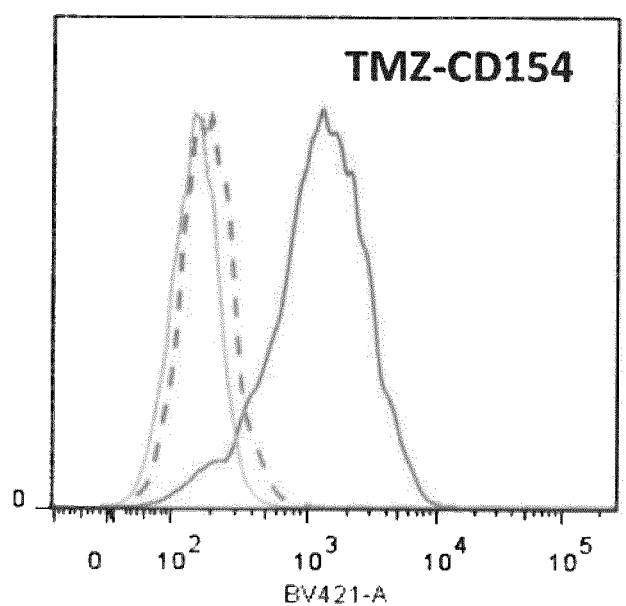

FIG. 3: Dendritic cells (A) and MiaPaCa2 (B) cells were transduced with 100 MOI of the Ad5/35-TMZ-CD154 virus (red line), a Mock virus (green line) or left untransduced (grey line). The DCs were also transduced with two other versions of Ad5/35-TMZ-CD154 virus combined with 4-1BBL (orange line) or scFv aIL6R (blue line). 24 hours later the cells were analyzed for the expression of TMZ-CD154 by flow cytometry. Untransduced or Mock transduced did not express TMZ-CD154 while the Ad5/35-TMZ-CD154 transduced cells demonstrated a robust expression that was higher expressed in tumor cells compared to DCs.

Figure 4:
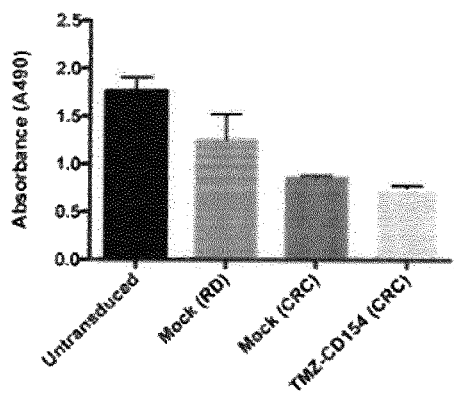
Figure 4:
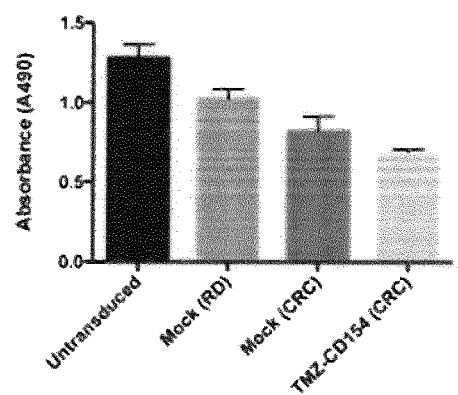
Figure 4:
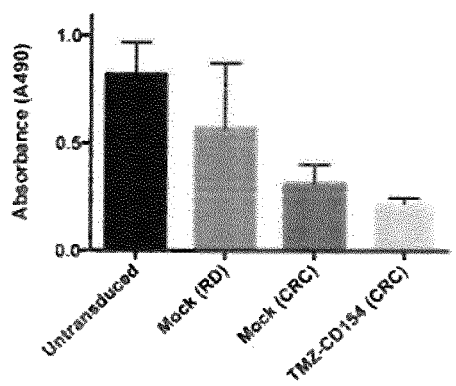
Figure 4:
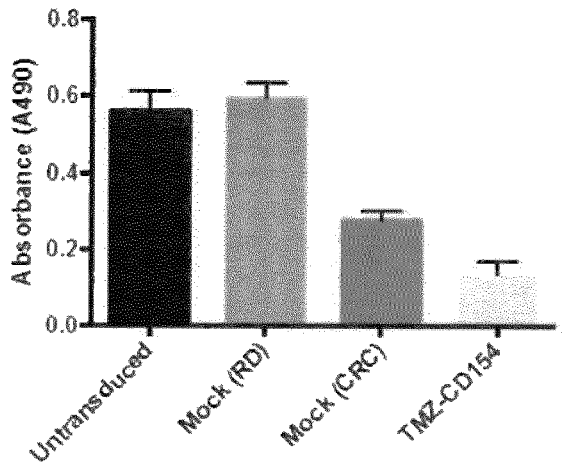

FIG. 4: Pancreatic cancer tumor cell lines were transduced with the Ad5/35-TMZ-CD154 conditionally replication competent (oncolytic) virus (CRC), a Mock oncolytic virus (CRC), a replication deficient Mock virus (RD), or left untransduced. Transduced cells were seeded into 96 well plates and analyzed for survival using the MTS viability assay to determine the level of cell death by oncolysis of A) Panc01, B) MiaPaCa2 or C) BxPC3. D) The same assay was performed on a lymphoma cell line (Karpas 422).

Figure 5:
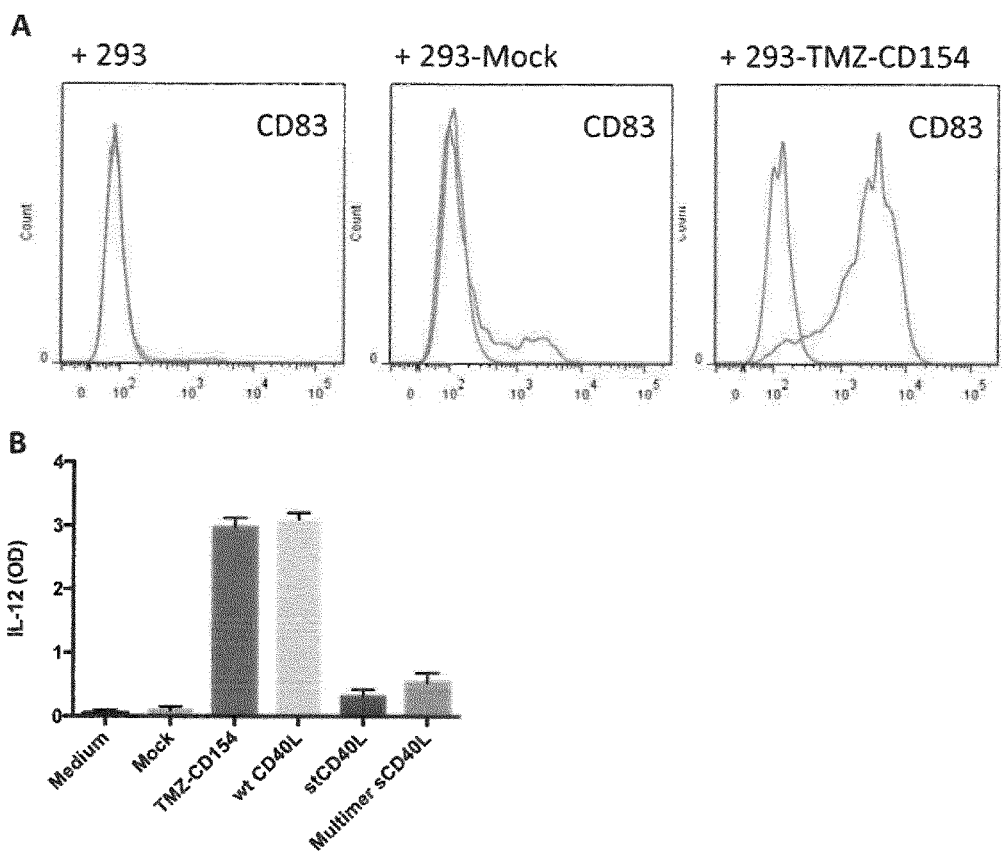

FIG. 5: Immature dendritic cells were co-cultured with 293 cells transfected with TMZ-CD154, soluble trimerized (st) CD154 (CD40L), multimeric soluble CD154 (CD40L), or Mock plasmids, or left untransfected. After two days of co-culture, the cells were analyzed by flow cytometry for CD83 expression (A). Supernatants were collected and analyzed for IL-12 expression using ELISA (B).

Figure 6:
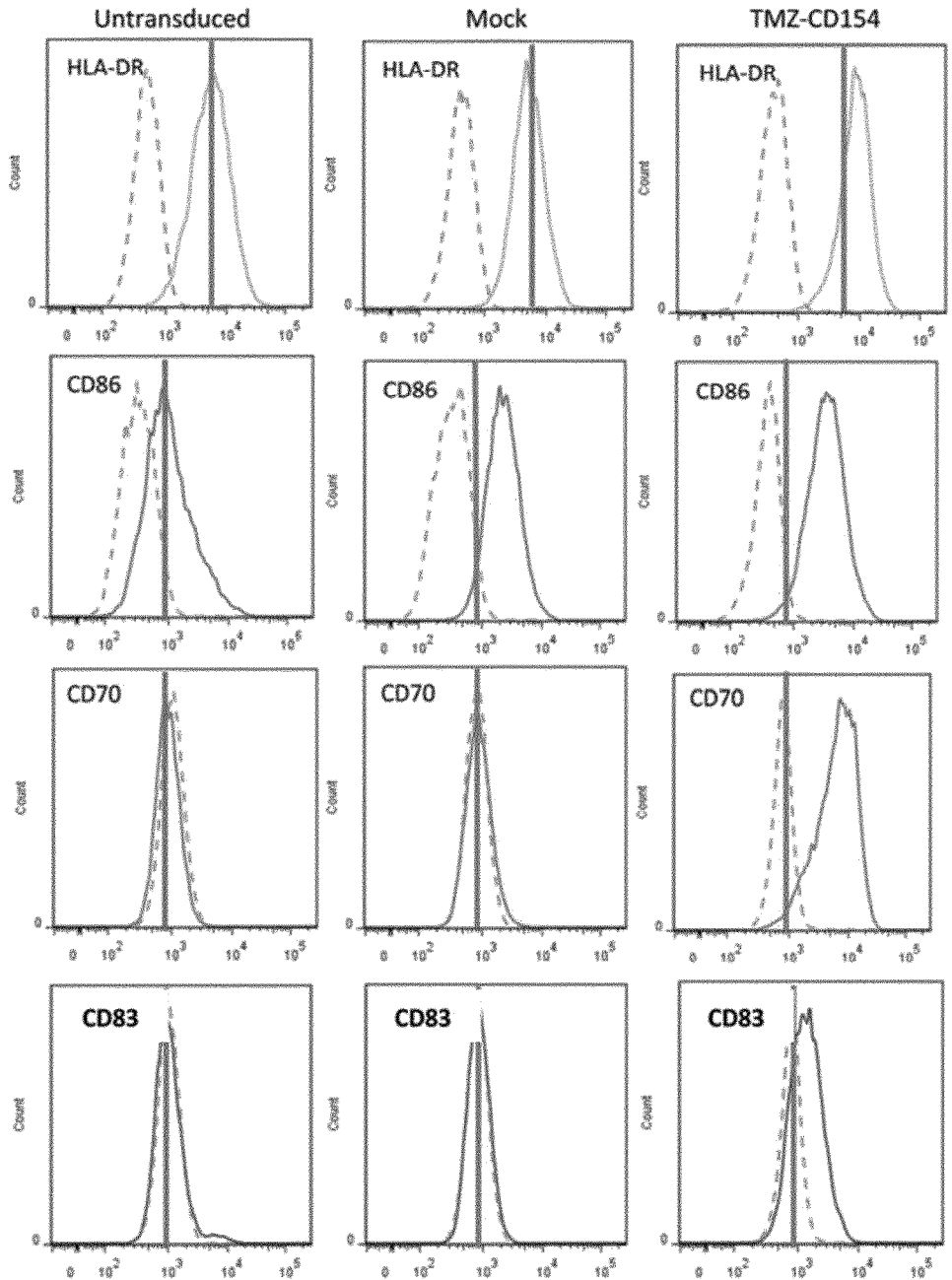
Figure 6:
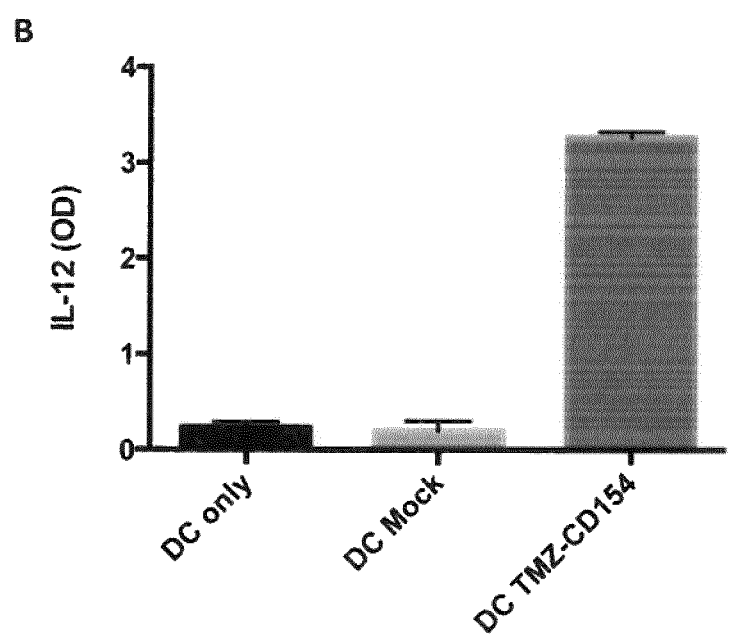

FIG. 6: Immature dendritic cells were transduced with the Ad5/35-TMZ-CD154 virus or Mock virus, or left untransduced (DC only). After two days of culture, the cells were analyzed by flow cytometry for HLA-DR, CD86, CD70 ad CD83 expression (A). Supernatants were collected and analyzed for IL-12 expression using ELISA (B).

Figure 7:
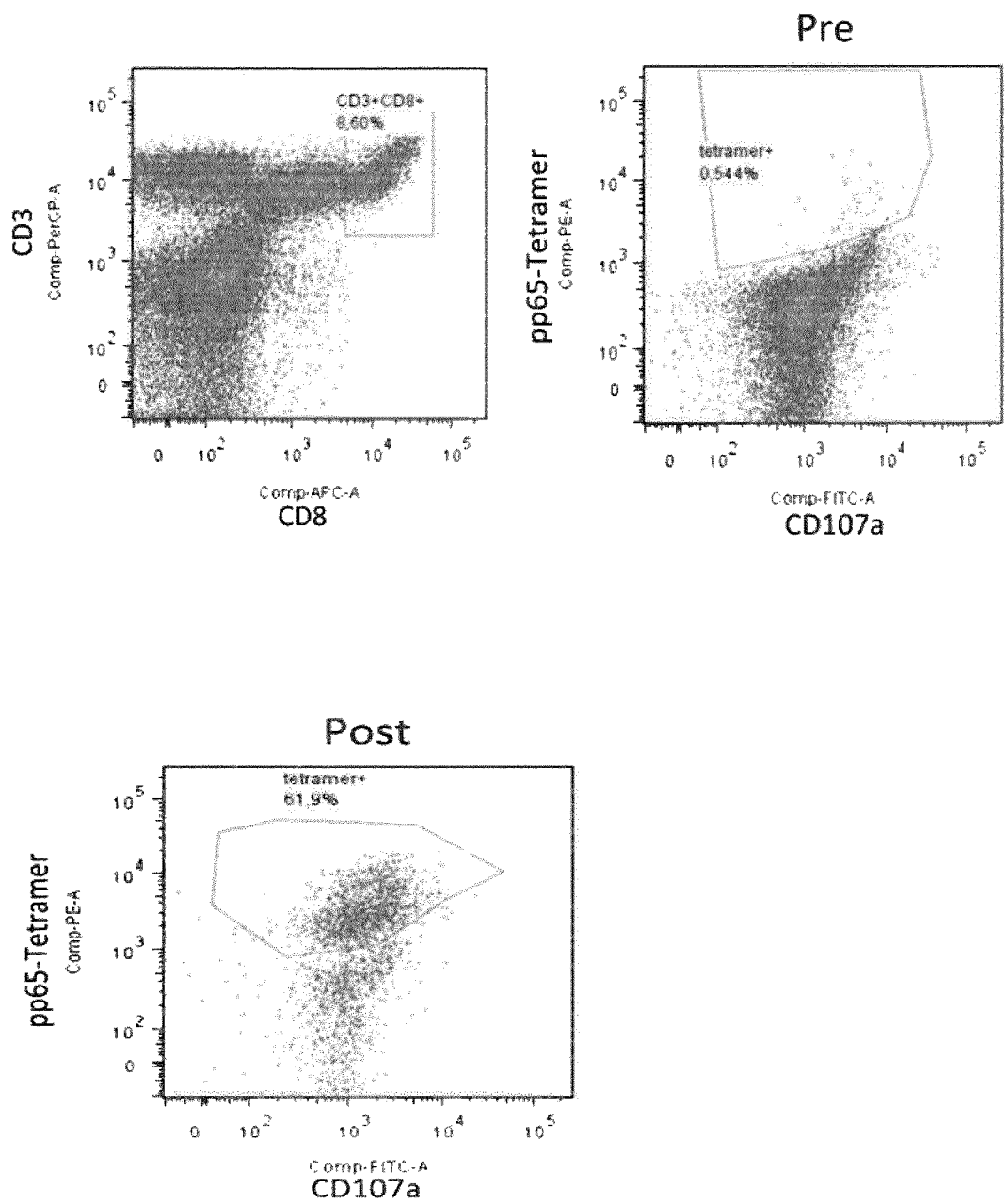

FIG. 7: CD14-mononuclear cells from a CMV+ donor were cultured with dendritic cells transduced with the Ad5/35-TMZ-CD154 virus and pulsed with CMV pp65 peptides for 11 days. At day 11 the cells were analyzed for the presence of CD3+CD8+tetramer+ CMV-specific T cells by flow cytometry. Only 0.5% of the T cells were CMV-specific pre culture and post culture more than 60% of the T cells were CMV-specific.

Figure 8:
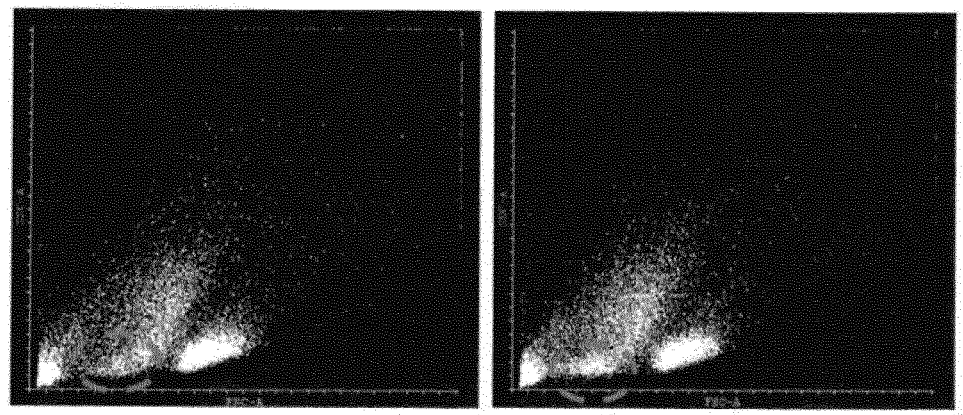
Figure 8:
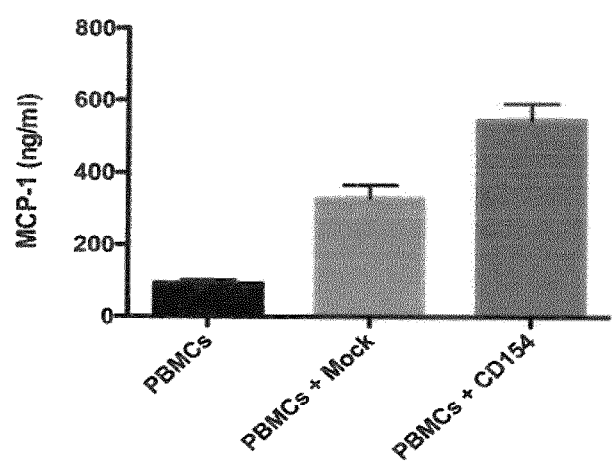

FIG. 8: Mononuclear cells from horse were transduced with and adenoviral vector with the human CD154 gene and cultured. After a week, the lympocyte population was expanded (A, right) compared to Mock transduced cells (left). Supernatants were harvested and analyzed using an anti-horse MCP-1 ELISA. Mock virus activates MCP-1 but CD154 virus gives an improved expression.

Figure 9:
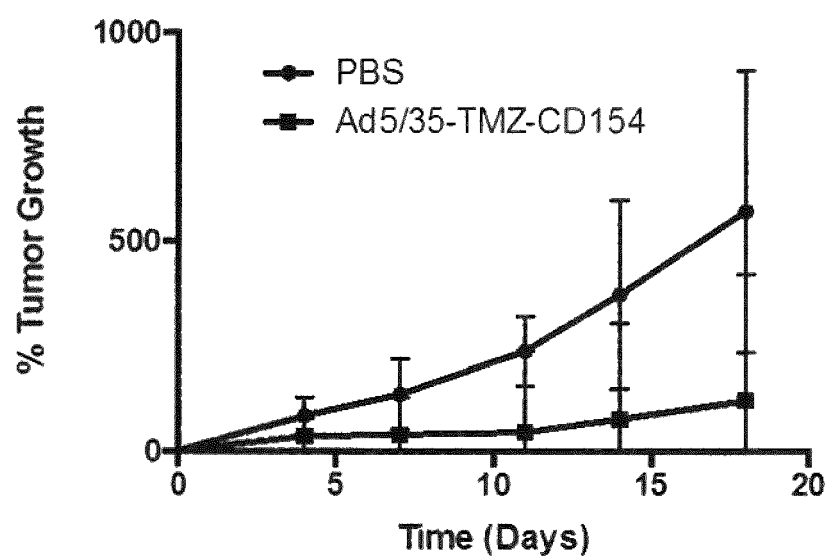

FIG. 9: The Panc01 cell line was grown subcutaneously in Nu/Nu mice lacking a functional immune system. The tumors were injected ix with 1×10e9 VP oncolytic adenovirus expressing the TMZ-CD154 or PBS. The % tumor growth is shown during time from viral injection.

Figure 10:
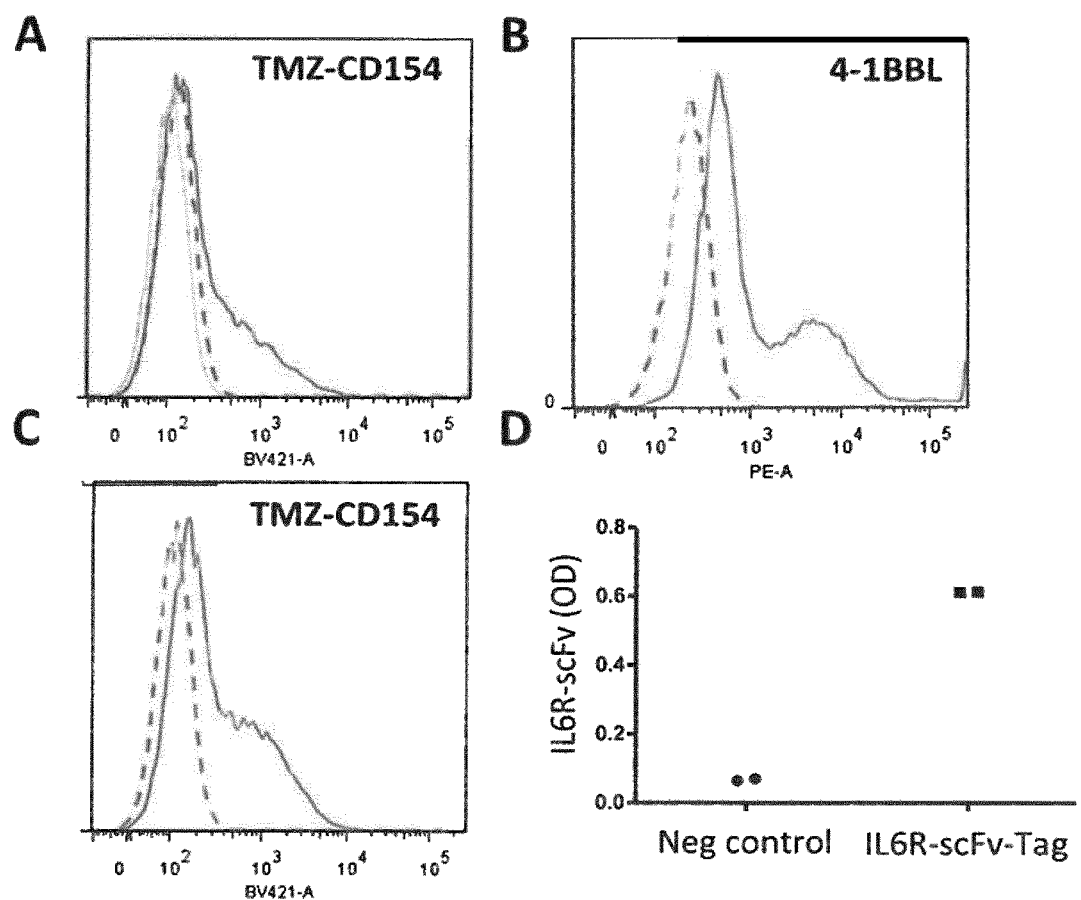

FIG. 10: 293 cells were transfected with plasmids containing TMZ-CD154 in combination with 4-1BBL (A, B) or aIL6R scFv (C,D) and analyzed for the expression of CD154 (A, C) or 4-1BBL (B) by flow cytometry. Supernatant from cells expressing the aIL6R scFv with a myk-Tag was analyzed by ELISA to determine the expression of aIL6R (D).

Figure 11:
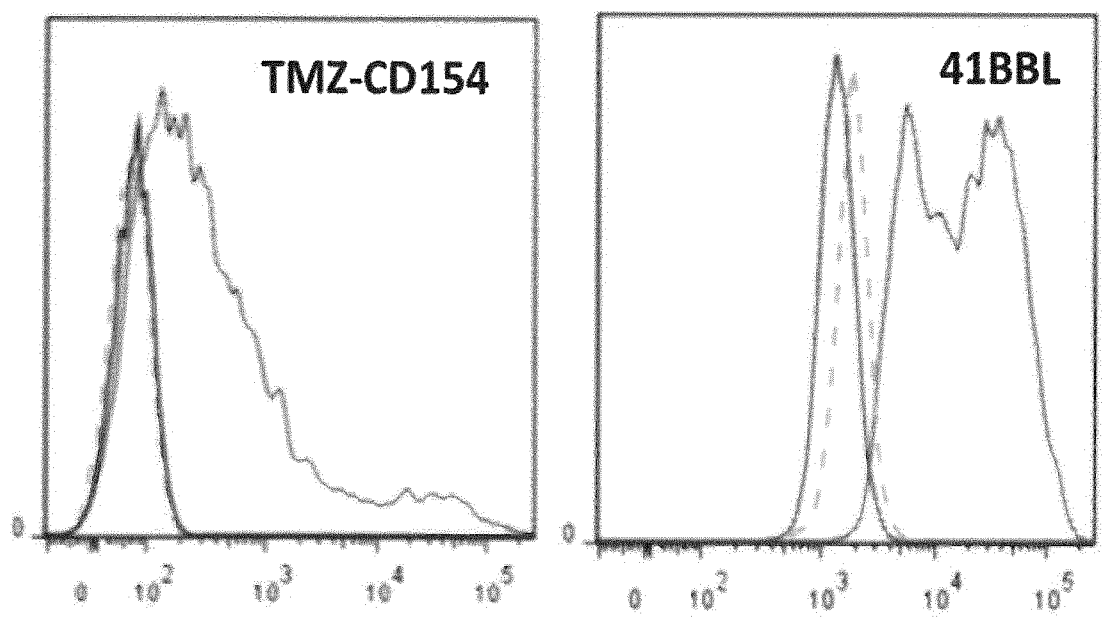

FIG. 11: DCs were transduced with Ad5/35 virus with TMZ-CD154 in combination with 4-1BBL or cells were left untransduced or transduced with an empty Mock virus. After two days of co-culture the cells were analyzed for the expression of TMZ-CD154 and 4-1BBL by flow cytometry.

Figure 12:
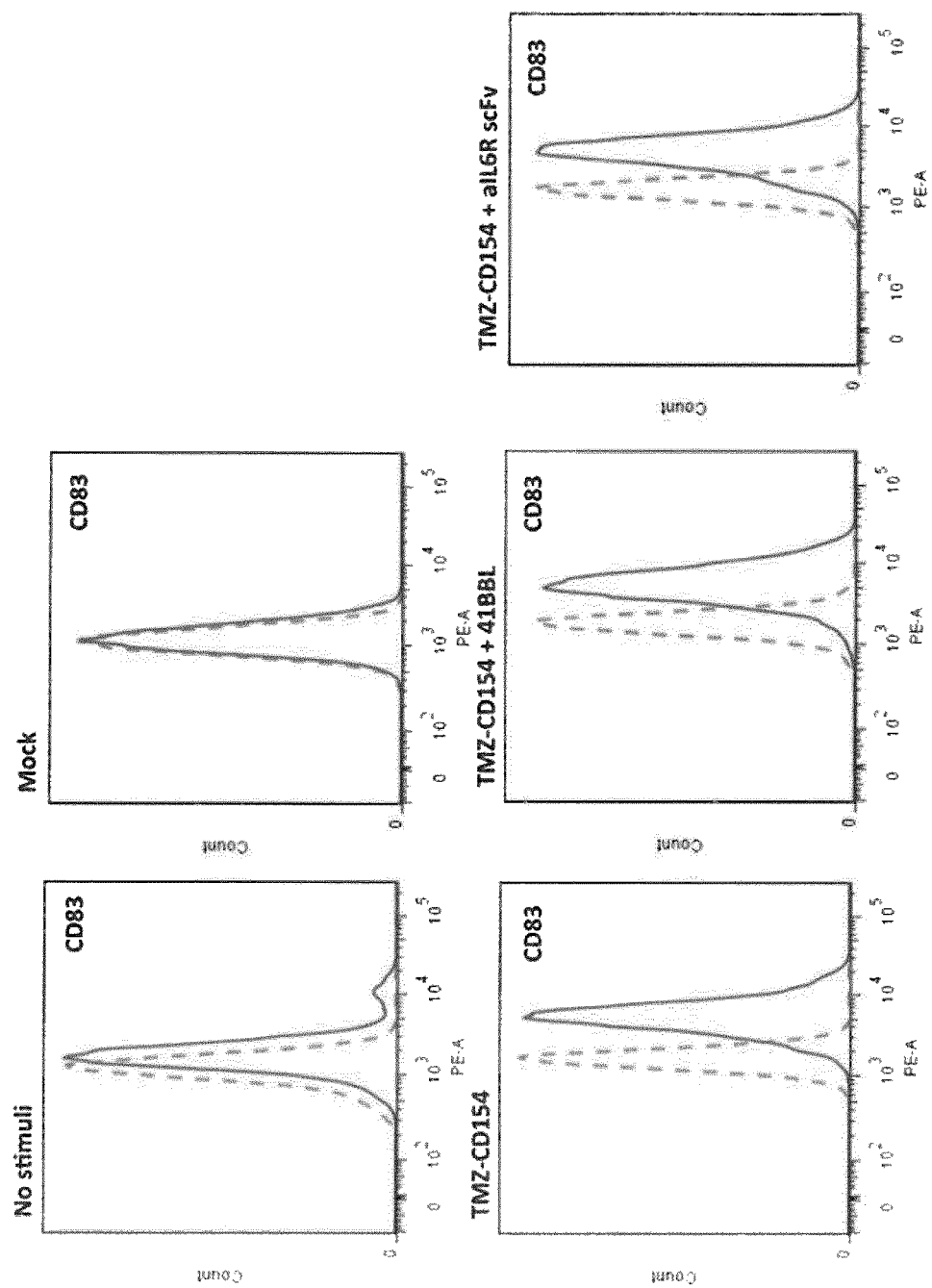

FIG. 12: Human immature dendritic cells were transduced with Ad5/35 virus with TMZ-CD154 alone or in combination with 4-1BBL or aIL6R scFv, or the cells were left untransduced or transduced with an empty Mock virus. After two days of co-culture the cells were analyzed for the expression of CD83 by flow cytometry.

Figure 13:
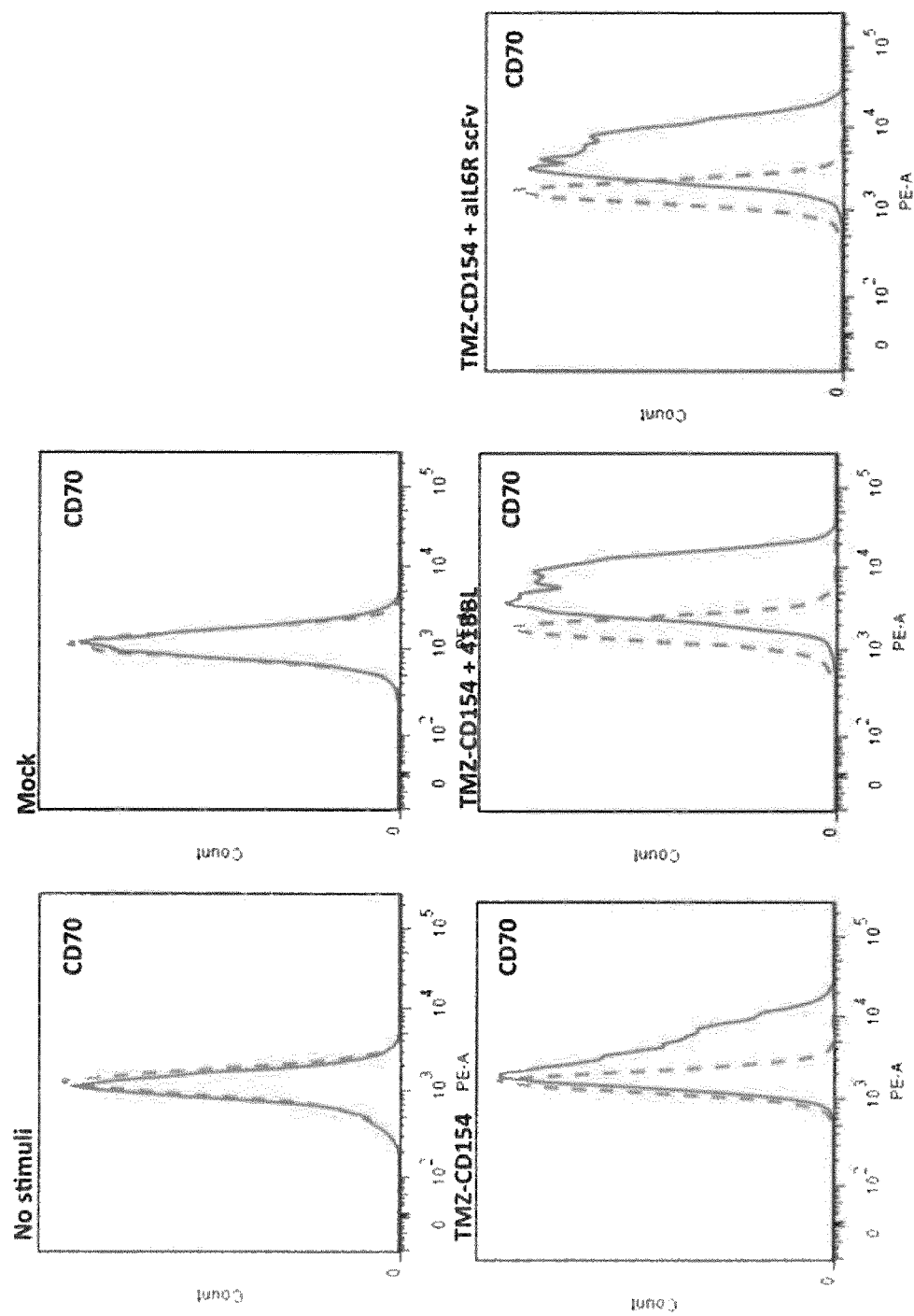

FIG. 13: Human immature dendritic cells were transduced with Ad5/35 virus with TMZ-CD154 alone or in combination with 4-1BBL or aIL6R scFv, or the cells were left untransduced or transduced with an empty Mock virus. After two days of co-culture the cells were analyzed for the expression of CD70 by flow cytometry.

Figure 14:
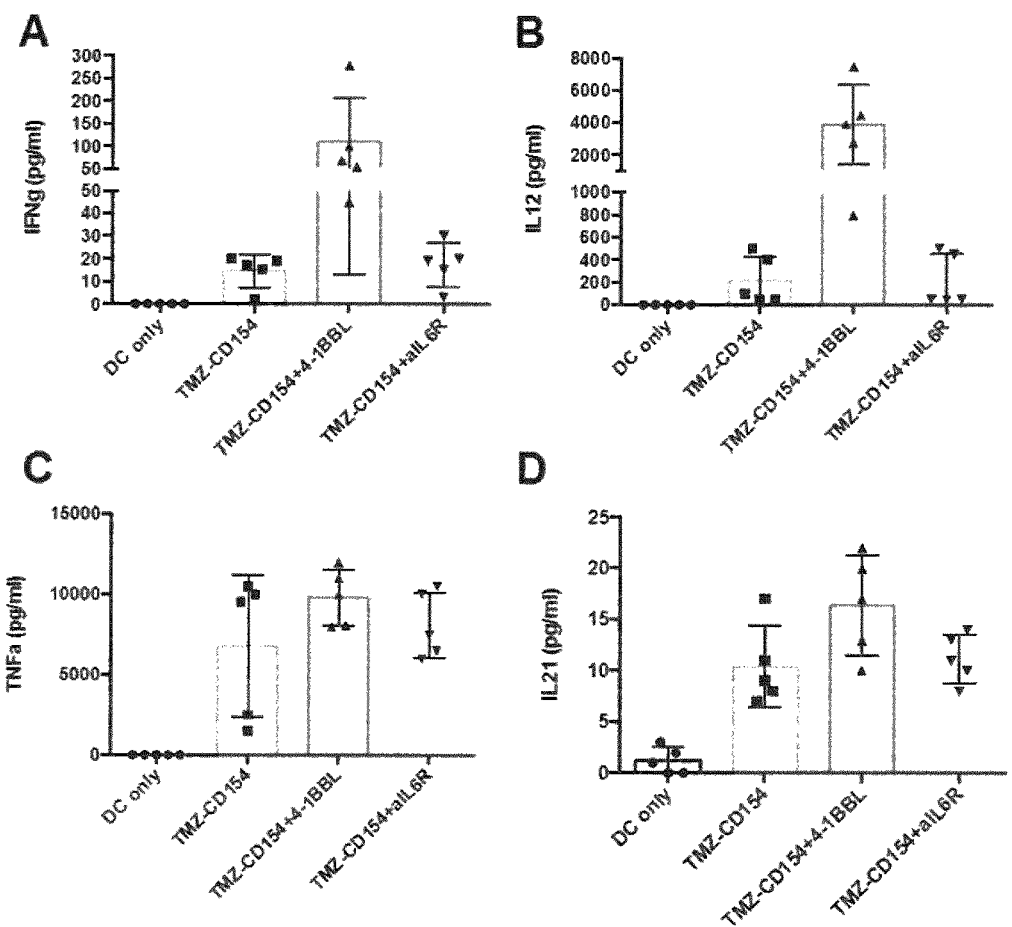

FIG. 14: Human immature dendritic cells were transduced with Ad5/35 virus with TMZ-CD154 alone or in combination with 4-1BBL or aIL6R scFv, or the cells were left untransduced. After two days of co-culture the supernatants were analyzed by luminex to compare the levels of IFNg (A), IL12 (B), TNFa (C) and IL21 (D) between the groups.

Figure 15:
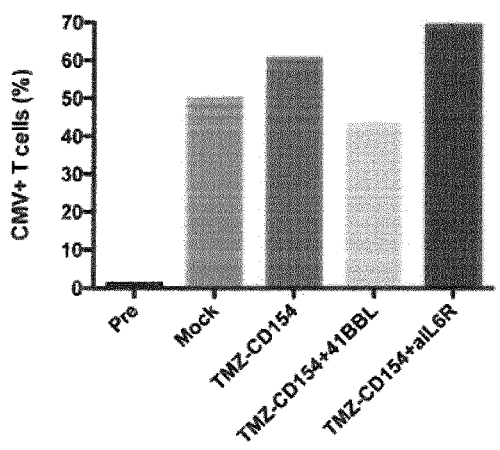
Figure 15:
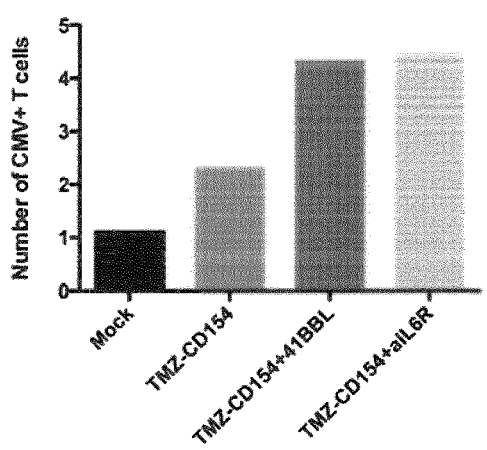
Figure 15:
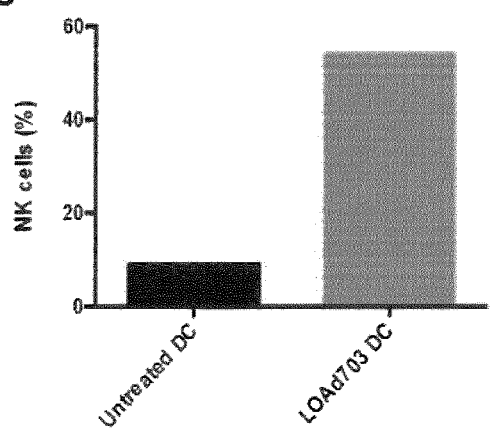

FIG. 15: CMV-specific T cells were expanded from mononuclear cells prepared from a CMV positive blood donor by expanding CD14− cells with transduced dendritic cells pulsed with CMV pp65 peptides. The dendritic cells were transduced with a Mock virus, the Ad5/35 virus with TMZ-CD154 alone or in combination with 4-1BBL or aIL6R. At day 11, cells were harvested and analyzed for the percentage of tetramer positive (CMV-specific) T cells using flow cytometry and compared to the pre-expansion value in A. In B, the total number of expanded cells in the different groups is shown. Ad5/35 virus that contained both TMZ-CD154 and 4-1BBL (LOAd703) could also expand NK cells in the cultures (C).

Figure 16:
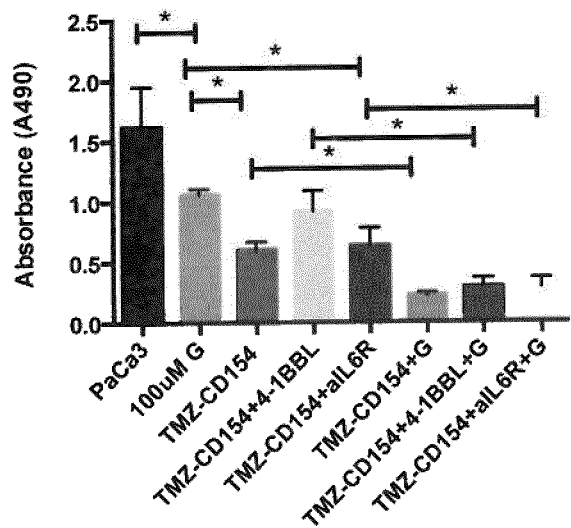
Figure 16:
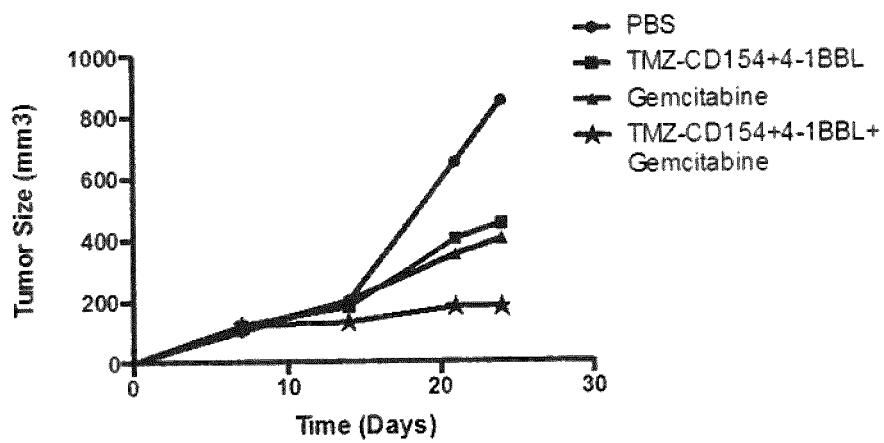
Figure 16:
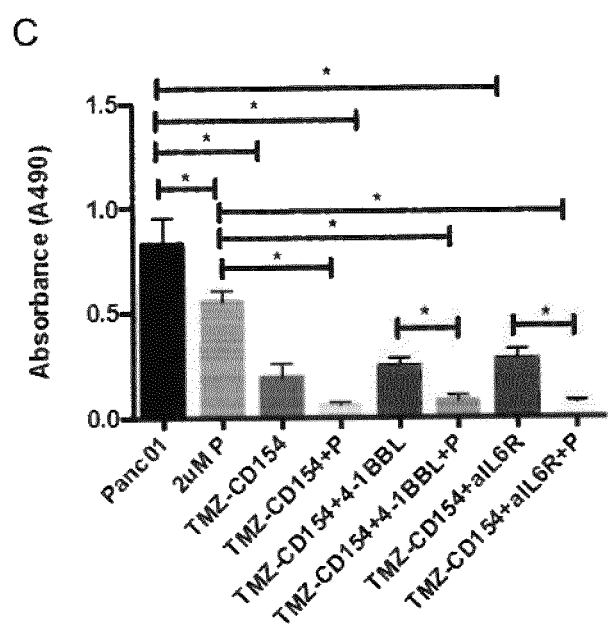

FIG. 16: The pancreatic cell line PaCa3 was cultured alone or with 100 uM gemcitabine (G). PaCa3 cells were also transduced with Ad5/35 viruses expressing TMZ-CD154 alone or in combination with 4-1BB ligand or aIL6R scFv. Finally, transduced cells were cultured with 100 uM gemcitabine. Cells were seeded into 96 well plates and analyzed for survival using the MTS viability assay to determine the level of cell death by oncolysis, by gemcitabine, or by the combination of oncolysis and gemcitabine. * indicates p<0.05 differences. B) Panc02 murine pancreatic tumor cells were grown in C57BL6 mice and treated with an oncolytic adenovirus carrying TMZ-CD154+4-1BBL twice weekly 6x+/− weekly (3x) gemcitabine (25 mg/kg). Tumor growth is shown. C) Panc01 human pancreatic cells were transduced as in (A) above and cultured with or without paclitaxel (2 uM). * indicates p<0.05 differences.

Figure 17:
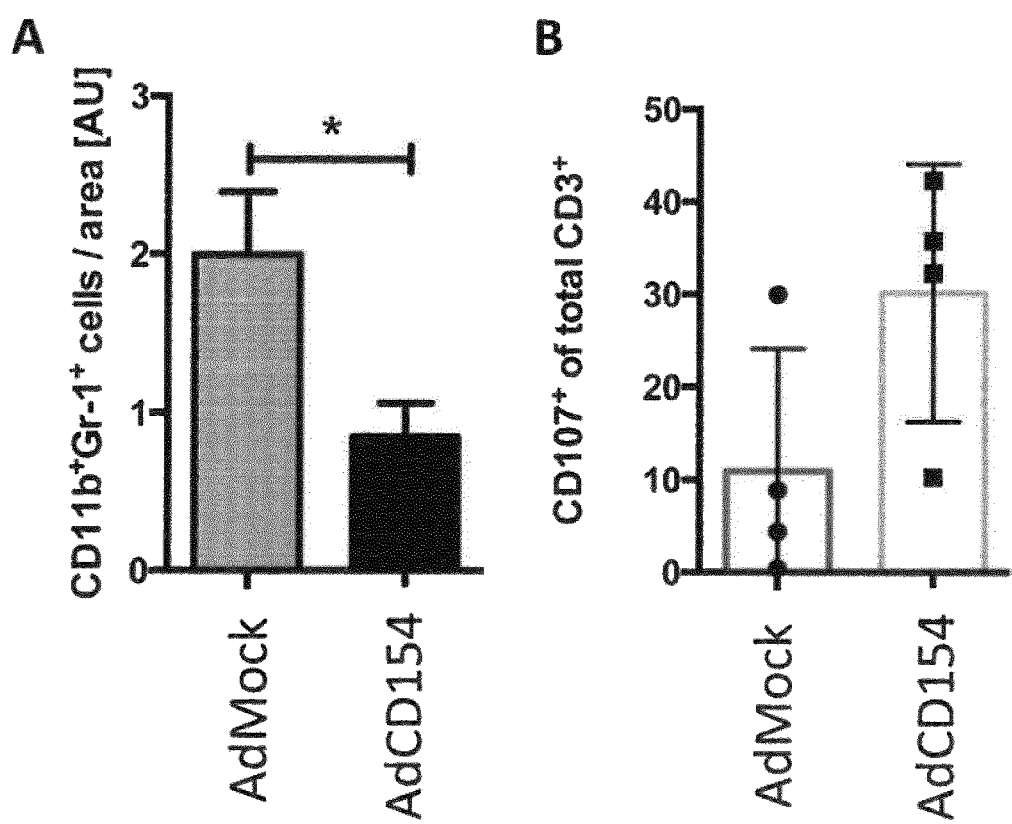

FIG. 17: CD C57BL/6 mice with growing MB49 bladder cancer tumor cells were treated with 1 intratumoral infusion of an adenovirus vector carrying the murine CD154 gene. 24 hours later biopsies were taken for immunohistochemistry detecting CD1 1 b and GR-1 cells by confocal microscopy (A) and for flow cytometry post mechanical disrup-tion into single cell suspension detecting CD3+CD107a+ tumor-infiltrating T cells (B).

Figure 18:
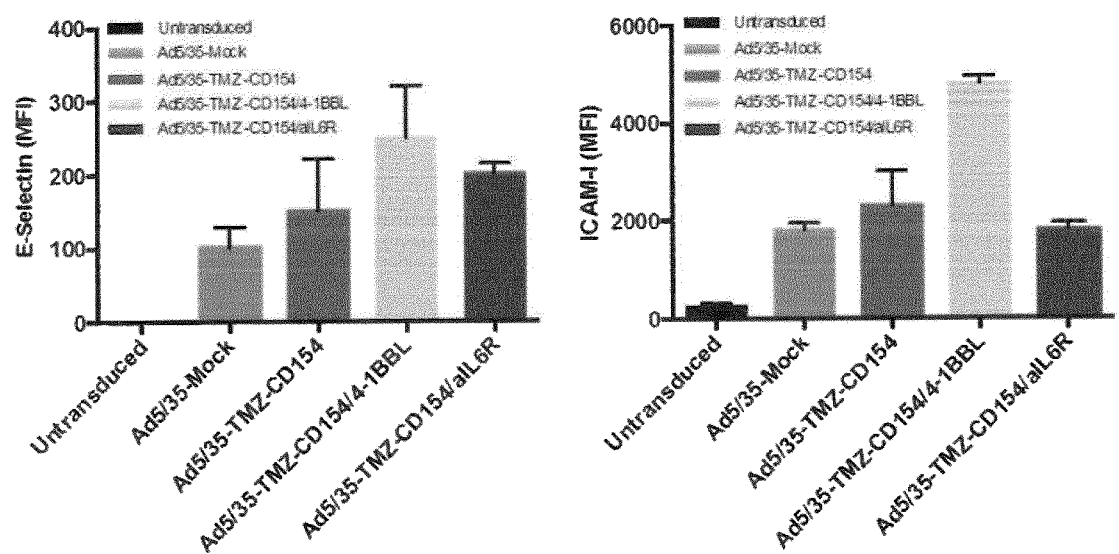

FIG. 18: Human endothelial cells (HUVEC) were transduced with Ad5/35 viruses containing TMZ-CD154 with and without either 4-1BBL or aIL6R, or a virus without transgenes (Mock), or left untransduced. After 48 hrs of culture the cells were analyzed by flow cytometry for the expression of E-selectin and ICAM-I that are important for lymphocyte attachment and diapedes via endothelium into inflamed tissues.

Figure 19:
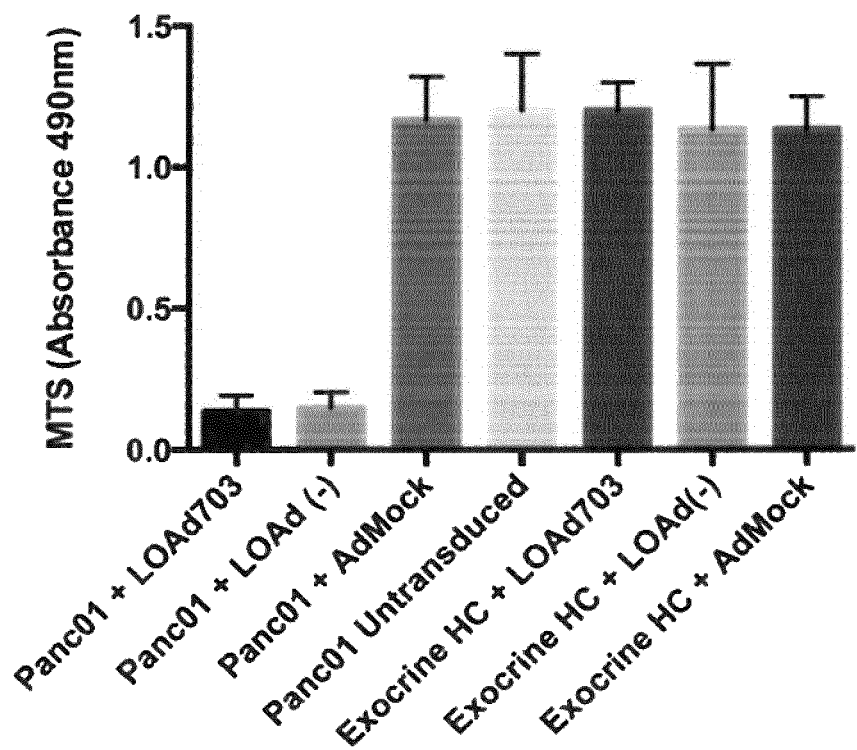

FIG. 19: Oncolysis is restricted to tumor cells. Tumor cells (Panc01 is demonstrated in the Figure) and healthy control exocrine pancreatic cells were transduced with LOAd703, a LOAd (−) virus that lacks transgenes, and Ad5/35 Mock virus that lack ability to replicate via E1/E3 deletion, or left untransduced. The cells were cultured in replicates in 96-well plates and analyzed for viability using MTS assay. Low viability gives low absorbance.

Figure 20:
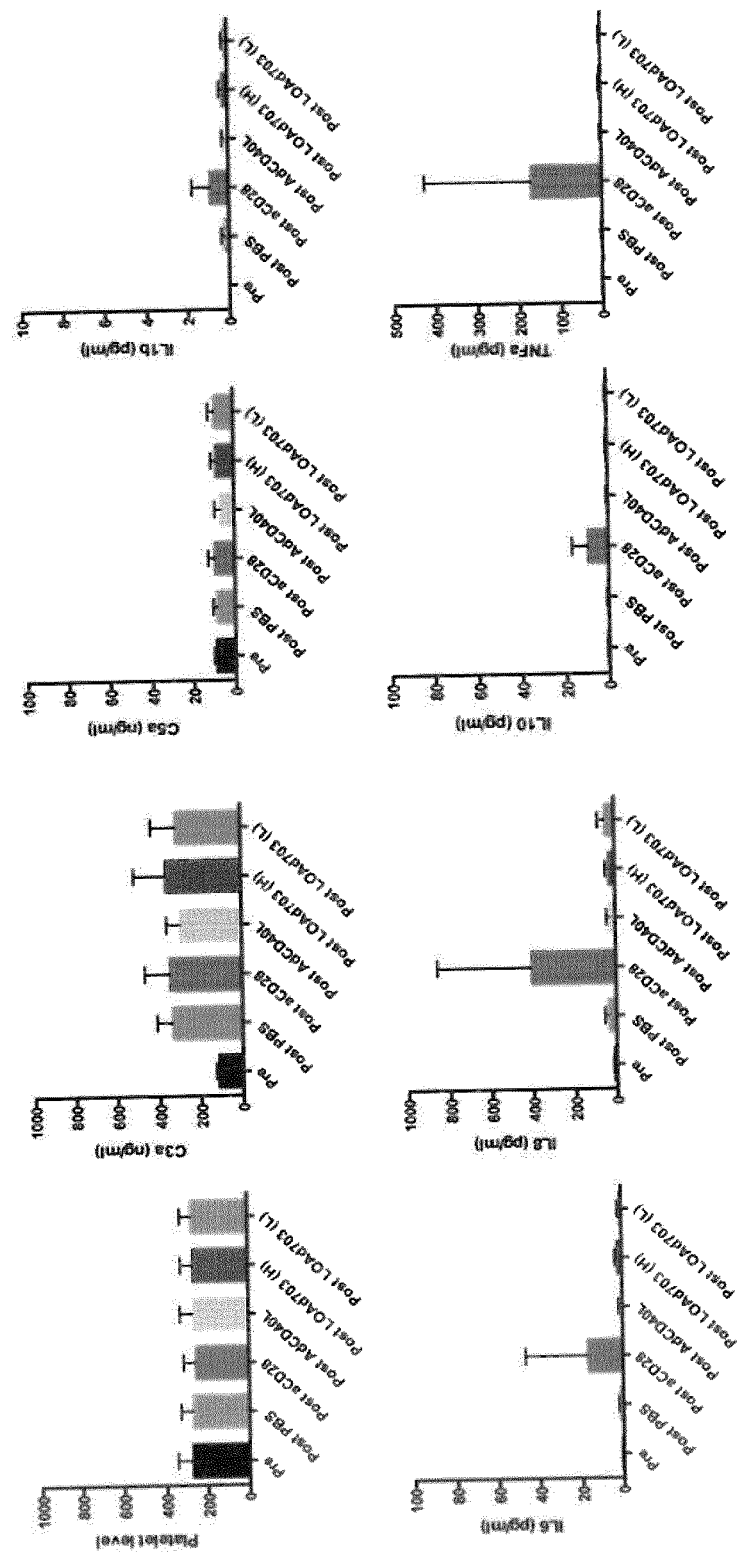

FIG. 20: Toxicity test in the blood loop model. Blood from 5 healthy donors were tested for the reactivity to LOAd703. Blood was circulating in heparinized loops (2 ml/loop) that do not affect complement for four hours. Plasma samples were taken before assay and 4 hours after addition of LOAd703 at high dose (1×10e8 VP) or low dose (1×10e7 VP). As negative control, PBS was added to the loop and an anti-CD28 antibody was used as a positive control. AdCD40L is a similar virus to LOAd703 that has been used clinically and was tested at high dose (1×10e8 VP).

Figure 21:
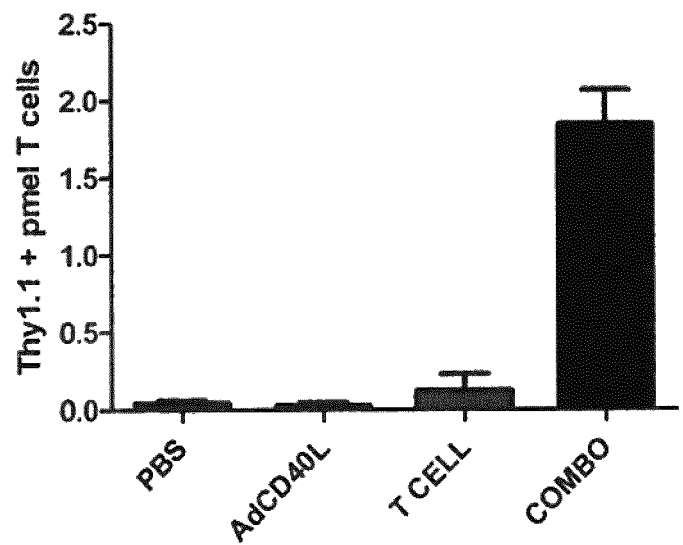
Figure 21:
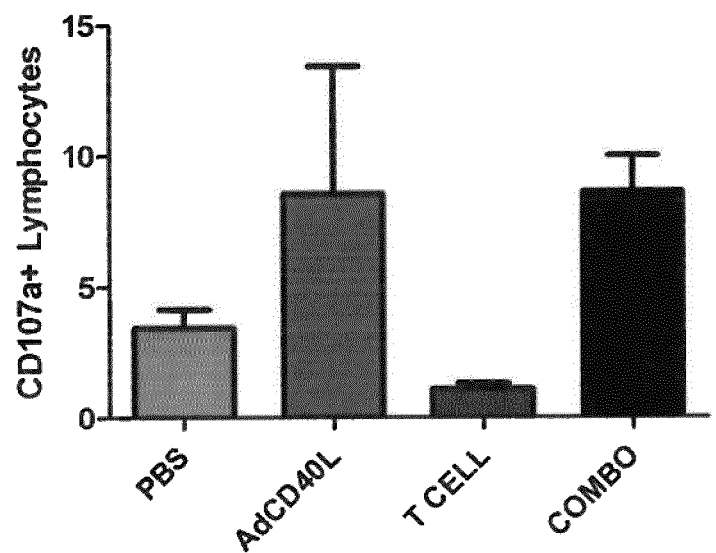

FIG. 21: B16 tumors growing subcutaneously in C57BL6 mice were treated with AdCD40L where after pmel T cells recognizing B16 tumors were infused. The tumors were then analyzed by flow cytometry for the presence of T cells. A) pmel T cells could infiltrate the tumor, however, if the tumor was pretreated with AdCD40L (combo) the infiltration of pmel T cells was dramatically increased. B) In the AdCD40L treated tumors, both natural and pmel T cells were increased compared to tumors that were not AdCD40L pretreated and they expressed the activation marker CD107a.

Figure 22:
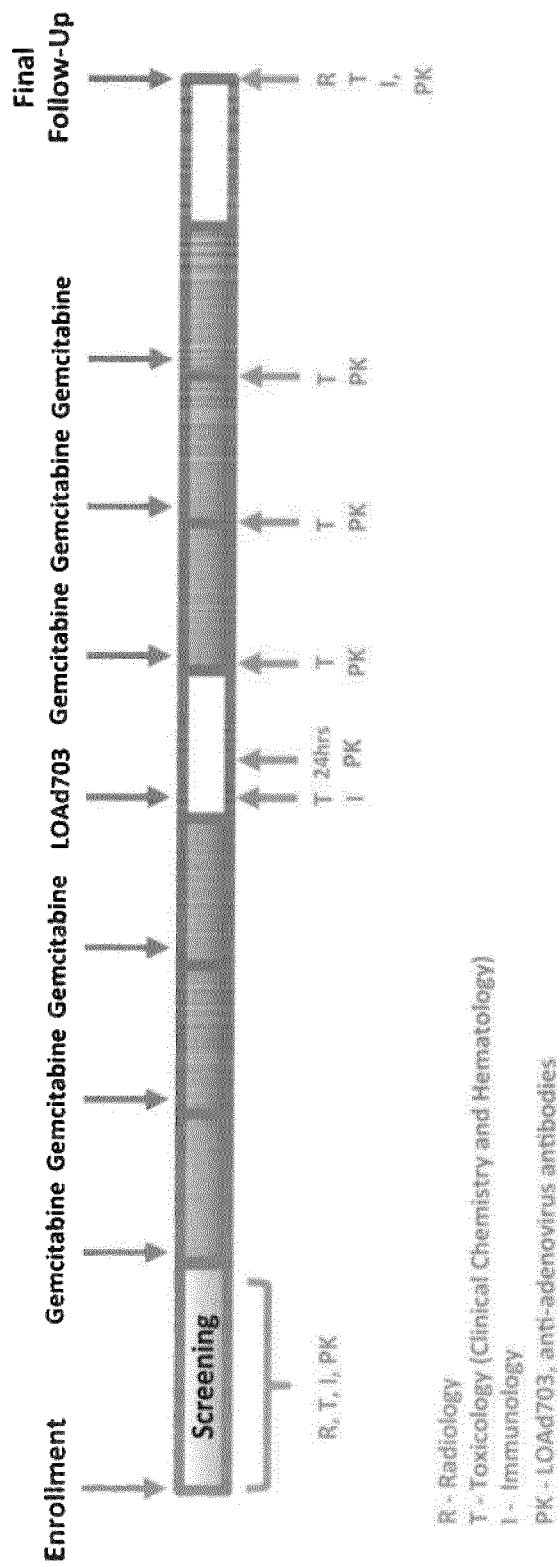

FIG. 22: Treatment schedule for single dose therapy using Ad5/35-TMZ-CD154/4-1BBL (LOAd703) at dose level one 1×10e11 VP and dose level two 5×10e11 VP. Blue and white boxes represents 1 week.

Figure 23:
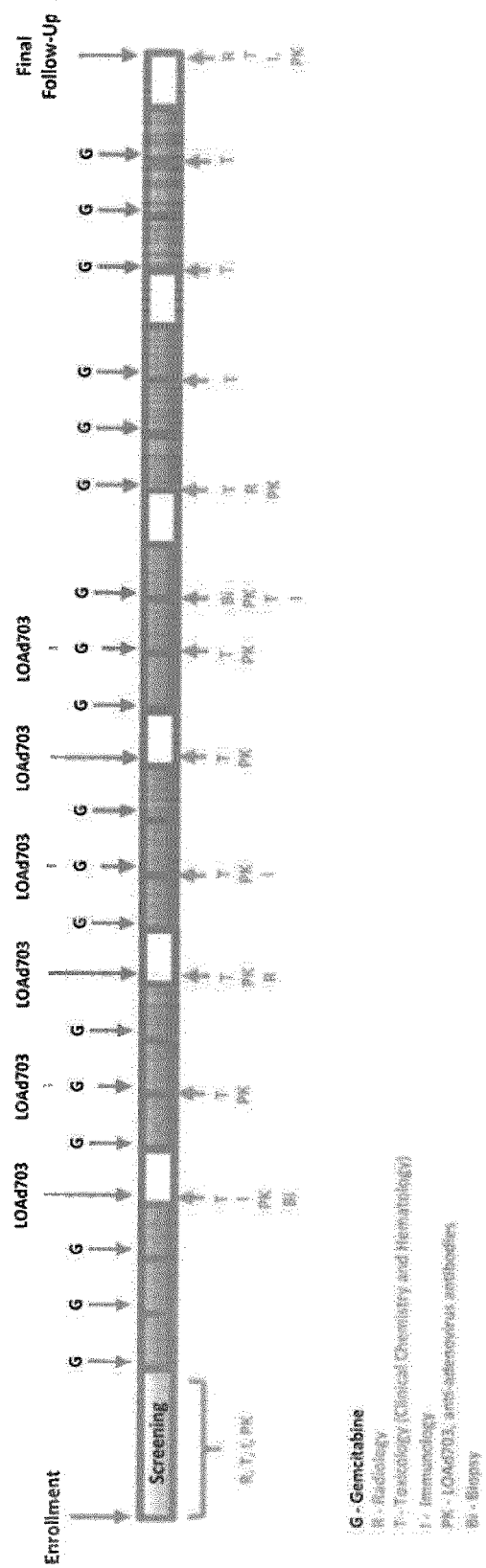

FIG. 23: Treatment schedule for repeat dose therapy using Ad5/35-TMZ-CD154/4-1BBL (LOAd703) at dose level 5×10e11 VP. Blue and white boxes represents 1 week.

The invention is illustrated in the following, non-limiting examples.

EXAMPLES

Material and Methods

TMZ-CD154 Gene Sequences

To exemplify the gene sequence of a TMZ-CD154 molecule as defined herein we have constructed such TMZ-CD154 gene sequences for human, horse, dog and cat.

```
SEQ ID NO: 1 (DNA), SEQ ID NO: 2 (protein)
Human
Human Trimerized Membrane-Bound CD154
1-9       Kozak sequence
10-108    Isoleucine Zipper
109-126   Linker
127-198   Transmembrane domain human CD154
199-846   Extracellular domain human CD154
Amino acid sequence for tm and ec domains of CD154 is labelled in grey 1   GCCACCATGA GAATGAAGCA GATCGAGGAC AAGATCGAGG AGATCCTGAG    Frame 1
              M   R   M   K   Q   I   E   D   K   I   E   E   I   L   S 51   CAAGATCTAC CACATCGAGA ACGAGATCGC CAGAATCAAG AAGCTGATCG    Frame 1
            K   I   Y   H   I   E   N   E   I   A   R   I   K   K   L   I   G 101   GCGAGAGAGG CGGCCGGGGC GGCGGCATTT TTATGTATTT ACTTACTGTT    Frame 1
            E   R   G   G   R   G   G   G   I   F   M   Y   L   L   T   V 151   TTTCTTATCA CCCAGATGAT TGGGTCAGCA CTTTTTGCTG TGTATCTTCA    Frame 1
            F   L   I   T   Q   M   I   G   S   A   L   F   A   V   Y   L   H 201   RAGAAGGTTG ACAAGATAG AAGATGAAAG GAATCTTCAT GAAGATTTTG      Frame 1
            R   R   L   D   K   I   E   D   E   R   N   L   H   E   D   F   V 251   TATTCATGAA AACGATACAG AGATGCAACA CAGGAGAAAG ATCCTTATCC    Frame 1
            F   M   K   T   I   Q   R   C   N   T   G   E   R   S   L   S 301   TTACTGAACT GTGAGGAGAT TAAAAGCCAG TTTGAAGGCT TTGTGAAGGA    Frame 1
            L   L   N   C   E   E   I   K   S   Q   F   E   G   F   V   K   D 351   TATAATGTTA AACAAAGAGG AGACGAAGAA AGAAAACAGC TTTGAAATGC    Frame 1
            I   M   L   N   K   E   E   T   K   K   E   N   S   F   E   M   Q 401   AAAAAGGTGA TCAGAATCCT CAAATTGCGG CACATGTCAT AAGTCAGGCC    Frame 1
            K   G   D   Q   N   P   Q   I   A   A   H   V   I   S   E   A 451   AGCAGTAAAA CAACATCTGT GTTACAGTGG GCTGAAAAAG GATACTACAC    Frame 1
            S   S   K   T   T   S   V   L   Q   W   A   E   K   G   Y   Y   T 501   CATGAGCAAC AACTTGGTAA CCCTGGAAAA TGGGAAACAG CTGACCGTTA    Frame 1
            M   S   N   N   L   V   T   L   E   N   G   K   Q   L   T   V   K 551   AAAGACAAGG ACTCTATTAT ATCTATGCCC AAGTCACCTT CTGTTCCAAT    Frame 1
            R   Q   G   L   Y   Y   I   Y   A   Q   V   T   F   C   S   N 601   CGGGAAGCTT CGAGTCAAGC TCCATTTATA GCCAGCCTCT GCCTAAAGTC    Frame 1
            R   E   A   S   S   Q   A   P   F   I   A   S   L   C   L   K   S 651   CCCCGGTAGA TTCGAGAGAA TCTTACTCAG AGCTGCAAAT ACCCACAGTT    Frame 1
            P   G   R   F   E   R   I   L   L   R   A   A   N   T   H   S   S 701   CCGCCAAACC TTGCGGGCAA CAATCCATTC ACTTGGGAGG AGTATTTGAA    Frame 1
            A   K   P   C   G   Q   Q   S   I   H   L   G   G   V   F   E 751   TTGCAACCAG GTGCTTCGGT GTTTGTCAAT GTGACTGATC CAAGCCAAGT    Frame 1
            L   Q   P   G   A   S   V   F   V   N   V   T   D   P   S   Q   V 801   GAGCCATGGC ACTGGCTTCA CGTCCTTTGG CTTACTCAAA CTCTGA        Frame 1
            S   H   G   T   G   F   T   S   F   G   L   L   K   L   *

SEQ ID NO: 3 (DNA)
Horse TZM-CD154 (bold CD154 domain)
gccaccatgagaatgaagcagatcgaggacaagatcgaggagatcctgagcaagatctaccacatcgagaacgagatcgccagaatcaagaagctgatcggcgagagaggcggccggggcggcggcatttttatgtatttgct-
``` tactgtttttcttatcacccagatgattgtgtcagcacttttgctgtgtatcttcacagaagattggacaagatagaagatgaaaggaatcttcatgaagattttgtgttcatgaaaacgatacagagatgcaacaaaggagaggggcctttatcattactgaactgtgaggaaattagaagccagttcgaaggcttcgtcaaggatataatgctaaatgaagaagtgaagaagaaggagaaaactttgaaatgcaaaaaggcgatcaggagcctcaaattgcggcacatgtcataagtgaggccagcagtaaaacagcatctgttctacagtgggcccaaaaaggatactacaccataagcaacaacttggtaaccctcgaaaatgggaaacagctggccgttaaaagacaaggactctattatatctatgcccaagtcaccttctgttccaatcgggaagcttcgggtcaagctccatttatagccagcctctgcctgaggtccgtgagtggatctgagagaatcttacttagagcggcaaatacccacagttcctccaaaccttgcgggcagcaatccattcacttgggaggagtatttgaattgcaaccaggtgcttcggtgtttgtcaacgtgactgatccaagccaagtgagccatgggaccggcttcacatcttttggtttactcaaactctga SEQ ID NO: 27 (protein)
TMZ-CD154 Horse amino acid sequence A T M R M K Q I E D K I E E I L S K I Y H I E N E I A R I K K L I G E R G G R G G G
F M Y L L T V F L I T Q M I V S A L F A V Y L H R R L D K I E D E R N L H E D F V F
M K T I Q R C N K G E G P L S L L N C E E I R S Q F E G F V K D I M L N E E V K K
K G E N F E M Q K G D Q E P Q I A A H V I S E A S S K T A S V L Q W A Q K G Y Y
T I S N N L V T L E N G K Q L A V K R Q G L Y Y I Y A Q V T F C S N R E A S G Q A
P F I A S L C L R S V S G S E R I L L R A A N T H S S S K P C G Q Q S I H L G G V F
E L Q P G A S V F V N V T D P S Q V S H G T G F T S F G L L K L SEQ ID NO:4 (DNA)
Dog TZM-CD154 (bold CD154 domain)
gccaccatgagaatgaagcagatcgaggacaagatcgaggagatcctgagcaagatctaccacatcgagaacgagatcgccagaatcaagaagctgatcggcgagagaggcggccggggcggcggcattttatgtatttgcttactgtttttctcatcacccagatgattggatcggcactctttgctgtatatcttcacagaagattggacaagatagaagatgaaaggaatctttatgaagattttgtgttcatgaaaacgttacagaaatgcaacaaaggggaggggtccttgtccttactgaactgtgaggaaattaaaagccaatttgaagcctttctcaaggagataatgctaaacaacgaaatgaagaagaagaaaacattgcaatgcaaaaaggtgatcaggatcctcgaattgcagcccatgtcataagtgaggctagtagtaacccagcgtccgttctgcggtgggcgccaaaagggtactacaccataagcagcaacctggtgagcctcgagaatgggaaacagttggccgtgaaaagacaaggactctattacgtctatgcccaagtcaccttctgctccaatcgggcagcttcgagtcaagctccgttcgtcgccagcctatgcctccattccccgagtggaacggagagagtcttactccgcgccgcgagctcccgcggctcgtccaaaccttgcggccaacagtccatccacttggccaacagtccatccacttgggaggagtatttgaattgcatccaggtgcttcggtgttcgtcaacgtgactgaggagtatttgaattgcatccaggtgcttcggtgttcgtcaacgtgactgatccaagccaagtgagccacgggaccggcttcacgtcttttggcttactcaaactctgaa

SEQ ID NO: 28 (protein)
TMZ-CD154 Dog amino acid sequence

ATMRMKQIEDKIEEILSKIYHIENEIARIKKLIGERGGRGGG
PMYLLTVFLITQMIGSALFAVYLHRRLDKIEDERNLYEDFVF
MKTLQKCNKGEGSLSLLNCEEIKSQFEAFLKEIMLNNEMKK
EENIAMQKGDQDPRIAAHVISEASSNPASVLRWAPKGYYTI
SSNLVSLENGKQLAVKRQGLYYVYAQVTPCSNRAASSQAP
FVASLCLHSPSGTERVLLRAASSRGSSKPCGQQSIHLGGVF
ELHPGASVFVNVTDPSQVSHGTGFTSFGLLKL

SEQ ID NO: 5 (DNA)
Cat TZM-CD154 (bold CD154 domain)
gccaccatgagaatgaagcagatcgaggacaagatcgaggagatcctgagcaagatctaccacatcgagaacgagatcgccagaatcaagaagctgatcggcgagagaggcggccggggcggcggcattttatgtatttacttactgtgtttctcatcacccagatgattgggtcagcactctttgtgtgtatcttcacagaagactggacaagatagaagatgaaaggaatctttatgaagattttgtgttcatgaaaacattacagaaatgcaacaaaggagaggggggccttatcccttactgaactgtgaggaaattaaaagccggtttgaagcctttctcaaggagataatgctaaacaaagaaacgaagaaagaaaaaaatgttgcaatgcaaaaaggcgaccaggatcctcgagttgcagcacatgtcataagtgaggccagcagtagcacagcgtctgttctccagtgggcccccaaaggctactacaccataagcagcaacttggtgaccctcgagaacgggaagcagctggccgttaaaagacaaggactctattagacaaggactctattatatatctacgcccaagtcaccttctgttccaatcgggaagcttcgagtcaagctccgttcatagccagcctctgcctg cattccccgagtggatccgagagagtcttactcagagctgcaaatgcccgcagttcctccaaacctgtgggcagcaatccattcacttgggaggagtcttcgaactgcatccaggtgcttcggtgttcgtgaacgtgactgatccgagccaagtgagccacgggacgggcttcacgtcttttggcttactcaaactctgaa SEQ ID NO: 29 (protein)
TMZ-CD154 Cat amino acid sequence ATMRMKQIEDKIEEILSKIYHIENEIARIKKLIGERGGRGGG
PMYLLTVFLITQMIGSALFAVYLHRRLDKIEDERNLYEDFVF
MKTLQKCNKGEGALSLLNCEEIKSRFEAFLKEIMLNKETKK
EKNVAMQKGDQDPRVAAHVISEASSSTASVLQWAPKGYYT
ISSNLVTLENGKQLAVKRQGLYYIYAQVTPCSNREASSQAP
FIASLCLHSPSGSERVLLRAANARSSSKPCGQQSIHLGGVF
ELHPGASVFVNVTDPSQVSHGTGFTSFGLLKL Plasmid Construction The gene sequences were constructed using the free pDraw32 software by AcaClone and then synthesized with a CMV promoter ahead of the 5' gene and Adenovirus flanking regions (also containing the restriction sites 5'SspI and 3'ScaI) for homologous recombination into adenoviral vectors at both ends. Post the 3' Ad flanking region a Poly A site was synthesized when gene expression was achieved with plasmid transfection. The gene fragments were synthesized and sub-cloned into a pUC57-Kan plasmid at GenScript Inc.

Adenoviral Vector Construction

The pUC57 plasmids with transgene cassettes were digested with SspI and ScaI enzymes and the band was isolated by standard gel electrophoresis and purification. The gene cassettes were inserted into an adenoviral backbone plasmid by homologous recombination. Colonies with correct insert were expanded and the gene sequences confirmed with restriction pattern analysis and sequencing. Adenoplasmids with the gene cassettes were transfected into 293 cells to generate viruses. Plaque assays were performed on A549 cells to generate single virus clones. Viruses were amplified further on A549 cells and purified with CsCl gradient centrifugation. The final viral particles were formulated in 20 mM TRIS, 25 mM NaCl and 2.5% Glycerol. Physical (O.D) titer and functional titer (anti-hexon staining) were determined.

Cell Lines

The cell lines HEK 293, B16 and A549 were purchased from ATCC while Karpas 422, PancO1, MiaPaCa2, PaCa3 and BxPC3 were a kind gift from the Karolinska Institute. The MB49 cell line was a gift from National University Hospital Singapore. 293 cells were cultured in DMEM-based medium (10% FBS, 1% Pest Streptomycin, 0.1% Sodium pyruvate) from Life Technologies. A549 are grown in Roswell Park Memorial Institute (RPMI) 1640 Medium GlutaMAX™ Supplement with 10% FBS, 1% PeSt, 1% HEPES and 0.1% Sodium Pyruvate. MiaPaca2 and PanC01 are grown in DMEM with 10% FBS and 1% PeSt. BxPC3 are grown in RPMI 1640 Medium GlutaMAX™ Supplement with 1% FBS and 1% Pest. All components of the cell growth mediums were from Life Technologies.

Buffy Coat Preparation

Buffy coats were purchased from the Uppsala University Hospital Blood Bank. Mononuclear cells were prepared by ficoll centrifugation. Briefly, the buffy was diluted 1:1 with phosphate-buffered saline (PBS) and gently added to 50 mL Falcon tubes containing 10 mL of ficoll without the two layers mixing. The tubes were centrifuged at 1500 rpm for 20 min without break. The white blood cell layer was then transferred by pipetting to fresh tubes and washed with PBS centrifugation. The prepared cells was used fresh or frozen in liquid nitrogen tanks in DMSO-containing freezing medium for future use.

Preparation of Immature Dendritic Cells

CD14+ monocytes were sorted from mononuclear cells from buffy coat preparations using the MACS bead system CD14 MicroBeads according to protocol from the manufacturer (Miltenyi Biotech). CD14− cells (including T cells) were frozen. The CD14+ cells were then diluted in RPMI-culture medium (10% FBS, 1% Pencillin/Streptamycin) to a concentration of 1×10e6 cells/mL. GM-CSF and IL-4 was added to a final concentration of 50 ng/mL and 25 ng/mL, respectively. Fresh medium with GM-CSF and IL-4 was added every other day for one week. After one week of culture the monocytes were differentiated into immature CD14-CD1a+ dendritic cells.

Stimulation of T Cells

Peripheral blood mononuclear cells were stimulated with OKT-3 (anti-CD3) antibodies (1 ug/ml) and IL2 (100 U/ml). Day 3, T cells have expanded and were transduced with adenoviral vectors as described below and cells were cultured with or without fresh IL2 for 48 hrs.

Transfection Using Plasmids 293 cells were washed with PBS centrifugation (1500 rpm, 5 min). The cells (0.75×10e6/group) were resuspended in medium and seeded in 6 well plates and cultured overnight. The next day, 5 ug plasmid was mixed into a suspension of 8 uL polyethylenimine in 100 uL OptiMEM (Life Technologies) and incubated for 20 min. The plasmid-suspension was then dropped into the wells with 293 cells. The cells were cultured for different time points for FACS analysis, supernatant harvest and for co-cultures with immature dendritic cells.

Transduction Using Adenoviral Vectors

Cells to be transduced with adenoviral vectors were washed in serum-free medium. 1×10e6 cells were added per conical 10 mL tube and were centrifuged at 1500 rpm for 5 min. The supernatant was discarded and the cells resuspended in the remaining medium of approximately 150 uL per tube. Adenoviruses ranging from 25-100 ffu/cell were added to the tubes where after they were incubated for 2 hours in 37 C cell incubator with 5% CO2. Cell culture medium with serum was added and the cells were further incubated and used in the different assays (flow cytometry at different time points, gel electrophoresis/Western blot, co-cultures with immature dendritic cells etc).

Flow Cytometry

Cells to be analyzed by flow cytometry were washed in PBS and centrifuged in tubes for flow cytometry (BD Biosciences). The supernatants were removed and the remaining cells resuspended by vortexing. Antibodies or tetramers diluted in 1% bovine serum albumin (BSA) in PBS were added to the cell suspensions and incubated 5 min at room temperature or 30 min at 4 C. Antibodies detecting human CD154, CD83, HLA-DR, CD86, CD70, CD14, CD1a, CD3, CD8, CD107a, and 4-1BB ligand, as well as murine Gr-1, and CD11b were purchased from BioLegend as was irrelevant isotype matched controls. CMV pp65 Tetramers were purchased from Nordic BioSite. The stained cells were washed with 1% BSA in PBS and fixed using 1% paraform aldehyde (PFA) in PBS in a total volume of 300 uL/tube. Cells were analyzed using FACS Canto II from BD Biosciences. Data analysis was performed using FlowJo software from Treestar Inc.

Supernatant Analyses

Supernatants from cell cultures were analyzed for release of human soluble CD154, human IL-12, horse MCP1 and scFv to human IL-6R from untransduced, transduced or transfected cells. sCD154 was analyzed by ELISA using sCD40L Platinum Kit from eBioScience Inc. Horse MCP1 was analyzed using MCP1 Kit from BioLegend. IL-12p70 was detected by a home-made ELISA. Briefly, 96-well plates were coated with 1 ug/mL of purified anti-human IL-12 (p70) antibody from Biolegend overnight at 4° C. Blocking was done by adding PBS with 1% Bovine Serum Albumin (BSA) (Sigma-Aldrich) 1 hr at 37° C. Samples were then incubated in the coated wells for 2 hr at 37° C. after which a biotin anti-human IL-12/IL-23 p40 antibody (Biolegend) was added at a concentration of 1 ug/mL for 1 hr at 37° C. Avidin-conjugated horseradish peroxidase, (Dako A/S) was diluted at 1:4000 and added to the plate for 1 hr at 37° C. in the dark. Development of the assay was done by using TMB (Dako) and reading the absorbance at 450 nm at Emax precision microplate reader (Molecular Devices). The scFv to human IL-6R was analyzed by a home-made ELISA detecting the Myk-Tag inserted into the scFv. Briefly, plates were coated with recombinant human IL-6R and thereafter incubated with samples. After washing with 1% BSA-PBS the plates were incubated with an anti-myk-HRP antibody that could thereafter be detected by adding substrate and peroxidase enzyme (Dako). The color shift was analyzed by spectrophotometry. Further, supernatants were analyzed for multiple cytokines using luminex accordingly to company protocol. A kit detecting the following analytes was used: IFNg, Il12, TNFa and IL21.

Gel Electrophoresis and Western Blot

Lysates were prepared from cells transfected with plasmids as stated above. The cells were washed in ice cold 1×PBS and resuspended in Lysis Buffer containing M-PER mammalian protein extraction reagent supplemented with 1% Halt phosphatase inhibitor cocktail and 1% Protease inhibitor cocktail (Thermo Scientific). The protein concentration of the cell lysates was measured by Coomassie plus protein assay reagent kit according to manufacturer's protocol. 10 ug of samples were loaded onto the gels from BioRad. Samples were mixed in either sample buffer containing mercaptoethanol (reduced) or not (non-reduced). Reduced samples were also boiled for 5 min at 95° C. before loading. The gel was run for 50 min at 110V and the transferred to a membrane using Gel transfer stacks in an iBlot maschine (Life Technologies). The membranes were blocked for 1 hr at room temperature (RT) and then 1:500 diluted CD154 Antibody (H215) (Santa Cruz Biotechnology Inc) was added to the membrane and incubated overnight at 4° C. As a secondary antibody Goat anti-rabbit IgG-HRP (Life Technologies) were used at a dilution of 1:2000 and incubated for 1 hr at RT. The membrane was developed by adding the ECL solution Clarity Western ECL Substrate (BioRad) and the exposing it in V3 Western Workflow™ (BioRad).

Viability Assay

The oncolytic capacity of viruses containing the TMZ-CD154 transgene was determined using the CellTiter 96 Aqueous One Solution Cell Proliferation Assay (MTS) from Promega. The assay was used accordingly to manufacturers protocol. Briefly, tumor cells were transduced with viruses and then seeded into 96-well plates in quadruplicate wells/group, 10 000 cells/well. Healthy donor exocrine cells were obtained from the surplus material of islet cell preparations from the Uppsala university hospital and used as control of restricted tumor cell replication. The plates were cultured and analyzed at different time points 24, 48 and 72 hours post transduction. 20 uL of kit reagent was added and the plate incubated for 1.5 hours. The absorbance at $A_{490}$ was measured by spectrophotometry.

T Cell Activation and Expansion

Immature DCs from CMV positive donors were transduced with the different viral vectors accordingly to protocol for viral transduction, were left untransduced or stimulated with TNFa (40 ng/ml) and poly IC (30 ug/mL). The next day, the cells were harvested and transferred to tubes and washed by PBS centrifugation (1500 rpm, 5 min). The supernatants were discarded and CMV pp65 peptides (10 ug) as well as beta 2 microglobulin (1 ug) were added where after the cells were incubated at 37 C for 4 hours. The cells were washed twice with PBS and then diluted in culture medium to a concentration of 1×10e5 cells/mL. In parallel, CD14– mononuclear cells from the same donor was thawed and washed with PBS centrifugation (1500 rpm, 5 min). The cells were diluted in culture medium to a concentration of 1×10e6 cells/mL. The prepared immature DCs and the CD14– mononuclear cells (including T cells) were co-cultured in a 1:10 ratio in T-25 flasks (5-10 mL/flask) for 11 days. At day 11 the expanded T cells were analyzed by flow cytometry for T cell markers and reactivity to CMV pp65 Tetramers.

Animal Experiments

Female C57BL/6 wildtype or Nu/Nu mice were obtained from Taconic M&B. Human Panc01 tumor cells were injected in to immunodeficient Nu/Nu mice. Upon detectable tumors, the tumors were injected ix with 1×10e9 VP virus with TMZ-CD154 per mouse. Tumor volume was measured at different time points. Murine Panc02 tumor cells were injected into wildtype mice. The mice were treated twice weekly with an adenovirus carrying murine TMZ-CD154+4-1BBL (1×10e9 VP/mouse). Gemcitabine (25 mg/kg) was given once weekly. Tumor size was monitored. Orthotopic model: mice were anaesthetized and catheterized (INSYTE.w24Gx3/4; BD Biosciences). The bladders were preincubated with 100 ul of 0.1 ug/ml poly-L-lysine (PLL, mol. wt 70 000-150000) (Sigma-Aldrich) to enhance tumor cell adherence. MB49 cells (2.5×10e5/mouse) were then implanted into the bladder. Mice received a local intravesical treatment of replication defective murine Ad5-CD154 or Ad5-Mock (1×10e8 ffu). Prior vector instillation the bladders were prewashed three times with the transduction enhancer Clorpactin WCS-90 (0.1% solution) (United-Guardian) and one PBS wash. For the determination of the amount of myeloid cells and T cells inside a bladder tumor, 24 hours after treatment, the tumors were taken, snap-frozen in liquid nitrogen and later stained and evaluated for the presence of $CD11b^+Gr-1^+$ cells by immunohistochemistry. A part of the tumor was mechanically disrupted to single cells and analyzed by flow cytometry to determine the number of infiltrating T cells. The pmel model: B16 tumor cells were grown subcutaneously in C57BL6 mice. Mice were divided in four groups. The first group received only PBS as a negative control. The second group was treated with AdCD40L, the third group with pmel T cells and the fourth group was first treated with AdCD40L as a primer to pmel T cell therapy. The regional ethical committee in Uppsala, Sweden, Dnr, approved all animal experiments: C86/10 and C54/13.

Immunohistochemistry

6 μm sections of snap frozen tissue embedded in OCT (Tissue-Tek Sakura) were fixed in ice cold acetone (Sigma-Aldrich) for 10 minutes and equilibrated in PBS. Slides were blocked in 10% normal goat serum (Dako) in PBS and non-specific rat $IgG2_b$ (BD Biosciences, 5 μg/ml) for 2 hours before incubation with primary antibodies (2 μg/ml, PE conjugated rat anti-mouse CD11b (Clone M1/70, BD Biosciences), FITC-conjugated rat anti-mouse Gr-1 (Clone RB6-8C5, BD Biosciences) diluted in blocking solution for 1 hat RT. Nuclei were counterstained with 2 μg/ml Hoechst 33342 (Sigma-Aldrich), followed by extensive washing in PBS and mounting with Fluoromount G (Southern Biotech). Microscopic pictures covering one entire tumor section per sample were taken on a Nikon Eclipse E100 microscope equipped with a Nikon DXM 1200 camera (Nikon Instruments Europe) using a PlanApochromat 20×/0.75 objective (Nikon). Images were analyzed with ImageJ (NIH). To determine the number of $CD11b^+Gr-1^+$ cells, double positive area was defined by manual thresholding and the nuclei within this area and the region of interest (ROI) were counted. The number of cells was expressed in relation to the total ROI.

The Blood Loop Model

Whole blood was circulated in heparinized tubings (2 ml/tube). Viruses were injected and after 4 hours incubation samples were taken for analysis of complement and cytokine activation. Pre samples were used as control. Control loops were injected with PBS or with the activation antibody anti-CD28.

Example 1

TMZ-CD154 Gene Transfer and Expression Using a Plasmid Gene Vehicle

To exemplify that a plasmid gene transfer system can be used to transfer the TMZ-CD154 gene leading to expression of TMZ-CD154 in transfected cells we have constructed a Plasmid-TMZ-CD154 gene vehicle and tested its capacity to deliver TMZ-CD154 to cells. Plasmid-TMZ-CD154 was constructed by inserting the human TMZ-CD154 gene into a pUC57-Kan expression plasmid as described in the "Materials and methods". The plasmid (5 ug) was then transfected into 293 cells ($1 \times 10^6$) and the expression of TMZ-CD154 was determined on the transfected cells at day 2 post transfection. Firstly, a proportion of the cells were lysed by a standard RIPA buffer and analyzed by gel electrophoresis and western blot (FIG. 2A). 293 cells transfected with either TMZ-CD154 or Mock plasmids were divided in two groups each. One of each group was not boiled in reducing sample buffer while the other was boiled and contained reducing sample buffer. In this way, the TMZ-CD154 can be identified as monomer (reduced) or oligomers (non-reduced). Both groups with Mock transfected cells were negative for CD154. In the TMZ-CD154 groups, monomeric TMZ-CD154 could be detected in both the reducing and the non-reducing groups as expected. However, the amount was less than in the reduced group. Only in the non-reducing group, oligomers of TMZ-CD154 could be detected. Interestingly, wild type CD154 could be detected in monomeric form in both groups suggesting that the TMZ-CD154 expression also trigger wild type CD154 expression. Secondly, the remaining cells were analyzed by flow cytometry. The transfection of 293 cells using Plasmid-TMZ-CD154 resulted in robust cell surface expression of TMZ-CD154 while a Mock control plasmid did not result in TMZ-CD154 expression (FIG. 2B). Thirdly, the supernatants from tumor cells untransduced or transduced with viruses expressing TMZ-CD154, wildtype CD154, or no transgenes (Mock) were analyzed by ELISA to determine the release of CD154 into the medium. The results demonstrate that TMZ-CD154 is not released in large quantities in the cell supernatant compared to wildtype CD154 (FIG. 2C). CD154 normally drive T cell activation and proliferation. TMZ-CD154 lacks the intracellular signaling domain and to demonstrate that TMZ-CD154 do not cause uncontrolled autoproliferation in T cells expressing TMZ-C154, T cells were activated with OKT-3 and IL2 prior to transduction with Ad5/35-TMZ-CD154, Ad5/35-Mock or left untransduced. The cells were cultured with or without IL2 for 48 hours and the cell number was determined. In FIG. 2D it is shown that IL2 drives expansion of the T cells and that the addition of TMZ-CD154 will not induce additional proliferation. The T cells will not proliferate without addition of IL2 independently of the presence of TMZ-CD154.

Example 2

TMZ-CD154 Gene Transfer and Expression Using a Viral Gene Vehicle

To exemplify that a viral gene vehicle transfer system can be used to transfer the TMZ-CD154 gene leading to its expression in cells we have constructed an adenoviral-based gene vehicle (Ad5/35-TMZ-CD154). Ad5/35-TMZ-CD154 was used to transduce 293 cells and TMZ-CD154 gene expression could thereafter robustly be detected on the cell surface of these cells while a Mock control virus could not induce TMZ-CD154 expression (FIG. 3A).

Example 3

TMZ-CD154 Gene Transfer and Expression on Tumor Cells

To exemplify that tumor cells can be engineered to express TMZ-CD40L we transferred TMZ-CD154 to a tumor cell line derived from pancreatic cancer (Panc01) using the Ad5/35-TMZ-CD154 vector. The transduced cell line expressed TMZ-CD154 upon transduction with Ad5/35-TMZ-CD154 but not with a Mock control vector (FIG. 3B). As previously shown, CD154-expressing tumor cells can be efficiently used as tumor cell vaccines in experimental models (Loskog A et al JU 2001), and used to stimulate in vitro DC activation and T cell expansion (Loskog A et al CGT 2002; Loskog et al JI 2004; Loskog et al CII 2006).

Example 4

Evaluating the Cell Killing Efficacy of the Oncolytic Ad5/35-TMZ-CD154 Vector To exemplify that tumor cells can be lysed by an oncolytic Ad5/35-TMZ-CD154 vector, tumor cells (A) Panc01, B) MiaPaCa2, C) BxPC3) D) Karpas-422 were transduced with Ad5/35-TMZ-CD154 (MOI 100 ffu/cell). At day 3 the viability of the cells was analyzed in a cell viability assay described in "Methods and materials" and the results demonstrated clearly that the oncolytic Ad5/35-TMZ-CD154 vector was better to kill tumor cells than using a replication defective virus or compared to untransduced cells (FIG. 4). The replication competent Ad5/35-TMZ-CD154 group showed enhanced cytotoxicity compared to the corresponding replication competent Ad5/35-Mock vector using the Panc01 cell line, and the other two cell lines also showed this increased cytotoxicity in TMZ-CD154 groups but the difference did not reach significance. The virus was equally effective in the lymphoma cell line Karpas-422.

Example 5

TMZ-CD154 Gene Transfer and Expression on Dendritic Cells

To exemplify that antigen-presenting cells such as dendritic cells can be activated by TMZ-CD154 we performed activation studies on human cells. Monocytes were sorted from peripheral blood mononuclear cells prepared from Buffy coats as described in "Methods and material" using CD14 MACS beads. The monocytes were then cultured for seven days with IL-4 and GM-CSF to differentiate them into immature dendritic cells. The immature dendritic cells were then cocultured with 293 cells transfected with the Plasmid-TMZ-CD154 or Mock control. After 2 days, the cells and supernatants were harvested and analyzed for the activation status of the dendritic cells by flow cytometry (CD83 activation marker) and ELISA (IL-12 activation marker). The results demonstrated that dendritic cells subjected to TMZ-CD154 stimulation matured into an activated phenotype that increased expression of CD83 and produced high levels of IL-12 (FIG. 5A, B). The results also demonstrate that membrane-bound CD154 including TMZ-CD154 induces a higher degree of activation of the dendritic cells since the TMZ-CD154 stimulated dendritic cells express a significantly higher amount of IL-12 than trimerized soluble (stCD40L) or multimeric forms of CD154 (multimer sCD40L).

Example 6

Transduction of Dendritic Cells with Ad5/35-TMZ-CD154

A. To exemplify that antigen-presenting cells such as dendritic cells can be transduced with the Ad5/35-TMZ-CD154 vector, immature dendritic cells were transduced with this vector or Mock control. The results demonstrated that dendritic cells transduced with Ad5/35-TMZ-CD154 matured into CD83-expressing activated dendritic cells producing IL-12 (FIG. 6A, B). The Ad5/35-TMZ-CD154 activated DCs had also increased HLA-DR, CD86 and CD70 expression (FIG. 6A).

B. To exemplify that antigen-presenting cells such as dendritic cells activated by TMZ-CD154 can induce antigen-specific T cell responses, such as anti-viral CMV-specific T cells, dendritic cells transduced with Ad5/35-TMZ-CD154 or Mock control was cultured with pp65 CMV peptides and cocultured with autologous T cells as described in "Methods and materials". After an 11-day expansion, the level of pp65-specific T cells was determined by tetramer staining and flow cytometry. The results show that TMZ-CD154-activated dendritic cells were able to activate and expand pp65-specific T cells (FIG. 7).

Example 7

It has previously been shown that human CD154-expressing adenovirus can induce activation of dog-derived immune cells (von Euler et al JIT 2008) and PBMCs from horses also show activation upon CD154-expressing adenovirus since the lymphocyte population expands post virus transduction of PBMCs (see "Methods and materials") (FIG. 8A). Moreover, MCP-1 is increased in the supernatants of the transduced PBMCs (FIG. 8B).

Example 8

In Vivo Tumor Growth Control

To exemplify that Ad5/35-TMZ-CD154 can control tumor growth in vivo, mice with human xenograft Panc01 tumors were treated 1× with Ad5/35-TMZ-CD154 or PBS. At day 7 the tumor volume was measured. The results demonstrate that Ad5/35-TMZ-CD154 can inhibit tumor progression in vivo due to the oncolytic capacity of the virus (FIG. 9). The immunological effects of the virus cannot be evaluated in murine models since the human TMZ-CD154 do not cross react to murine CD40. Further, the virus do not replicate in murine tumors, hence, human xenograft models must be used in immunodeficient mice.

Example 9

Combination of TMZ-CD154 with Other Immunomodulators in Vector Systems

To exemplify that TMZ-CD154 can be combined with other immune modulators the TMZ-CD154 gene construct was engineered together with either the 4-1BB ligand gene or a gene for an anti-IL6R scFv in plasmid and adenoviral vector systems.

```
SEQ ID NO: 6 (DNA), SEQ ID NO: 7 (protein)
TMZ-CD154/4-1 BBL gene
1-6: Kozak sequence
7-768: 4-1BBL
769-831: T2A peptide
832-1668: TMZ-CD154
      1    GCCACCATGG AATACGCCTC TGACGCTTCA CTGGACCCCG AAGCCCCGTG    Frame 1
                  M   E   Y   A   S   D   A   S   L   D   P   E   A   P   W 51    GCCTCCCGCG CCCCGCGCTC GCGCCTGCCG CGTACTGCCT TGGGCCCTGG    Frame 1
              P   P   A   P   R   A   R   A   C   R   V   L   P   W   A   L   V 101    TCGCGGGGCT GCTGCTGCTG CTGCTGCTCG CTGCCGCCTG CGCCGTCTTC    Frame 1
              A   G   L   L   L   L   L   L   L   A   A   A   C   A   V   F 151    CTCGCCTGCC CCTGGGCCGT GTCCGGGGCT CGCGCCTCGC CCGGCTCCGC    Frame 1
              L   A   C   P   W   A   V   S   G   A   R   A   S   P   G   S   A 201    GGCCAGCCCG AGACTCCGCG AGGGTCCCGA GCTTTCGCCC GACGATCCCG    Frame 1
              A   S   P   R   L   R   E   G   P   E   L   S   P   D   D   P   A 251    CCGGCCTCTT GGACCTGCGG CAGGGCATGT TTGCGCAGCT GGTGGCCCAA    Frame 1
              G   L   L   D   L   R   Q   G   M   F   A   Q   L   V   A   Q 301    AATGTTCTGC TGATCGATGG GCCCCTGAGC TGGTACAGTG ACCCAGGCCT    Frame 1
              N   V   L   L   I   D   G   P   L   S   W   Y   S   D   P   G   L 351    GGCAGGCGTG TCCCTGACGG GGGGCCTGAG CTACAAAGAG GACACGAAGG    Frame 1
              A   G   V   S   L   T   G   G   L   S   Y   K   E   D   T   K   E 401    AGCTGGTGGT GGCCAAGGCT GGAGTCTACT ATGTCTTCTT TCAACTAGAG    Frame 1
              L   V   V   A   K   A   G   V   Y   Y   V   F   F   Q   L   E 451    CTGCGGCGCG TGGTGGCCGG CGAGGGCTCA GGCTCCGTTT CACTTGCGCT    Frame 1
              L   R   R   V   V   A   G   E   G   S   G   S   V   S   L   A   L 501    GCACCTGCAG CCACTGCGCT CTGCTGCTGG GGCCGCCGCC CTGGCTTTGA    Frame 1
              H   L   Q   P   L   R   S   A   A   G   A   A   A   L   A   L   T 551    CCGTGGACCT GCCACCCGCC TCCTCCGAGG CTCGGAACTC GGCCTTCGGT    Frame 1
              V   D   L   P   P   A   S   S   E   A   R   N   S   A   F   G
```

```
601   TTCCAGGGCC GCTTGCTGCA CCTGAGTGCC GGCCAGCGCC TGGGCGTCCA    Frame 1
       F  Q  G  R  L  L  H  L  S  A  G  Q  R  L  G  V  H 651   TCTTCACACT GAGGCCAGGG CACGCCATGC CTGGCAGCTT ACCCAGGGCG    Frame 1
        L  H  T  E  A  R  A  R  H  A  W  Q  L  T  Q  G  A 701   CCACAGTCTT GGGACTCTTC CGGGTGACCC CCGAAATCCC AGCCGGACTC    Frame 1
         T  V  L  G  L  F  R  V  T  P  E  I  P  A  G  L 751   CCTTCACCGA GGTCGGAAGG CTCCGGGGAG GCAGAGGAA GTCTGCTAAC    Frame 1
        P  S  P  R  S  E  G  S  G  E  G  R  G  S  L  L  T 801   ATGCGGTGAC GTCGAGGAGA ATCCTGGGCC CAGAATGAAG CAGATCGAGG    Frame 1
         C  G  D  V  E  E  N  P  G  P  R  M  K  Q  I  E  D 851   ACAAGATCGA GGAGATCCTG AGCAAGATCT ACCACATCGA GAACGAGATC    Frame 1
        K  I  E  E  I  L  S  K  I  Y  H  I  E  N  E  I 901   GCCAGAATCA AGAAGCTGAT CGGCGAGAGA GGCGGCCGGG GCGGCGGCAT    Frame 1
        A  R  I  K  K  L  I  G  E  R  G  G  R  G  G  G  I 951   TTTTATGTAT TTACTTACTG TTTTTCTTAT CACCCAGATG ATTGGGTCAG    Frame 1
        F  M  Y  L  L  T  V  F  L  I  T  Q  M  I  G  S  A 1001  CACTTTTTGC TGTGTATCTT CATAGAAGGT TGGACAAGAT AGAAGATGAA    Frame 1
         L  F  A  V  Y  L  H  R  R  L  D  K  I  E  D  E 1051  AGGAATCTTC ATGAAGATTT TGTATTCATG AAAACGATAC AGAGATGCAA    Frame 1
        R  N  L  H  E  D  F  V  F  M  K  T  I  Q  R  C  N 1101  CACAGGAGAA AGATCCTTAT CCTTACTGAA CTGTGAGGAG ATTAAAAGCC    Frame 1
         T  G  E  R  S  L  S  L  L  N  C  E  E  I  K  S  Q 1151  AGTTTGAAGG CTTTGTGAAG GATATAATGT TAAACAAAGA GGAGACGAAG    Frame 1
        F  E  G  F  V  K  D  I  M  L  N  K  E  E  T  K 1201  AAAGAAAACA GCTTTGAAAT GCAAAAAGGT GATCAGAATC CTCAAATTGC    Frame 1
         K  E  N  S  F  E  M  Q  K  G  D  Q  N  P  Q  I  A 1251  GGCACATGTC ATAAGTGAGG CCAGCAGTAA AACAACATCT GTGTTACAGT    Frame 1
        A  H  V  I  S  E  A  S  S  K  T  T  S  V  L  Q  W 1301  GGGCTGAAAA AGGATACTAC ACCATGAGCA ACAACTTGGT AACCCTGGAA    Frame 1
         A  E  K  G  Y  Y  T  M  S  N  N  L  V  T  L  E 1351  AATGGGAAAC AGCTGACCGT TAAAAGACAA GGACTCTATT ATATCTATGC    Frame 1
        N  G  K  Q  L  T  V  K  R  Q  G  L  Y  Y  I  Y  A 1401  CCAAGTCACC TTCTGTTCCA ATCGGGAAGC TTCGAGTCAA GCTCCATTTA    Frame 1
         Q  V  T  F  C  S  N  R  E  A  S  S  Q  A  P  F  I 1451  TAGCCAGCCT CTGCCTAAAG TCCCCCGGTA GATTCGAGAG AATCTTACTC    Frame 1
        A  S  L  C  L  K  S  P  G  R  F  E  R  I  L  L 1501  AGAGCTGCAA ATACCCACAG TTCCGCCAAA CCTTGCGGGC AACAATCCAT    Frame 1
         R  A  A  N  T  H  S  S  A  K  P  C  G  Q  Q  S  I 1551  TCACTTGGGA GGAGTATTTG AATTGCAACC AGGTGCTTCG GTGTTTGTCA    Frame 1
        H  L  G  G  V  F  E  L  Q  P  G  A  S  V  F  V  N 1601  ATGTGACTGA TCCAAGCCAA GTGAGCCATG GCACTGGCTT CACGTCCTTT    Frame 1
         V  T  D  P  S  Q  V  S  H  G  T  G  F  T  S  F 1651  GGCTTACTCA AACTCTGA                                       Frame 1
        G  L  L  K  L  *

SEQ ID NO: 8 (DNA), SEQ ID NO: 9 (protein)
TMZ-CD154/aIL6R scFv gene
1-6: Kozak sequence
7-59: SigPep
60-798: aIL6R scFv
799-861: T2A peptide
862-1698: TMZ-CD154
    1   GCCACCATGC ACAGCTCAGC ACTGCTCTGT TGCCTGGTCC TCCTGACTGG    Frame 1
              M  H  S  S  A  L  L  C  C  L  V  L  L  T  G 51   GGTGAGGGCC CAGGTCCAAC TGCAGGAGAG CGGTCCAGGT CTTGTGAGAC    Frame 1
          V  R  A  Q  V  Q  L  Q  E  S  G  P  G  L  V  R  P
```

-continued

```
101   CTAGCCAGAC CCTGAGCCTG ACCTGCACCG TGTCTGGCTA CTCAATTACC   Frame 1
       S   Q   T   L   S   L   T   C   T   V   S   G   Y   S   I   T 151   AGCGATCATG CCTGGAGCTG GGTTCGCCAG CCACCTGGAC GAGGTCTTGA   Frame 1
       S   D   H   A   W   S   W   V   R   Q   P   P   G   R   G   L   E 201   GTGGATTGGA TACATTAGTT ATAGTGGAAT CACAACCTAT AATCCATCTC   Frame 1
       W   I   G   Y   I   S   Y   S   G   I   T   T   Y   N   P   S   L 251   TCAAATCCAG AGTGACAATG CTGAGAGACA CCAGCAAGAA CCAGTTCAGC   Frame 1
       K   S   R   V   T   M   L   R   D   T   S   K   N   Q   F   S 301   CTGAGACTCA GCAGCGTGAC AGCCGCCGAC ACCGCGGTTT ATTATTGTGC   Frame 1
       L   R   L   S   S   V   T   A   A   D   T   A   V   Y   Y   C   A 351   AAGATCCCTA GCTCGGACTA CGGCTATGGA CTACTGGGGT CAAGGCAGCC   Frame 1
       R   S   L   A   R   T   T   A   M   D   Y   W   G   Q   G   S   L 401   TCGTCACAGT CTCCTCAGGT GGCGGTGGCT CGGGTGGCGG TGGCTCGGGC   Frame 1
       V   T   V   S   S   G   G   G   G   S   G   G   G   G   S   G 451   GGTGGTGGGT CGGGTGGCGG CGGATCAGAC ATCCAGATGA CCCAGAGCCC   Frame 1
       G   G   G   S   G   G   G   G   S   D   I   Q   M   T   Q   S   P 501   AAGCAGCCTG AGCGCCAGCG TGGGTGACAG GGTGACCATC ACCTGTCGAG   Frame 1
       S   S   L   S   A   S   V   G   D   R   V   T   I   T   C   R   A 551   CCAGCCAGGA CATCAGCAGT TACCTGAATT GGTACCAGCA GAAGCCAGGA   Frame 1
       S   Q   D   I   S   S   Y   L   N   W   Y   Q   Q   K   P   G 601   AAGGCTCCAA AGCTGCTGAT CTACTACACC TCCCGCCTGC ACTCGGTGT   Frame 1
       K   A   P   K   L   L   I   Y   Y   T   S   R   L   H   S   G   V 651   GCCAAGCAGA TTCAGCGGTA GCGGTAGCGG TACCGACTTC ACCTTCACCA   Frame 1
       P   S   R   F   S   G   S   G   S   G   T   D   F   T   F   T   I 701   TCAGCAGCCT CCAGCCAGAG GACATCGCTA CCTACTACTG CCAGCAGGGT   Frame 1
       S   S   L   Q   P   E   D   I   A   T   Y   Y   C   Q   Q   G 751   AACACGCTTC CATACACGTT CGGCCAAGGG ACCAAGGTGG AAATCAAAGG   Frame 1
       N   T   L   P   Y   T   F   G   Q   G   T   K   V   E   I   K   G 801   CTCCGGGGAG GGCAGAGGAA GTCTGCTAAC ATGCGGTGAC GTCGAGGAGA   Frame 1
       S   G   E   G   R   G   S   L   L   T   C   G   D   V   E   E   N 851   ATCCTGGGCC CAGAATGAAG CAGATCGAGG ACAAGATCGA GGAGATCCTG   Frame 1
       P   G   P   R   M   K   Q   I   E   D   K   I   E   E   I   L 901   AGCAAGATCT ACCACATCGA GAACGAGATC GCCAGAATCA AGAAGCTGAT   Frame 1
       S   K   I   Y   H   I   E   N   E   I   A   R   I   K   K   L   I 951   CGGCGAGAGA GGCGGCCGGG GCGGCGGCAT TTTTATGTAT TTACTTACTG   Frame 1
       G   E   R   G   G   R   G   G   G   I   F   M   Y   L   L   T   V 1001  TTTTTCTTAT CACCCAGATG ATTGGGTCAG CACTTTTTGC TGTGTATCTT   Frame 1
       F   L   I   T   Q   M   I   G   S   A   L   F   A   V   Y   L 1051  CATAGAAGGT TGGACAAGAT AGAAGATGAA AGGAATCTTC ATGAAGATTT   Frame 1
       H   R   R   L   D   K   I   E   D   E   R   N   L   H   E   D   F 1101  TGTATTCATG AAAACGATAC AGAGATGCAA CACAGGAGAA AGATCCTTAT   Frame 1
       V   F   M   K   T   I   Q   R   C   N   T   G   E   R   S   L   S 1151  CCTTACTGAA CTGTGAGGAG ATTAAAAGCC AGTTTGAAGG CTTTGTGAAG   Frame 1
       L   L   N   C   E   E   I   K   S   Q   F   E   G   F   V   K 1201  GATATAATGT TAAACAAAGA GGAGACGAAG AAAGAAAACA GCTTTGAAAT   Frame 1
       D   I   M   L   N   K   E   E   T   K   K   E   N   S   F   E   M 1251  GCAAAAAGGT GATCAGAATC CTCAAATTGC GGCACATGTC ATAAGTGAGG   Frame 1
       Q   K   G   D   Q   N   P   Q   I   A   A   H   V   I   S   E   A 1301  CCAGCAGTAA AACAACATCT GTGTTACAGT GGGCTGAAAA AGGATACTAC   Frame 1
       S   S   K   T   T   S   V   L   Q   W   A   E   K   G   Y   Y 1351  ACCATGAGCA ACAACTTGGT AACCCTGGAA AATGGGAAAC AGCTGACCGT   Frame 1
       T   M   S   N   N   L   V   T   L   E   N   G   K   Q   L   T   V
```

-continued

```
1401    TAAAAGACAA GGACTCTATT ATATCTATGC CCAAGTCACC TTCTGTTCCA    Frame 1
         K  R  Q   G  L  Y  Y   I  Y  A    Q  V  T    F  C  S  N 1451    ATCGGGAAGC TTCGAGTCAA GCTCCATTTA TAGCCAGCCT CTGCCTAAAG    Frame 1
         R  E  A   S  S  Q    A  P  F  I   A  S  L    C  L  K 150     TCCCCCGGTA GATTCGAGAG AATCTTACTC AGAGCTGCAA ATACCCACAG    Frame 1
         S  P  G  R   F  E  R   I  L  L   R  A  A  N   T  H  S 1551    TTCCGCCAAA CCTTGCGGGC AACAATCCAT TCACTTGGGA GGAGTATTTG    Frame 1
         S  A  K    P  C  G  Q   Q  S  I   H  L  G    G  V  F  E 1601    AATTGCAACC AGGTGCTTCG GTGTTTGTCA ATGTGACTGA TCCAAGCCAA    Frame 1
         L  Q  P    G  A  S    V  F  V  N   V  T  D    P  S  Q 1651    GTGAGCCATG GCACTGGCTT CACGTCCTTT GGCTTACTCA AACTCTGA     Frame 1
         V  S  H  G   T  G  F    T  S  F   G  L  L  K   L  *
```

Example 10

Expression of TMZ-CD154/4-1BBL/aIL6R scFv Genes in Cells

A. To exemplify that Plasmid-TMZ-CD154/4-1BBL and Plasmid-aIL6R scFv can be used to transfer the TMZ-CD154/4-1BBL/aIL6R scFv genes and induce expression of those in cells, the Plasmid-TMZ-CD154/4-1BBL and Plasmid-aIL6R scFv was used to transfect 293 cells. The results demonstrate that all transgenes can be expressed upon transfection with these plasmids (FIG. 10). See "Methods and materials".

B. To exemplify that TMZ-CD154 can be expressed in trans with another gene separated by a 2A peptide Ad5/35-TMZ-CD154/4-1BBL was used to transduce dendritic cells. The results demonstrate that both transgenes can be expressed upon transduction with these viral vectors (FIG. 11). See "Methods and materials".

Example 11

Activation of Dendritic Cells by Combining TMZ-CD154 with 4-1BB Ligand or aIL6R scFv To exemplify that the combination of TMZ-CD154 and 4-1BB ligand can activate antigen-presenting cells such as dendritic cells, immature dendritic cells were transduced with Ad5/35-TMZ-CD154, Ad5/35-TMZ-CD154/4-1BBL or Ad5/35-TMZ-CD154/aIL6R scFv vectors, with a Mock vector or left untransduced. The results demonstrate that the transduced dendritic cells matured and were activated upon expressing the transgenes as shown by their CD83 expression (FIG. 12). Further, these combination viruses resulted in up-regulated CD70 on the dendritic cells compared to TMZ-CD154 alone even if TMZ-CD154-containing virus resulted in higher CD70 expression than if the dendritic cells were stimulated with an empty Mock virus (FIG. 13). Furthermore, the transduced dendritic cells expressed higher levels of IFNg and IL12 in the Ad5/35-TMZ-CD154/4-1BBL group (FIG. 14). See "Methods and materials".

Example 12

Activation of Antigen-Specific T Cells

To exemplify that dendritic cells stimulated by either the combination of TMZ-CD154/4-1BBL or the combination of TMZ-CD154/aIL6R can activate antigen-specific T cells, dendritic cells pulsed with pp65 CMV peptides transduced with either the Ad5/35-TMZ-CD154/4-1BBL vector or the Ad5/35-TMZ-CD154/aIL6R scFv vector were cocultured with autologous T cells. After an 11-day expansion, the number of activated pp65-specific T cells was determined. The results show that dendritic cells stimulated with either Ad5/35-TMZ-CD154/4-1BBL or Ad5/35-TMZ-CD154/aIL6R scFv could activate and expand antigen-specific T cells compared to the number of antigen-specific T cells in the mononuclear cells of a certain donor (FIG. 15A). The dendritic cells transduced with viruses containing both TMZ-CD154 and 4-1BB ligand or aIL6R scFv induced a higher number of cells post expansion than dendritic cells transduced with viruses containing TMZ-CD154 alone (FIG. 15B). The virus with both TMZ-CD154 and 4-1BB ligand expanded also NK cells in the cultures (FIG. 15C). See "Methods and materials".

Example 13

TMZ-CD154 Combined with Other Treatments

To exemplify that TMZ-CD154 can be combined with other therapies, tumor cells were treated with Ad5/35-TMZ-CD154, Ad5/35-TMZ-CD154/4-1BBL or A5/35-TMZ-CD154/aIL6R alone and in combination with gemcitabine (100 uM). The results demonstrate that Ad5/35-TMZ-CD154 can be combined with other treatments without loosing its capacity to kill cancer cells and that the combination with other treatments increases the tumor cell death (FIG. 16A). Panc02 murine pancreatic tumor cells were grown in C57BL6 mice and treated with an oncolytic adenovirus carrying TMZ-CD154+4-1BBL twice weekly 6×+/− weekly (3×) gemcitabine (25 mg/kg). Tumor growth was evaluated over time. C) Panc01 human pancreatic cells were transduced as in (A) above and cultured with or without paclitaxel (2 uM). * indicates p<0.05 differences. See "Methods and materials".

Example 14

The human TMZ-CD154 cannot activate murine CD40. A murine CD154 was therefore inserted into an Ad5 vector to demonstrate that in vivo Ad-CD154-mediated immune activation could be used to pre-sensitize the tumor to T cell therapy by reducing the presence of myeloid-derived suppressor cells which allows for T cell infiltration and survival in the tumor milieu. The results show that Ad-CD154-treated tumors reduced the number of myeloid-derived suppressor cells (FIG. 17A) and increased their capacity to attract and activate tumor-infiltrating T cells (FIG. 17B). See "Methods and materials". In fact, TMZ-CD154 can, alone, or together with 4-1BBL upregulate E-selectin and ICAM-I on the surface of endothelial cells. E-selectin and ICAM-I are important to recruit lymphocytes by increased attachment and diapedesis (FIG. 18).

Example 15—Summary of Preclinical Data Regarding LOAd703

Oncolytic Capacity

The capacity of LOAd703 to induce oncolysis of tumor cells has been evaluated in a panel of pancreatic cancer cell lines. All cell lines transduced with LOAd703 expressed the TMZ-CD40L and 41BBL transgenes and a dose-dependent cell death was seen over time. The cells died mainly of apoptosis as shown by detecting Annexin V by flow cytometry. However, healthy donor immune cells such as DCs, T cells or NK cells did not die from LOAd703-mediated oncolysis even if transgene expression was detected (DCs, T cells). Moreover, LOAd703 did not replicate in normal exocrine pancreatic cells demonstrating the regulated replication of this OV (FIG. 19). LOAd703 replication is not restricted to pancreatic cancer cells, other tumors can be targeted as well since most tumors have a dysregulated Rb pathway. Hence, LOAd703 could efficiently induce oncolysis of other tumor cell lines derived from B cell lymphoma or lung adenocarcinoma. Further, tumor cell death due to LOAd703-mediated oncolysis could be enhanced with chemotherapeutics such as gemcitabine or paclitaxel commonly used for patients with pancreatic cancer (FIG. 16).

LOAd703 was used as single dose or multiple (up to 6×) peritumoral injections in xenografted mice with established subcutaneous human pancreatic cancer tumors. LOAd703 could induce tumor regression dependent merely on oncolysis since xenograft models utilize immunodeficient mice. In aggressive models (larger tumors), gemcitabine could significantly increase the efficacy of LOAd703. These data provide a rationale that LOAd703 should be used in combination with standard of care gemcitabine for patients with pancreatic cancer (FIG. 16).

Immunostimulatory Effect

LOAd703 transduction of human monocyte-derived dendritic cells induced their maturation as shown by upregulated expression of cell surface markers such as CD83, and CD70 (FIGS. 12 and 13). The matured DCs also expressed and released the Th1-promoting cytokines IL12, TNFα, IL21 and IFNγ (FIG. 14). The activated DCs could in turn induce specific T cell responses and induce the expansion of both T cells and NK cells (FIG. 15). Hence, LOAd703 may potently induce Th1-mediated immunity against tumor cells. The immediate responses to LOAd703 in whole blood were demonstrated in a healthy donor blood loop model in which the virus is added to circulating whole blood in vitro. The results demonstrate that the LOAd703 serotype 5/35 virus did not induce immediate complement activation or cytokine release and was comparable with an Adenoserotype 5 virus encoding CD40L that has been used in patients (FIG. 20).

Unfortunately, LOAd703 cannot be investigated for its immunostimulatory effect in animal models because murine cells lack CD46, the receptor for viral uptake. Even if in vitro transduction can be enforced with a high virus per cell ratio it is difficult to reach the high virus per cell dose needed for efficient transduction in vivo. Nevertheless, a murine version of LOAd703 (mLOAd703) expressing murine TMZ-CD40L and 41BBL was used in a murine model of pancreatic cancer. Murine tumor cells were transduced in vitro and to express the two transgenes murine TMZ-CD40L and 4-1BBL. The transduced tumor cells were then injected into mice and the mice were monitored for tumor growth. The CD40L+4-1BBL+ tumor cells activated anti-tumor immunity and did form tumors. Control tumors lacking CD40L and 4-1BBL formed tumors within 14 days.

Since endothelial cells express CD40 they may, react to CD40L signaling. In a model using human endothelial cells (HUVEC) we have demonstrated that HUVEC cells upregulate receptors for T cell attachment, rolling and diapedesis upon LOAd703 transduction (FIG. 18). Hence, LOAd703 may enhance the infiltration of T cells into the tumor parenchyma thereby preventing the localization of tumor-infiltrating lymphocytes to the stroma, a common problem for tumor-specific T-cell activity. LOAd703 does not transduce murine cells in vivo since murine cells lack CD46 as stated above. Serotype 5 adenoviruses are better to transduce murine cells. Therefore, we used an Ad5 virus carrying murine CD40L to demonstrate that HUVEC cells were expressing the crucial receptors for T cell attachment, rolling and diapedesis upon transduction, and that in vivo gene transfer to the tumor indeed induced a massive infiltration of activated T cells showing that LOAd703 can as well be efficiently used to prime tumor prior to T cell therapy (FIG. 21).

Summary of In Vivo Toxicity Data

The full efficacy, and possible toxicity, of adenovirus-based oncolytic viruses armed with human immunostimulatory genes is difficult to estimate using animal models. Firstly, adenoviruses do not replicate sufficiently in murine cells. Hence, oncolysis needs to be determined in xenograft models using human tumor cells in immunodeficient mice. Off target toxicity, e.g. spreading of the virus leading to transduction and possible oncolysis of healthy cells cannot be determined in mice. Nevertheless, in vitro data showed that LOAd703 did not replicate in normal cells including exocrine pancreatic cells. Toxicity due to transgene expression is also hampered since human CD40L is not reactive in murine cells. Further, since murine tumor cells do not express CD46 the virus transduction is restricted to in vitro settings in which the viral particles per cell can be increased to circumvent the need of CD46. In vitro transduced murine pancreatic cancer cells expressing murine TMZ-CD40L and 4-1BBL were therefore injected subcutaneously in mice to determine the possible toxicity of the transgene expression. No adverse reactions were seen upon repeated (3×) injections.

LOAd703 was also injected repeatedly (4×) in tumor-bearing Syrian hamsters. Adenoviruses show some oncolytic activity in Syrian hamsters, nevertheless, the human transgenes do not function optimally and there are few tools to measure well-defined anti-tumor immune reactions in the hamster. Nevertheless, no adverse reactions were noted in the treated hamsters.

Example 16—Proof of Concept for TMZ-CD154+4-1BBL (LOAd703)

A protocol for a clinical trial to obtain proof of concept for the effectiveness of TMZ-CD154+4-1BBL has been developed. The Ad5/35-TMZ-CD154/4-1BBL oncolytic virus has been produced under GMP conditions and will be used as an investigational medicinal product to treat patients with pancreatic cancer diagnosed with 1-3 metastases starting their first standard of care gemcitabine treatment. Virus (500 µl) will be delivered by image-guided intratumoral injection in this study while in other studies with more spread disease, systemic delivery may be considered. This Phase I/IIa trial will evaluate a maximum of 17-26 patients dependent on safety profile. In brief, a first cohort of patients will receive a single dose Ad5/35-TMZ-CD154/4-1BBL (1×10e11 VP) complimentary to their standard of care gemcitabine treatment. The next cohort will receive an escalated dose of 5×10e11 VP Ad5/35-TMZ-CD154/4-1BBL (FIG. 22). If the single dose is safe, the next cohort will receive repeated dose (6×) Ad5/35-TMZ-CD154/4-1BBL (5×10e11 VP/treatment) complimentary to standard of care (FIG. 23). The patients will be monitored for safety, efficacy on tumor control, virus pharmacokinetics and formation of anti-virus antibodies as well as monitored for immune activation including phenotyping immune cells and measuring serum or plasma and biopsies for protein markers such as cytokines. A successful Phase I/IIa trial will lead to a randomized Phase IIb study comparing gemcitabine alone to the combination of gemcitabine and Ad5/35-TMZ-CD154/4-1BBL.

In the following the study is described further.

Investigational Product: LOAd703

Active substance: Modified adenovirus serotype 5/35 containing a CMV promoter-driven transgene cassette with the human transgenes for a membrane-bound CD40 ligand (TMZ-CD40L) and full length 4-1BBL.

Manufacturer: Baylor College of Medicine, Houston, Tex.

Dose: $1-5\times10^{11}$ virus particles (VP) in 500 µl suspension per injection. A higher concentration of viral particles in 500 ul suspension may cause aggregation of the viral particles and is not recommended.

Dosage form: LOAd703 adenoviral particles in suspension, 650 ul per vial, $1\times10^{12}$VP/ml, (low dose; $2\times10^{11}$ VP/ml).

Administration

LOAd703 will be delivered by image-guided intratumoral injection of 500 ul LOAd703 virus in suspension. Dependent on the localization of the tumor, different imaging techniques can be used at the discretion of the Investigator.

For tumors easily accessible to percutaneous injection, LOAd703 can preferably be done by abdominal ultrasound-guided percutaneous injection of the tumor metastasis. Other tumors may be better accessible via endoscopic ultrasound-guided injection. Other imaging techniques such as computer tomography (CT)-guided injections may also be used at the discretion of the Investigator.

Rationale for the Phase I/IIa Doses

The initial dose will be a single injection of $1\times10^{11}$ VP LOAd703 in a 500 ul suspension per treatment. The rationale is based on previous experience with intratumoral injection of the predecessor AdCD40L that has safely been injected repeatedly (4-8) at the dose $2.5\times10^{11}$ VP in a 500 ul suspension. A lower initial dose was chosen since LOAd703 unlike AdCD40L is an oncolytic virus. If this dose is safe in two enrolled patients, the next dose level is a single dose of $5\times10e^{11}$ VP in a 500 ul suspension, which will be given to an additional two patients. The next three patients will receive six intratumoral injections of LOAd703 every other week of the chosen dose. If safe, the multiple dose will be used for ten patients in the Phase IIa part of the study to confirm safety in a larger cohort.

Since the immune system is escalating reactivity upon repeated exposure to stimulation, we do not expect lasting efficacy, or toxicity, in the single dose patients. We have therefore chosen 2+2 design during dose escalation using single dose and for multiple doses the standard 3 patients is used to confirm safety prior to entering Phase IIa.

If dose-limiting toxicity (DLT) is determined, adjustments of the dose can be done.

Patient Population

Pancreatic ductal adenocarcinoma (PDAC) is a one of the most aggressive cancers and has the highest mortality rate of all major cancers. Even if pancreatic cancer is an orphan indication it is the fourth deadliest cancer in the US. Initially, there are few symptoms and patients are therefore often diagnosed when the tumor is already metastasized. It has a highly drug resistant profile and few drugs have shown significant survival benefit. Standard of care is currently gemcitabine but combination therapy with other drugs such as paclitaxel has recently been approved for metastasized pancreatic cancer. 10-20% of the diagnosed patients have localized cancer but only 20% of them are subjected to surgery with adjuvant chemotherapy. 1-year survival for pancreatic cancer is about 20% and after 5 years, only 6% are still alive. However, considering only the subgroup of patients eligible for surgery the overall survival at 5 years is 20%.

In this study, patients with locally advanced disease (single lesion) and those with advanced but few (2-3) lesions will be enrolled.

Study Objective and Endpoints

Patients diagnosed with PDAC have limited treatment options and a dismal prognosis even if the tumor is still localized to the pancreas or has metastasized to few sites only. Local immunostimulatory gene therapy may be of value for patients with single or few lesions but with high-risk profile. These patients will receive their standard of care therapy (gemcitabine) that will not only target the tumor but also reduce the levels of suppressive immune cells. LOAd703 will be administered to one single lesion. The adenovirus particles per se will interact with pathogen-associated molecular patterns (PAMPs) such as TLR2 and TLR9 that leads to inflammatory responses. Oncolysis will aid antigen uptake by antigen-presenting cells such as DCs and allow new virions to infect nearby cells prolonging the expression of the immunostimulatory transgenes. While TMZ-CD40L can activate DCs that engulf tumor antigens to stimulate de novo CTL, NK cell and M1 macrophage responses and activate endothelial cells to increase lymphocyte entry into the tumor parenchyma, 4-1BBL may restimulate preexisting tumor-infiltrating T cells and NK cells to aid eradication of tumor cells as well as prolonging the survival of the de novo stimulated immune cells when entering the tumor. The generated immunity may then also act on distant tumor cells to reduce tumor growth rate or even prevent formation of new metastatic lesions.

Objectives

Phase I

The Phase I objective is to determine the feasibility and safety of image-guided intratumoral injection of LOAd703 at two dose levels, two patients per dose, and six repeated injections of the chosen dose in three patients during standard of care treatment.

Phase IIa

The Phase IIa objective is to determine safety and effect of repeated LOAd703 therapy combined with standard of care treatment.

Endpoints

Phase I

The endpoint of the Phase I component is to evaluate toxicity.

1. Toxicity by standard criteria using physical examination, hematological and clinical chemistry analysis.

2. LOAd703 virus copies in blood and biopsies (multiple dose only) using quantitative real time PCR.

3. Anti-adenoviral antibodies in blood using ELISA.

4. Immunological protein profile in blood and tumor lysate (multiple dose only) by ELISA and/or multiplex-based methods such as ProSeek 5. Immunological cell profile in blood by flow cytometry and ELISPOT.

6. Effect on tumor by appropriate imaging dependent on tumor localization and by monitoring tumor marker CA 19-9.

Phase IIa

The endpoints of the Phase IIa part are effects on tumor and safety.

1. Toxicity by standard criteria using physical examination, hematological and clinical chemistry analysis.

2. LOAd703 virus copies in biopsies and blood using quantitative real time PCR.

3. Anti-adenoviral antibodies in blood using ELISA.

4. Immunological protein profile in blood and tumor lysates by ELISA and/or a multiplex-based method such as ProSeek.

5. Immunological cell profile in blood by flow cytometry and ELISPOT.

6. Effect on tumor by appropriate imaging dependent on tumor localization and by monitoring tumor marker CA 19-9.

Trial Design

Summary of Trial Design

The trial consists of a dose-escalating Phase I with single and multiple doses, and a confirming Phase IIa with multiple doses at the dose level selected in Phase I. 7 patients will be enrolled in Phase I unless DLT requires dose adjustments and additional cohorts prior to entry into Phase IIa. Hence, a maximum of 7-16 patients can be treated in Phase I. A maximum of 10 patients will be enrolled in the Phase IIa component. By applying Gehan's methodology, the risk that LOAd703 incorrectly lacks effect (OR) after 10 patients in Phase IIa in at least one patient despite that fact that the treatment in reality confers up to 30% OR, is less than 5%. In total, the study intends to treat a maximum of 17-26 patients.

Phase I

The patients will be informed about the study and sign informed consent whereby they enter a screening phase to determine eligibility including sampling for health status and radiology. The patients will initiate their first three weeks cycle of standard of care gemcitabine (1000 mg/m$^2$) followed by a week of rest. During the resting week, the first two patients will receive one dose of image-guided intratumoral injection of 1×10$^{11}$ VP LOAd703 and the consecutive two patients one dose of 5×10$^{11}$ VP LOAd703 (FIG. 22). The treatment of the two consecutive patients can begin when the two first patients has passed final follow-up without dose limiting toxicity (DLT). The patients will stay overnight after virus treatment for observation. The patients will thereafter continue another three-week cycle of gemcitabine and one week of rest. Blood samples will be taken to evaluate toxicity, virus pharmacokinetics (e.g. spreading to blood) and immune reactions as indicated in FIG. 22. During study screening and at final follow-up, patients will undergo radiology after which they will come off study.

If the single dose regimen is safe, the next three patients will receive multiple (6×) intratumoral injections every other week in parallel to their standard of care gemcitabine therapy (FIG. 23). If no immediate reactions occurred post LOAd703 injection during dose escalation in the first four single dose patients, the patients receiving multiple doses do not need to stay overnight but will be observed for at least 4 hours post virus injection, at the discretion of the Investigator, and can then be released from the hospital.

Biopsies will be taken prior to the first and one week after the last LOAd703 injection. Blood samples will be taken at different time points to evaluate toxicity, virus pharmacokinetics (e.g. spreading to blood) and immune reactions as indicated in FIG. 23. Every other month, imaging will be used to determine tumor size. At six months, patients will undergo final follow-up analyses and thereafter the patient will come off-study. After participation in the trial, the patients will continue their standard of care regimen accordingly to the clinical routines at the hospital.

When three patients have been treated at a safe dose of multiple virus injections, as judged when all of these patients have past at least two weeks since the final virus dose, the Phase IIa part of the trial can be initiated.

If DLTs occur during dose escalation or multiple doses, the dose must be adjusted.

Phase IIa

The patients will be informed about the study and sign informed consent whereby they enter a screening phase to determine eligibility including sampling for health status and imaging. The patients will initiate their first three weeks cycle of standard of care gemcitabine (1000 mg/m$^2$) followed by a week of rest. During the resting week, the patients will initiate LOAd703 treatment with image-guided intratumoral injection of the selected dose of LOAd703. The LOAd703 injections will be given every other week in parallel to their standard of care gemcitabine treatment. Six virus doses will be given.

Biopsies will be taken prior to the first and one week after the last LOAd703 injection. Blood samples will be taken at different time points to evaluate toxicity, virus pharmacokinetics (e.g. spreading to blood) and immune reactions as indicated in FIG. 23. Every other month, radiology will determine tumor size. At six months, the patients will undergo final follow-up analyses and thereafter the patient will come off-study. After participation in the trial, patients will continue their standard of care regimen accordingly to the clinical routine at the hospital. In total, 10 patients will be treated in Phase IIa.

Duration of Study

The patients will participate in the study for two (single dose) to six months (multiple doses). In total, 17-26 patients will be enrolled. The study is estimated to be completed within 2 years.

End of Study

The end of study is defined as the date of the last visit of the last patient undergoing the trial.

Specific Embodiments

1. A nucleotide sequence comprising the structure

OD-(L)-TD-ED wherein

OD is an oligomerization domain,

L is a linker, which optionally is present,

TD is a transmembrane domain derived from CD154 or from any type II transmembrane protein, and ED is an extracellular domain of CD154 selected from i) SEQ ID NO: 11, i.e. residues 199-846 of SEQ ID NO: 1, ii) SEQ ID NO: 11, i.e. residues 199-846 of SEQ ID NO: 1, but wherein one or more of the nucleic acid residues 397-420 of SEQ ID NO: 1 have been deleted or exchanged with another nucleic acid to avoid cleavage of the molecule, iii) SEQ ID NO 12, i.e. residues 127-846 of SEQ ID NO: 3, iv) SEQ ID NO: 13, i.e. residues 127-844 of SEQ ID NO: 4, v) SEQ ID NO: 14, i.e. residues 127-844 of SEQ ID NO: 5, vi) a nucleotide sequence having at least 95%, 98% or 99% sequence identity with a sequence defined in any of i)-v), or vi) a corresponding extracellular CD154 domain from a mammal,
with the proviso that the nucleotide sequence does not comprise the intracellular CD154 region corresponding to equivalent nucleotide sequence of SEQ ID NO: 16.

2. A nucleotide sequence according to item 1, wherein the transmembrane domain is derived from CD154, human OX40 ligand or human CD70.

3. A nucleotide sequence according to item 2, wherein the transmembrane domain has at least 90% sequence identity with
i) SEQ ID NO: 17, i.e. residues 127-198 of SEQ ID NO 1,
ii) SEQ ID NO: 20, i.e. transmembrane domain of human OX40 ligand, or
iii) SEQ ID NO: 22, i.e. transmembrane domain of human CD70.

4. A nucleotide sequence according to item 3, wherein the transmembrane domain has at least 95%, 96%, 97%, 98%, 99% or 100% sequence identity with SEQ ID NO: 17, SEQ ID NO: 20 or SEQ ID NO: 22.

5. A nucleotide sequence according to item 4, wherein the transmembrane domain has SEQ ID NO: 17.

6. A nucleotide sequence according to any of the preceding items, wherein the oligomerization domain is an isoleucine zipper or a trimerization domain of T4 fibritin.

7. A nucleotide sequence according to item 6, wherein the oligomerization domain is the isoleucine zipper having SEQ ID NO: 23, i.e. residues 10-108 of SEQ ID NO: 1.

8. A nucleotide sequence according to any of the preceding items further comprising a Kozak sequence.

9. A nucleotide sequence according to item 8, wherein the Kozak sequence corresponds to residues 1-9 of SEQ ID NO: 1.

10. A nucleotide sequence according to any of the preceding items having at least 90% sequence identity with SEQ ID NO: 1, SEQ ID NO. 3, SEQ ID NO: 4 or SEQ ID NO: 5.

11. A nucleotide sequence according to any of the preceding items having at least 95% or 98% sequence identity with SEQ ID NO: 1, SEQ ID NO. 3, SEQ ID NO: 4 or SEQ ID NO: 5.

12. A nucleotide sequence according to any of the preceding items having 100% sequence identity with SEQ ID NO: 1, SEQ ID NO. 3, SEQ ID NO: 4 or SEQ ID NO: 5.

13. A nucleotide sequence according to any of the preceding items in combination with an immunomodulator.

14. A nucleotide sequence according to any of the preceding items, wherein the immunomodulator is 4-1BB ligand gene, or a gene for an anti IL6R scFv.

15. A nucleotide sequence according to any of the preceding items in combination with a signaling pathway modulator.

16. A nucleotide sequence according to any of the preceding items, wherein the signaling pathway modulator is an anti-IL6R scFv.

17. A nucleotide sequence according to any of items 1-14 in combination with a signaling pathway blocker.

18. A nucleotide sequence according to item 14 having at least 95%, 98% or 100% sequence identity with SEQ ID NO: 6 or SEQ ID NO: 8.

19. A nucleotide sequence according to any of the preceding items for use in medicine.

20. A nucleotide sequence according to any of the preceding items for use as a diagnostic tool.

21. A protein encoded by a nucleotide sequence as defined in any of items 1-20.

22. A protein comprising the structure

OD-(L)-TD-ED, wherein
OD is an amino acid sequence corresponding to an oligomerization domain,
L is a linker, which optionally is present,
TD is an amino acid sequence corresponding to a transmembrane domain, and
ED is an amino acid sequence corresponding to an extracellular domain of CD154 selected from
i) amino acid residues corresponding to the nucleotides of SEQ ID NO: 11, i.e. residues 199-846 of SEQ ID NO: 1,
ii) amino acid residues corresponding to the nucleotides of SEQ ID NO: 11, i.e. residues 199-846 of SEQ ID NO: 1, but wherein one or more of the amino acid residues corresponding to the nucleotides of 397-420 of SEQ ID NO: 1 have been deleted or exchanged with another amino acid to avoid cleavage of the molecule,
iii) amino acid residues corresponding to the nucleotides of SEQ ID NO 12, i.e. residues 127-846 of SEQ ID NO: 3,
iv) amino acid residues corresponding to the nucleotides of SEQ ID NO: 13, i.e. residues 127-844 of SEQ ID NO: 4,
v) amino acid residues corresponding to the nucleotides of SEQ ID NO: 14, i.e. residues 127-844 of SEQ ID NO: 5,
vi) an amino acid sequence having at least 95%, 98% or 99% sequence identity with a sequence defined in any of i)-v), or
vi) a corresponding extracellular CD154 domain from a mammal, with the proviso that the protein does not comprise an amino acid sequence corresponding to the intracellular CD154 region corresponding to the amino acid sequence SEQ ID NO: 15.

23. A protein according to item 22, wherein ED has at least 90% or at least 95% sequence identity to SEQ ID NO: 24.

24. A protein according to any one of items 21-23, wherein the oligomerization domain is an isoleucine zipper domain or a trimerization domain of T4 fibritin.

25. A protein according to any of items 21-24, wherein the transmembrane domain is derived from transmembrane domain of CD154 or any type II transmembrane protein.

26. A protein according to any of items 22-25, wherein the amino acid sequence corresponding to the transmembrane domain has at least 90%, 95%, 98% or 100% sequence identity to SEQ ID NO: 18.

27. A protein according to any of items 22-26, wherein one or more of the residues of SEQ ID NO: 18 may be deleted or substituted with another amino acid.

28. A protein according to item 27, wherein the residues are aa14 and/or aa16.

29. A protein according to any of items 21-28 having at least 90%, 95% or 98% sequence identity with SEQ ID NO: 2.

30. A protein according to any of items 21-29 having 100% sequence identity with SEQ ID NO: 2.

31. A protein according to any of items 21-30 for use in medicine.

32. A protein according to any of items 21-31 for use in treatment of diseases defined herein.

33. A protein as defined in any of items 21-32 in combination with a drug substance selected from anti-cancer agents, immunomodulators and other drug substances as defined herein for use in medicine 34. A vehicle comprising a nucleotide sequence as defined in any of items 1-20.

35. A vehicle according to item 34 selected from plasmids, viral vectors, transposons, cells, artificial cells, and artificial vehicles 36. A vehicle according to item 34 or 35 in the form of a virus.

37. A vehicle according to item 36, wherein the virus is an adenoviral serotype 5/35 virus.

38. A vehicle according to item 37, wherein adenoviral 5/35 virus has an E2F promoter region/binding sites upstreams of the E1A gene, may have an Sp1 site upstreams of the E1A gene, a E1A Δ24 deletion, E3 Δ6.7K/gp19K, and the transgene cassette including the pCMV and transgene/s is inserted after the L5 gene region.

39. A vehicle according to any of items 34-38 comprising TMZ-CD154 nucleotide as defined in SEQ ID NO: 1.

40. A vehicle according to any of items 34-39 further comprising 4-1BB ligand gene or a gene for anti-IL6R scFv.

41. A combination of two or more vehicles as defined in any of items 34-40.

42. A combination of two vehicles, wherein a first vehicle is as defined in any one of items 34-41 and a second vehicle comprising an immunomodulator such as 4-1BB ligand gene or a gene for anti-IL6R scFv.

43. A vehicle according to any of items 34-42 for use in medicine.

44. A vehicle according to any of items 34-43 for use in the treatment of diseases defined herein.

45. A vehicle according to any of items 34-43 for use in the treatment of cancer.

46. A vehicle according to any of items 34-43 for use in the treatment of solid tumors.

47. A vehicle according to any of items 34-43 for use in the treatment of pancreatic cancer.

48. A vehicle as defined in any of items 34-44 in combination with a drug substance selected from anti-cancer agents, immunomodulators and other drug substances as defined herein for use in medicine.

The invention claimed is:

1. A nucleotide sequence encoding an insoluble membrane-bound CD154 fusion protein comprising, from 5' to 3':

OD-(L)-TD-ED wherein
the OD is an oligomerization domain selected from the group consisting of an isoleucine zipper and a trimerization domain of T4 fibritin,
the L is a linker, which optionally is present,
the TD is a transmembrane domain of a type II transmembrane protein, and
the ED is an extracellular domain of a CD154 protein,
with the proviso that the nucleotide sequence does not comprise a sequence encoding the intracellular region of a CD154 protein and does not comprise a sequence encoding the intracellular region of a CD40 protein.

2. The nucleotide sequence of claim 1, wherein the TD is a TD of a CD154 protein.

3. The nucleotide according to claim 1, wherein the nucleotide sequence encoding the ED is selected from:
   (i) the nucleotide sequence of SEQ ID NO: 11,
   (ii) a variant of the nucleotide sequence of SEQ ID NO:11, wherein one or more of the nucleic acids 397-420 of the nucleotide sequence of SEQ ID NO:11 have been deleted or exchanged with another nucleic acid to avoid cleavage of the CD154 fusion protein,
   (iii) the nucleotide sequence of SEQ ID NO: 12,
   (iv) the nucleotide sequence of SEQ ID NO: 13,
   (v) the nucleotide sequence of SEQ ID NO: 14,
   (vi) a nucleotide sequence having at least 98% sequence identity with a nucleotide sequence defined in any of (i)-(v), and wherein the encoded ED is functional, and
   (vi) the ED coding sequence of a CD154 protein from a mammal.

4. The nucleotide sequence according to claim 1, wherein the sequence encoding the intracellular CD154 region is the nucleotide sequence of SEQ ID NO:16.

5. The nucleotide sequence according to claim 1, wherein the nucleotide sequence encoding the TD is the TD encoding sequence from CD154, human OX40 ligand, or human CD70 proteins.

6. The nucleotide sequence according to claim 5, wherein the nucleotide sequence encoding the TD has at least 99% sequence identity with a sequence selected from:
   (i) the nucleotide sequence of SEQ ID NO:17,
   (ii) the nucleotide sequence of SEQ ID NO:20, and
   (iii) the nucleotide sequence of SEQ ID NO:22, and
   wherein the TD retains the predicted hydrophobic region.

7. The nucleotide sequence according to claim 6, wherein the nucleotide sequence encoding the TD is selected from the nucleotide sequence of SEQ ID NO:17, SEQ ID NO:20 or SEQ ID NO:22.

8. The nucleotide sequence according to claim 7, wherein the nucleotide sequence encoding the TD has the nucleotide sequence of SEQ ID NO: 17.

9. The nucleotide sequence according to claim 1, wherein the nucleotide sequence encoding the OD is the isoleucine zipper having the nucleotide sequence of SEQ ID NO:23.

10. The nucleotide sequence according to claim 1, further comprising a Kozak sequence.

11. The nucleotide sequence according to claim 10, wherein the Kozak sequence has the sequence of residues 1-9 of the nucleotide sequence of SEQ ID NO:1.

12. The nucleotide sequence according to claim 1, having at least 98% sequence identity with the nucleotide sequence of SEQ ID NO:1, SEQ ID NO:3, SEQ ID NO:4 or SEQ ID NO:5, and wherein the protein encoded by the nucleotide sequence binds CD40.

13. The nucleotide sequence according to claim 1, which is selected from the nucleotide sequence of SEQ ID NO:1, SEQ ID NO:3, SEQ ID NO:4 or SEQ ID NO:5.

14. A combination of the nucleotide sequences of claim 1 and a signaling pathway modulator or a signaling pathway blocker.

15. A vehicle that encodes the nucleotide sequence according to claim 1.

16. The vehicle according to claim 15, selected from a plasmid, a viral vector, a transposon, a cell, an artificial cell, and an artificial vehicle.

17. The vehicle according to claim 15 wherein the vehicle is a virus.

18. The vehicle according to claim 17, wherein the virus is an adenoviral serotype 5/35 virus.

19. The vehicle according to claim 18, wherein the adenoviral 5/35 virus has at least one of an E2F promoter region binding site upstream of the E1A gene with an optional Sp1 site upstream of the E1 A gene, an E1AΔ24 deletion, an E3 Δ46.7K deletion, an E3Δgp19K deletion, and a transgene cassette with one or more transgenes including pCMV inserted after the L5 gene region.

20. A combination of two vehicles, wherein a first of the two vehicles is as defined in claim 18 and a second of the two vehicles encodes a gene for an immunomodulator.

21. The combination according to claim 20, wherein the immunomodulator is selected from 4-IBB ligand and an anti-IL6R scFv.

22. The vehicle according to claim 18, further encoding a gene for an interleukin selected from interleukin-2 (IL-2), interleukin-7 (IL-7), interleukin-15 (IL-15), and interleukin-21 (IL-21).

23. A combination of two vehicles, comprising a first vehicle as defined in claim 18 and a second vehicle encoding a gene for an interleukin selected from Il-2, IL-7, IL-15 and IL-21.

24. A combination of three vehicles, comprising a first vehicle as defined in claim 18, a second vehicle encoding a gene for an immunomodulator, and a third vehicle encoding a gene for an interleukin selected from Il-2, IL-7, IL-15 and IL-21.

25. A combination according to claim 24, wherein the immunomodulator is selected from 4-IBB ligand and an anti-IL6R scFv.

26. The vehicle according to claim 18 further encoding (i) a gene for an interleukin selected from Il-2, IL-7, IL-15 and IL-21, and (ii) a gene for an immunomodulator.

27. The vehicle according to claim 26, wherein the immunomodulator is selected from 4-IBB ligand and an anti-IL6R scFv.

28. The vehicle according to claim 15, encoding the TMZ-CD154 nucleotide sequence of SEQ ID NO:1.

29. The vehicle according to claim 15, further encoding a 4-1BB ligand gene or a gene for an anti-IL6R single chain variable fragment.

30. A combination of two or more vehicles as defined in claim 16.

31. A combination of the nucleotide sequence encoding the membrane-bound CD154 fusion protein of claim 1 and a nucleotide sequence that encodes an immunomodulator.

32. The combination according to claim 31, wherein the nucleotide sequence that encodes the immunomodulator is a 4-IBB ligand gene, or a gene that encodes an anti-IL6R single chain variable fragment (scFv).

33. The combination according to claim 32, wherein the combination of the nucleotide sequence encoding the membrane-bound CD154 fusion protein and the nucleotide sequence that encodes the immunomodulator has at least 98% sequence identity with the nucleotide sequence of SEQ ID NO:6 or SEQ ID NO:8.

34. A modified adenovirus serotype 5/35 containing a cassette comprising a CMV promoter operably linked to a transgene encoding the human membrane-bound CD40 ligand comprising nucleotides 127-846 of SEQ ID NO:1 and a transgene encoding the full length human 4-1BBL comprising nucleotides 7-768 of SEQ ID NO:6.

35. The modified adenovirus serotype 5/35 virus according to claim 34, further comprising
(i) E2F promoter sites upstream of an E1A gene,
(ii) a Sp-1 site upstream of the E1A gene,
(iii) a E1A Δ24 deletion,
(iii) E3 Δ6.7K/gp19K, and
(iv) a L5 gene region, wherein the cassette comprising the CMV promoter and transgenes is inserted after the L5 gene region.

* * * * *